United States Patent
Sauer

(10) Patent No.: US 11,213,389 B2
(45) Date of Patent: Jan. 4, 2022

(54) PROSTHETIC SUTURING DEVICE AND METHODS THEREOF

(71) Applicant: LSI Solutions, Inc., Victor, NY (US)

(72) Inventor: Jude S. Sauer, Pittsford, NY (US)

(73) Assignee: LSI SOLUTIONS, INC., Victor, NY (US)

( * ) Notice: Subject to any disclaimer, the term of this patent is extended or adjusted under 35 U.S.C. 154(b) by 663 days.

(21) Appl. No.: 15/735,816

(22) PCT Filed: Oct. 17, 2017

(86) PCT No.: PCT/US2017/057057
§ 371 (c)(1),
(2) Date: Dec. 12, 2017

(87) PCT Pub. No.: WO2018/075568
PCT Pub. Date: Apr. 26, 2018

(65) Prior Publication Data
US 2020/0060674 A1    Feb. 27, 2020

Related U.S. Application Data

(60) Provisional application No. 62/409,304, filed on Oct. 17, 2016.

(51) Int. Cl.
*A61F 2/24*    (2006.01)
*A61B 17/04*    (2006.01)
(Continued)

(52) U.S. Cl.
CPC ........ *A61F 2/2427* (2013.01); *A61B 17/0469* (2013.01); *A61B 17/0482* (2013.01);
(Continued)

(58) Field of Classification Search
CPC .......... A61F 2/2427; A61F 2220/0008; A61B 17/0482; A61B 17/0469;
(Continued)

(56) References Cited

U.S. PATENT DOCUMENTS 6,187,019 B1    2/2001    Stefanchik et al.
2005/0154403 A1*    7/2005    Sauer ................ A61B 17/0491
606/139

(Continued)

OTHER PUBLICATIONS

Jan. 18, 2018; International Search Report, Thomas, Shane; ISR for PCT/US2017/057057.

*Primary Examiner* — Thomas McEvoy
(74) *Attorney, Agent, or Firm* — Michael E. Coyne; Christopher B. Miller

(57) ABSTRACT

A cassette is disclosed for use in a prosthetic suturing device. The cassette has a base. The base has a pair of pivots, a pair of alignment tabs, and at least one retention latch. The cassette also has a cover coupled to the base. The cover has at least one retention latch. The cover also defines one or more ferrule holders. The cassette further has one or more needles guided by the base and the cover. A surgical suturing device is also disclosed for use with a cassette. The suturing device has a cassette receiver and one or more needle drivers, each needle driver having a needle receiver positioned within the cassette receiver.

20 Claims, 95 Drawing Sheets

(51) Int. Cl.
*A61B 17/32* (2006.01)
*A61B 17/3209* (2006.01)
*A61B 17/06* (2006.01)
*A61B 17/00* (2006.01)
*A61B 90/00* (2016.01)

(52) U.S. Cl.
CPC .... *A61B 17/0491* (2013.01); *A61B 17/06133* (2013.01); *A61B 17/3209* (2013.01); *A61B 17/320016* (2013.01); *A61B 2017/00243* (2013.01); *A61B 2017/00464* (2013.01); *A61B 2017/00477* (2013.01); *A61B 2017/00907* (2013.01); *A61B 2017/0472* (2013.01); *A61B 2017/320052* (2013.01); *A61B 2090/0811* (2016.02); *A61F 2220/0008* (2013.01)

(58) Field of Classification Search
CPC .. A61B 2017/00477; A61B 2017/0472; A61B 2017/00464; A61B 2017/0053; A61B 2017/06057; A61B 17/06061; A61B 17/0625; A61B 2017/0046; A61B 2017/0477; A61B 2017/06042; A61B 2017/06142; A61B 2017/292; A61B 17/062; A61B 17/0491; A61B 2090/0811
See application file for complete search history.

(56) References Cited

U.S. PATENT DOCUMENTS

2015/0038800 A1* 2/2015 Prior et al.
2015/0282805 A1 10/2015 Sauer
2017/0172564 A1 6/2017 Sauer

* cited by examiner

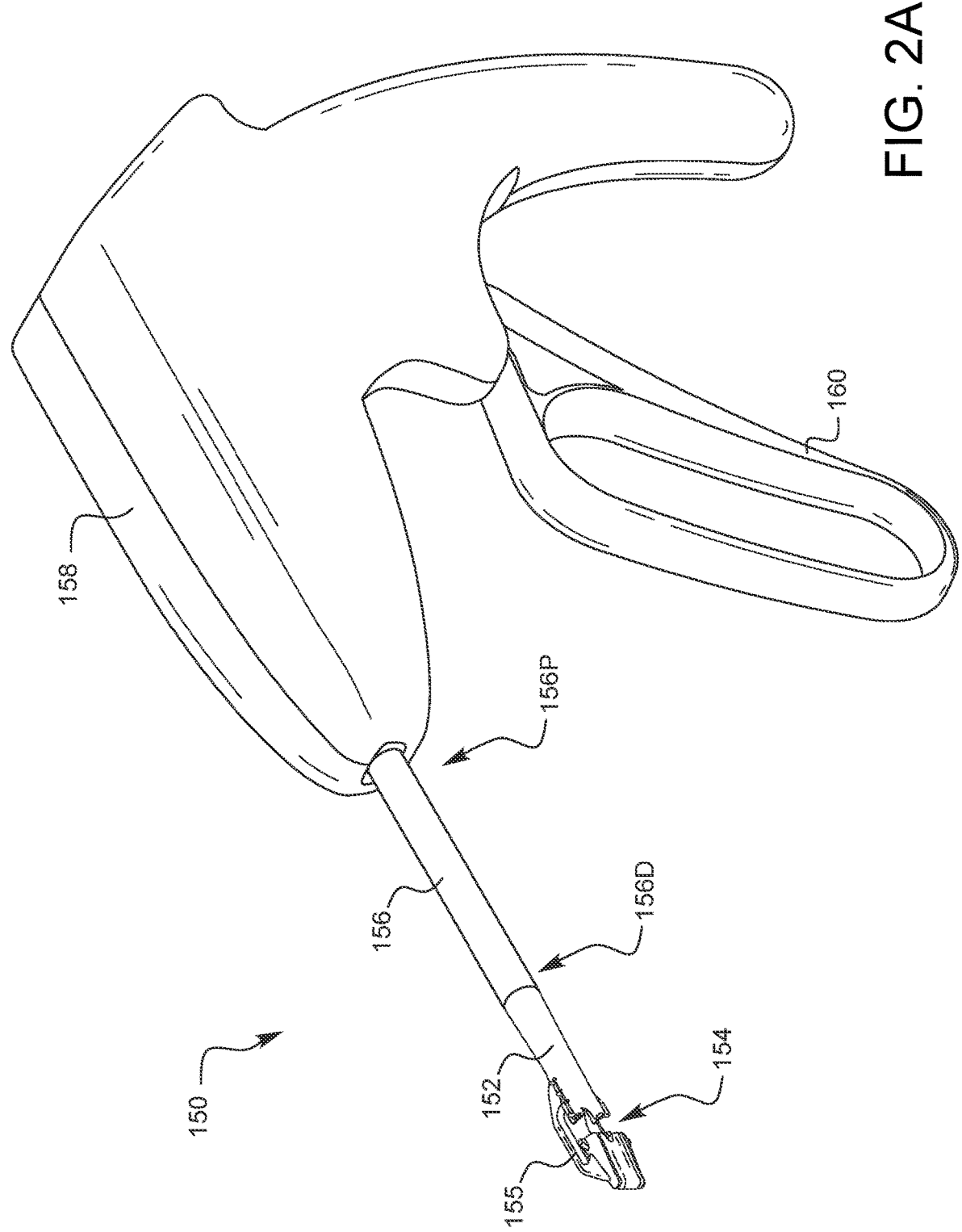

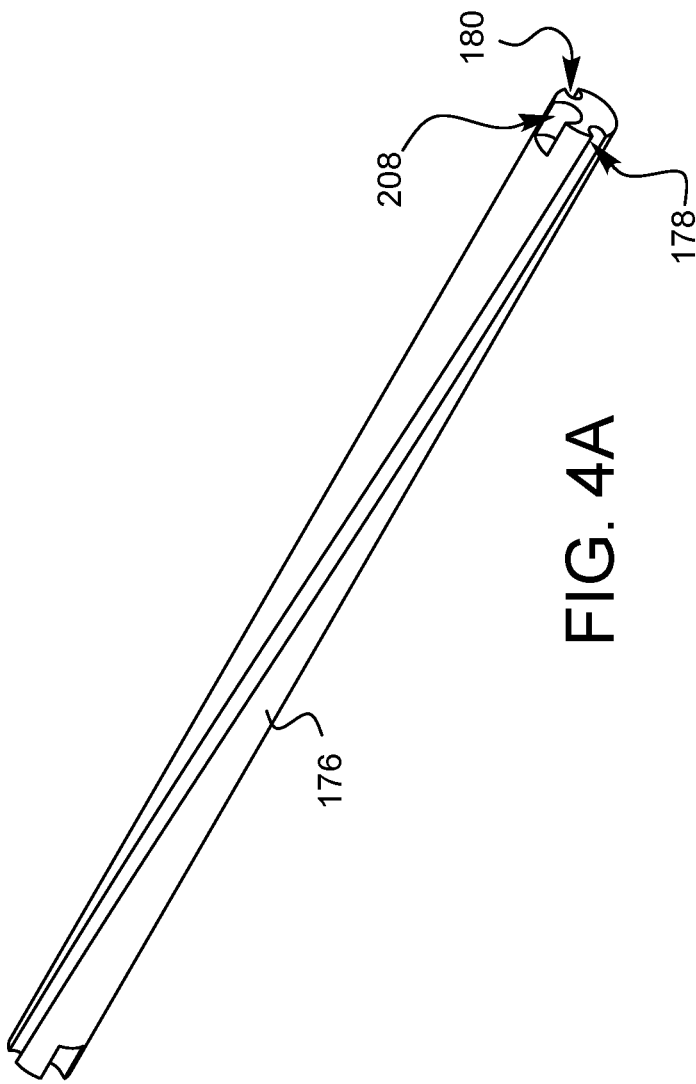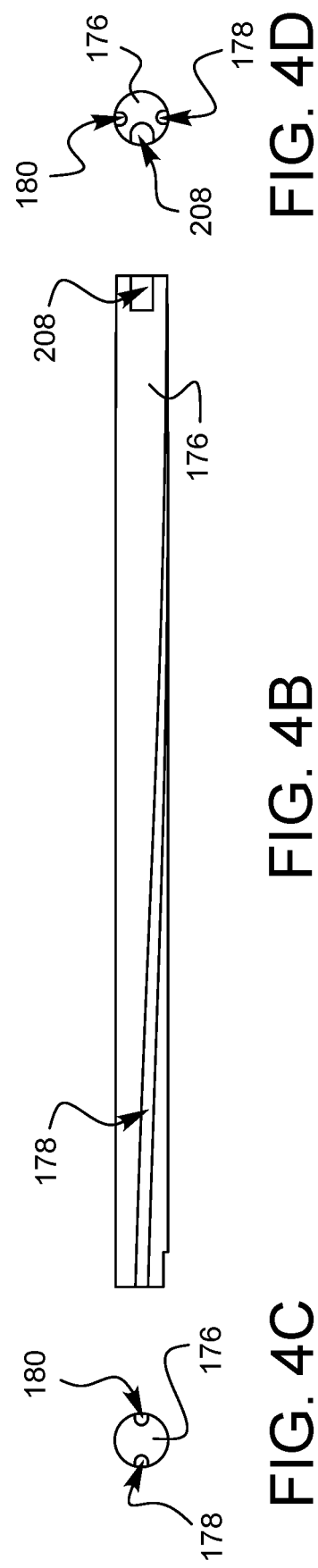

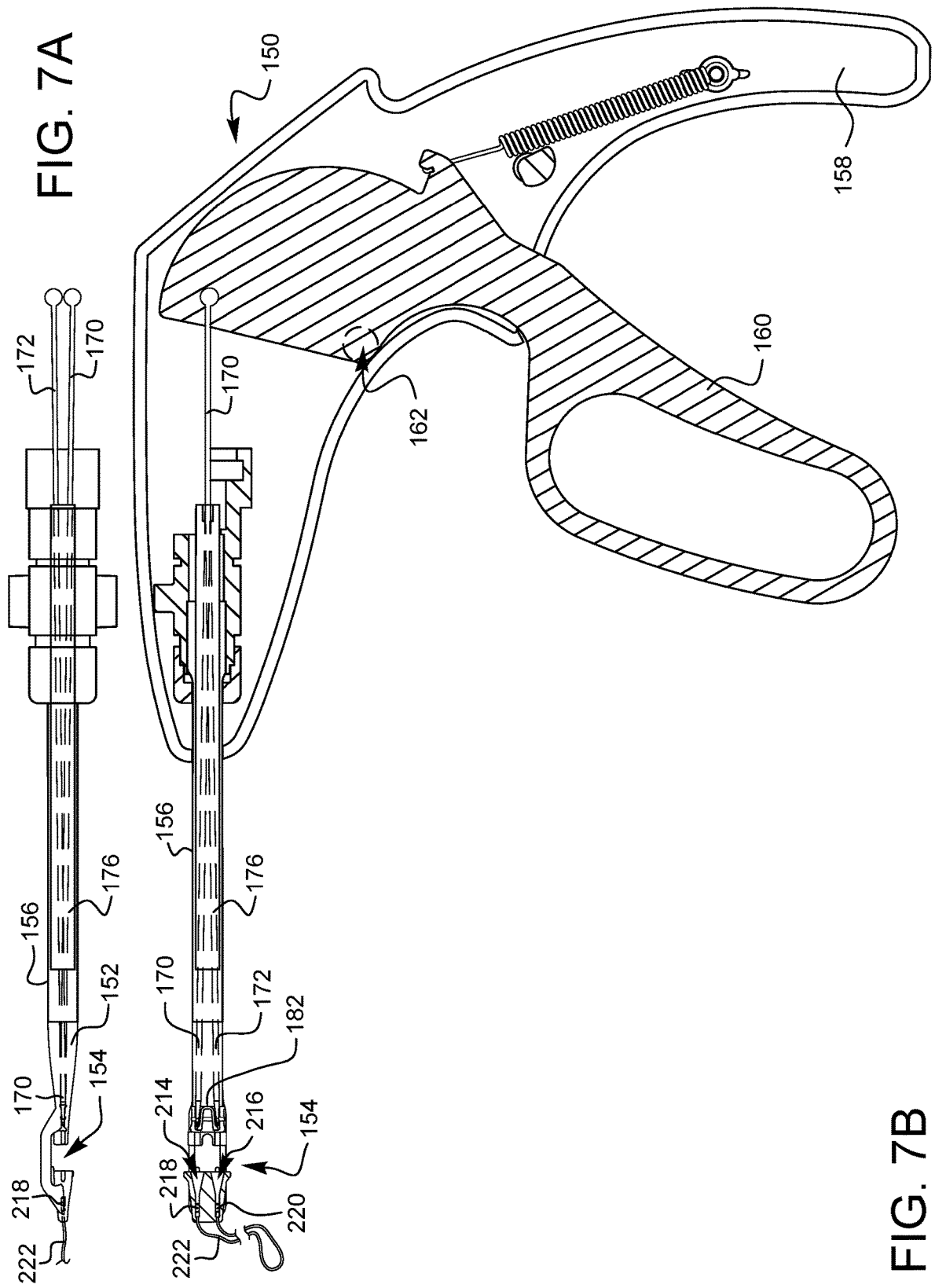

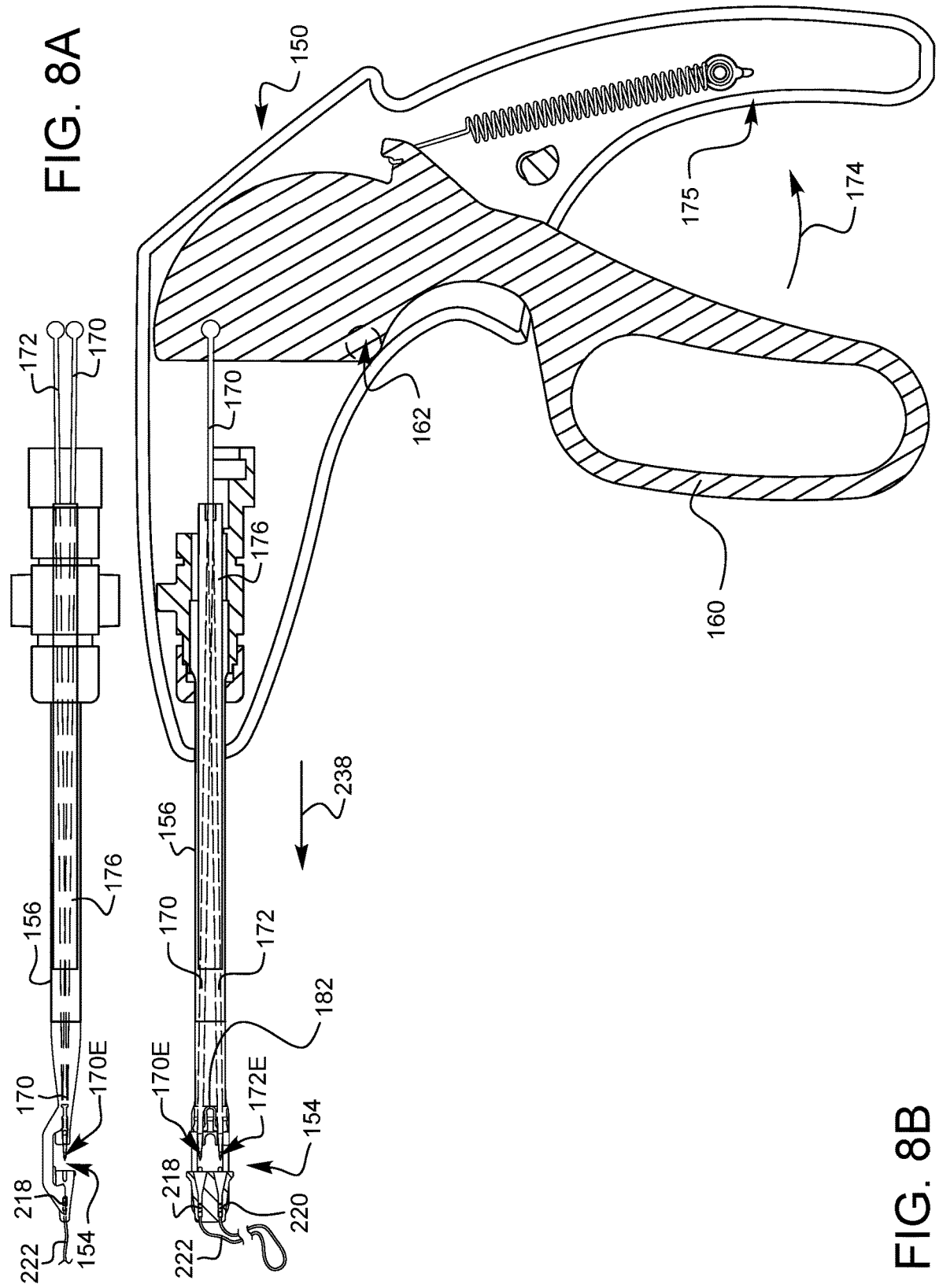

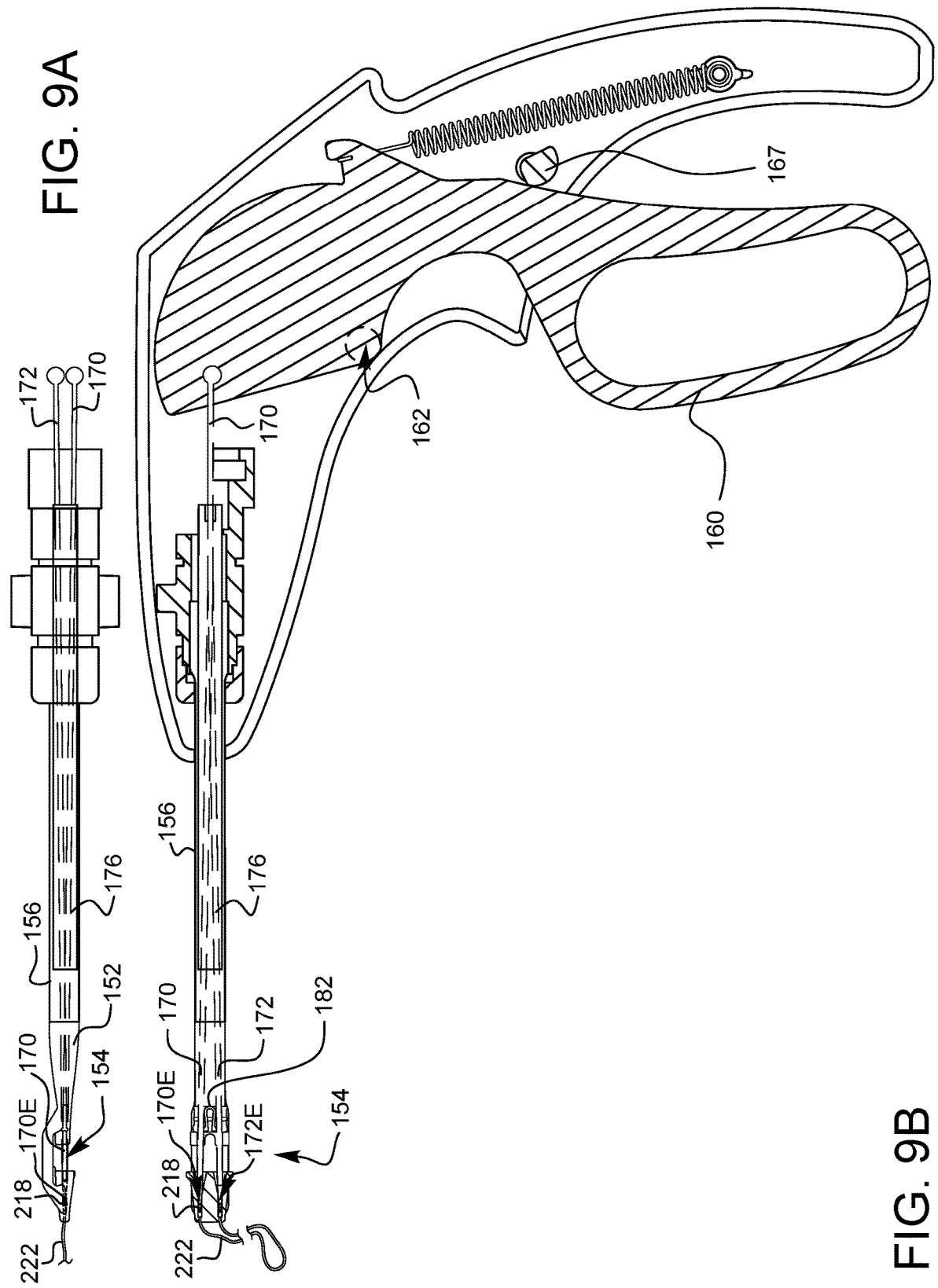

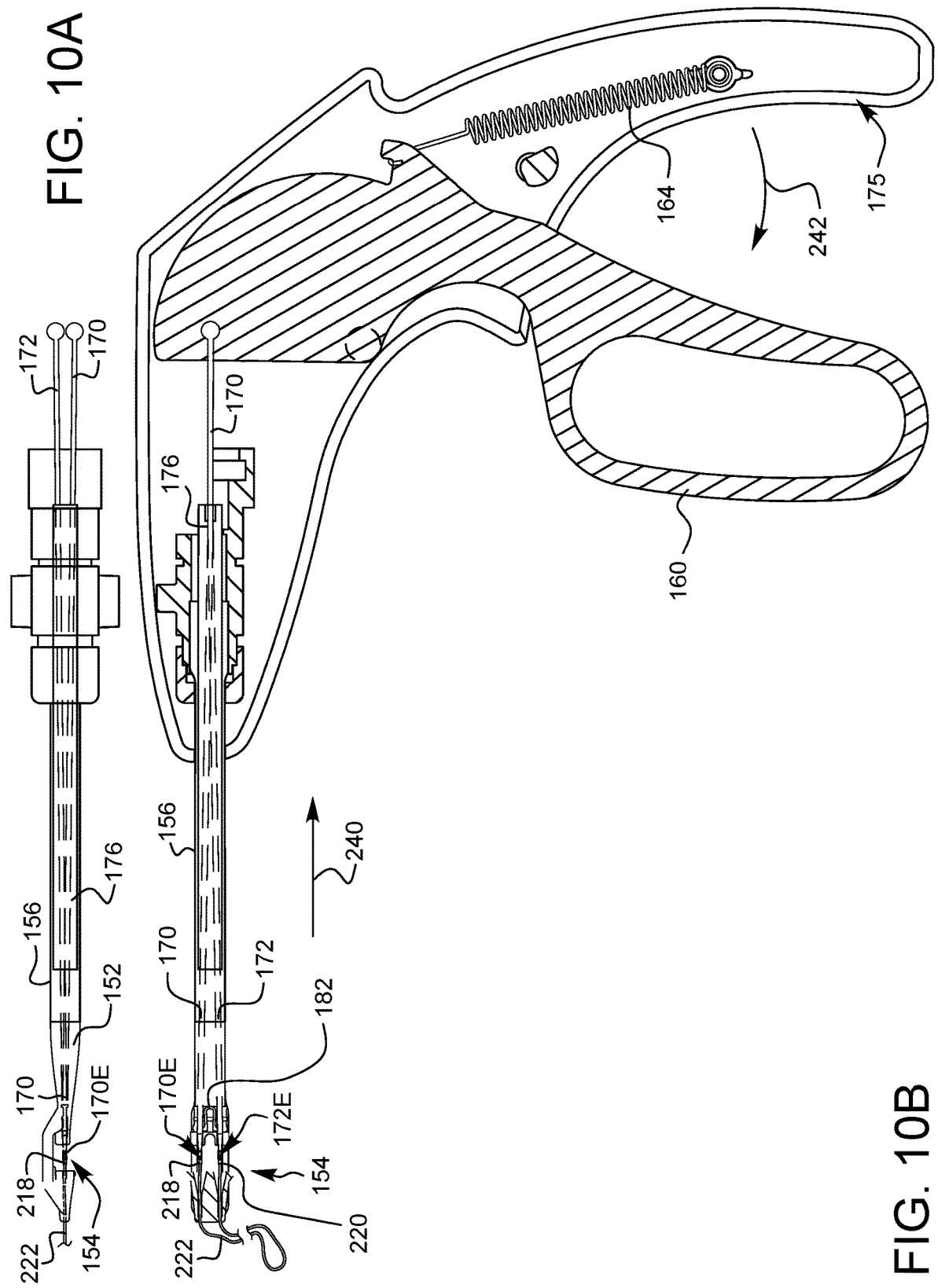

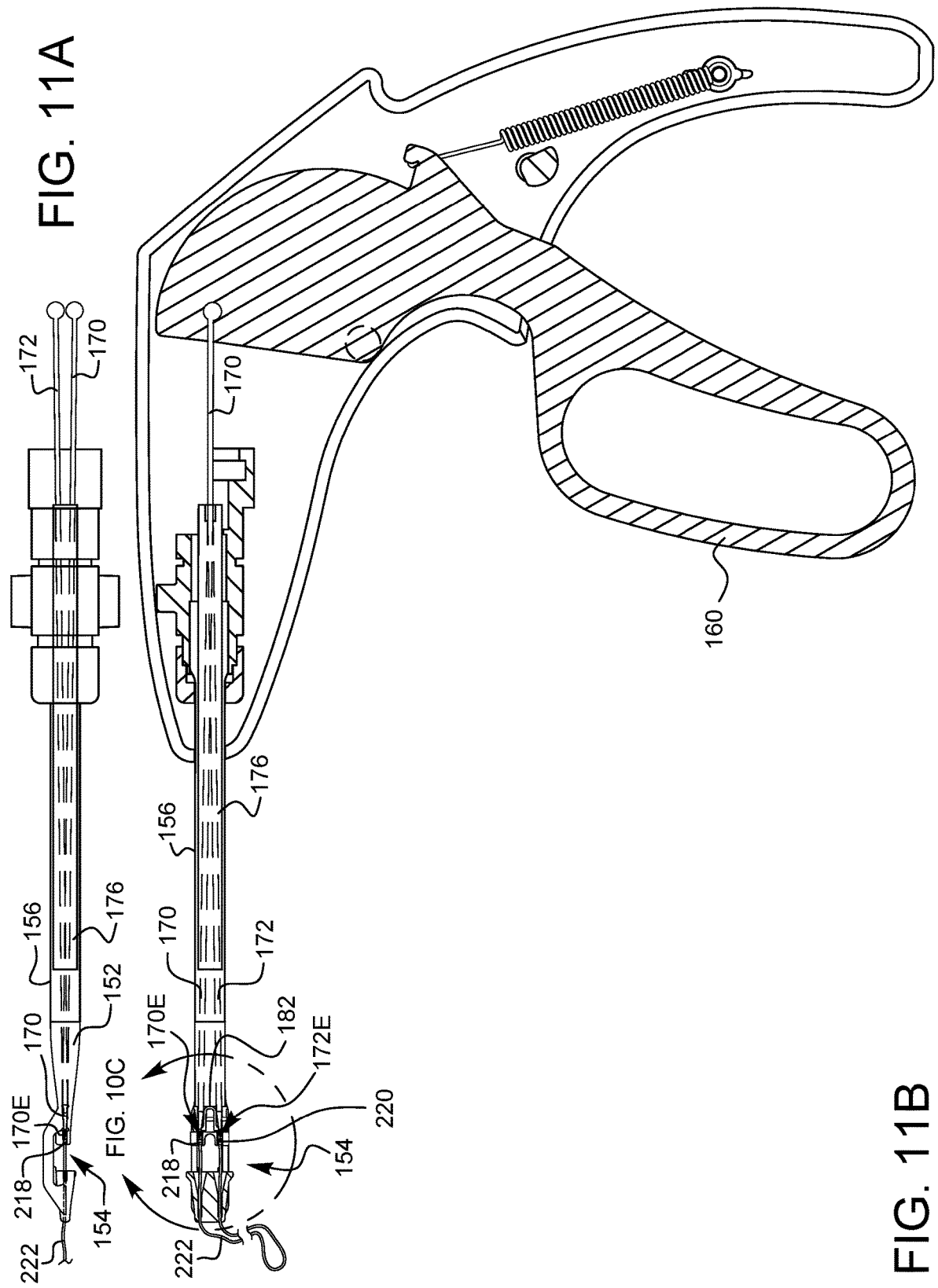

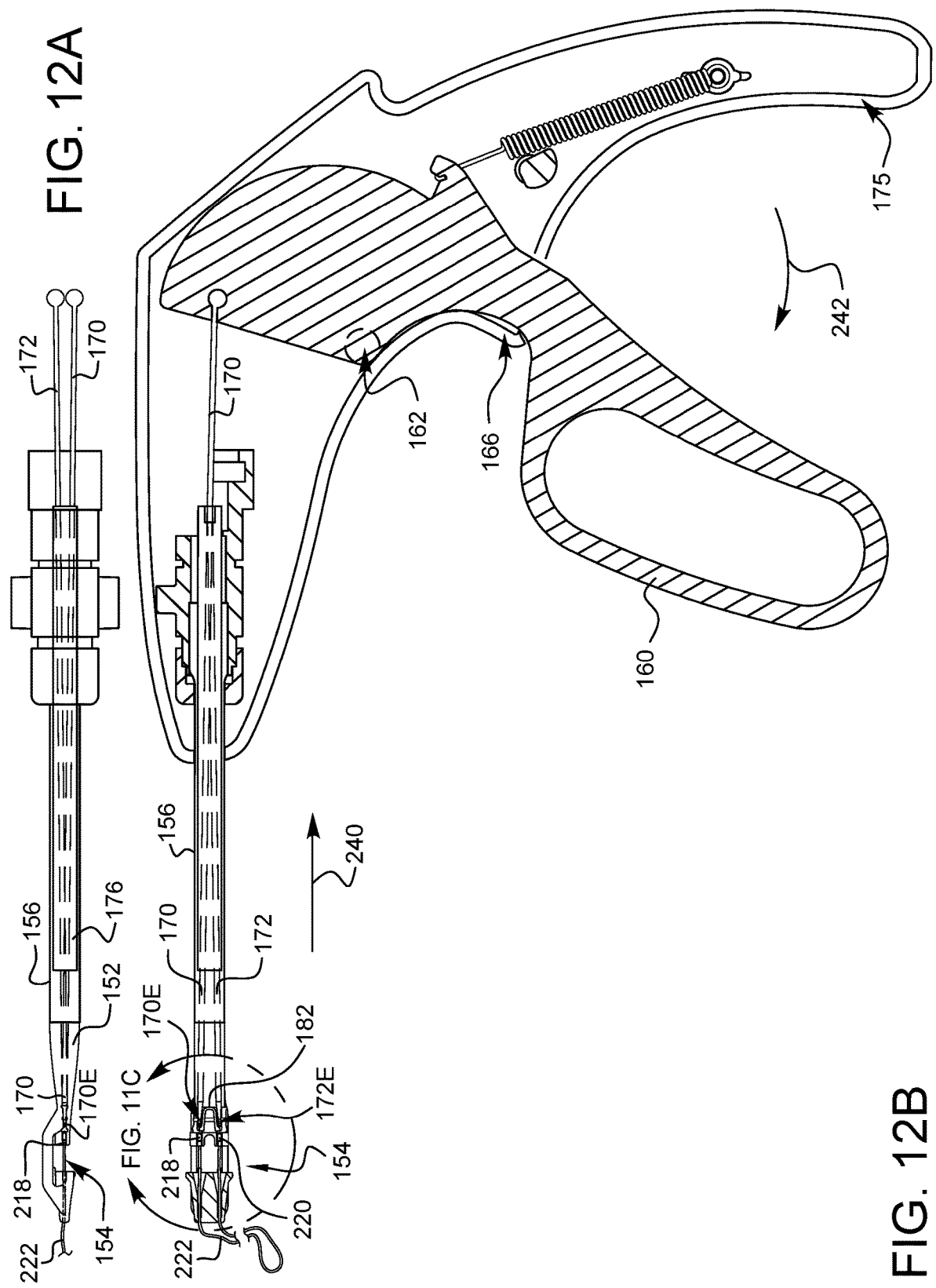

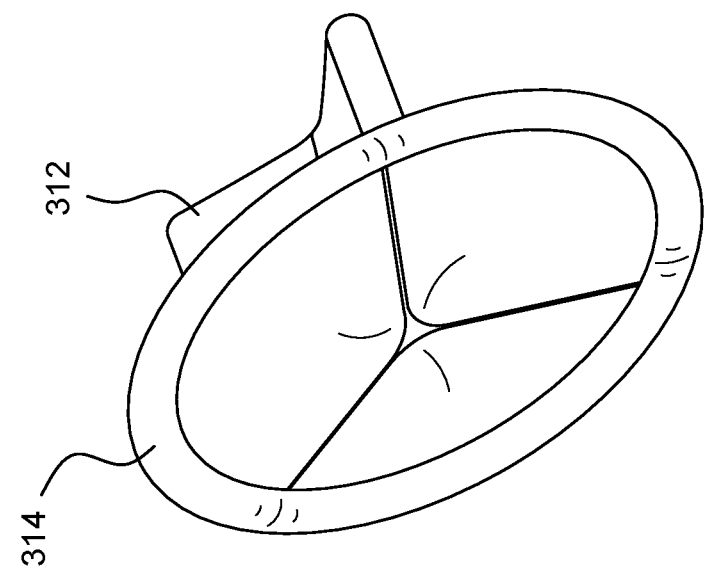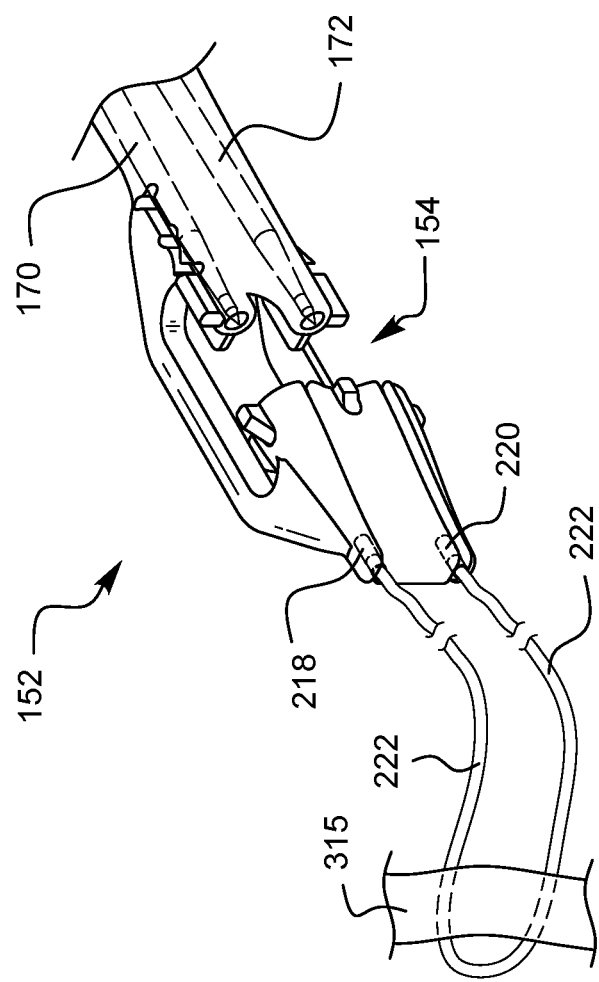
FIG. 19A

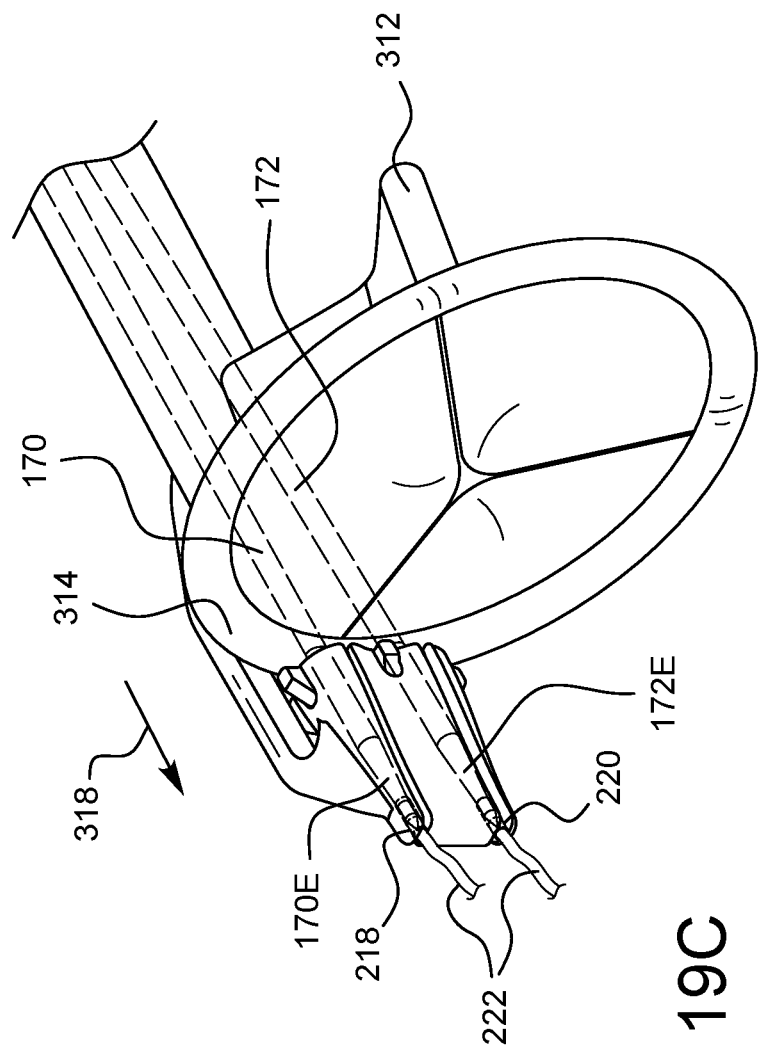

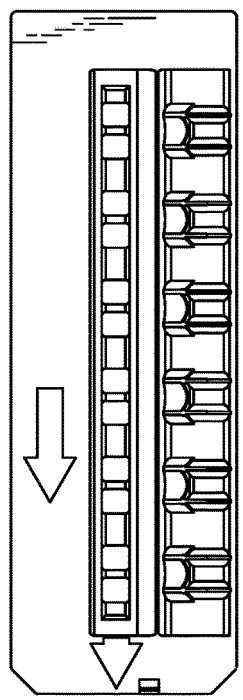
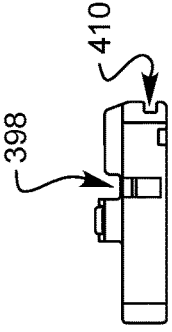
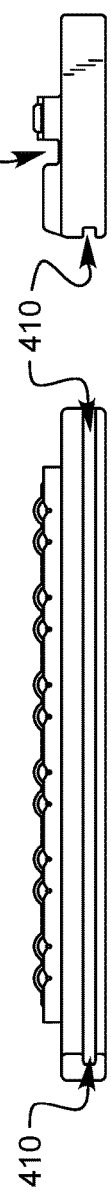
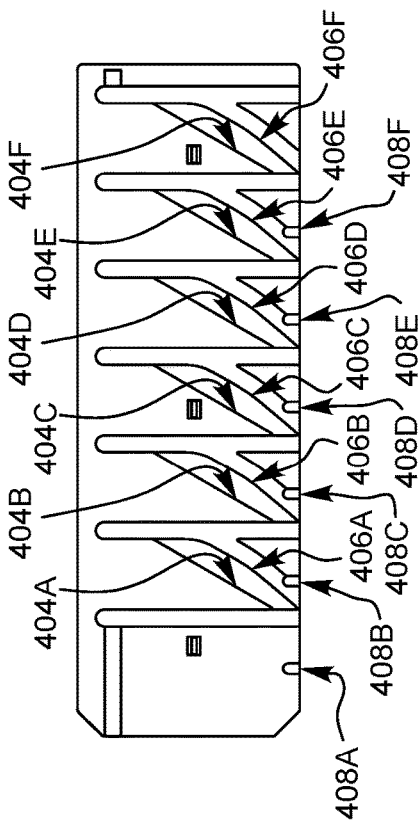

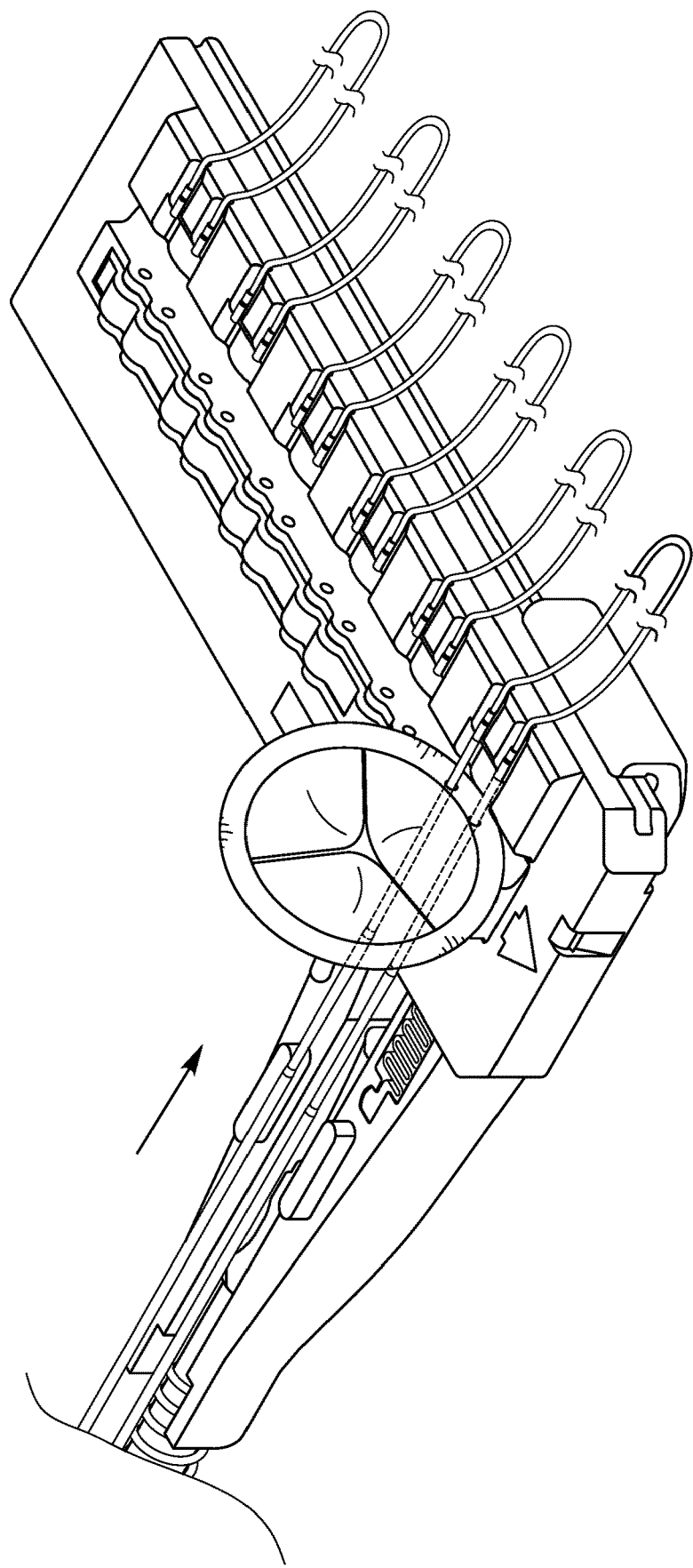

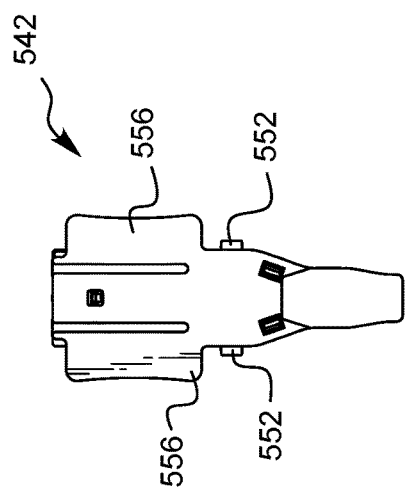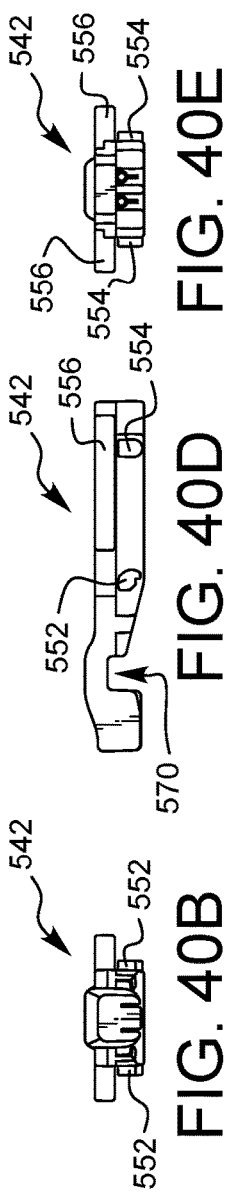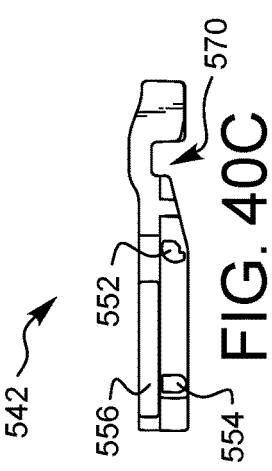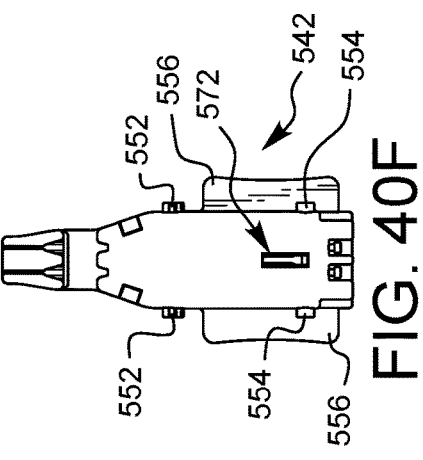
FIG. 40A FIG. 40B FIG. 40C FIG. 40D FIG. 40E FIG. 40F

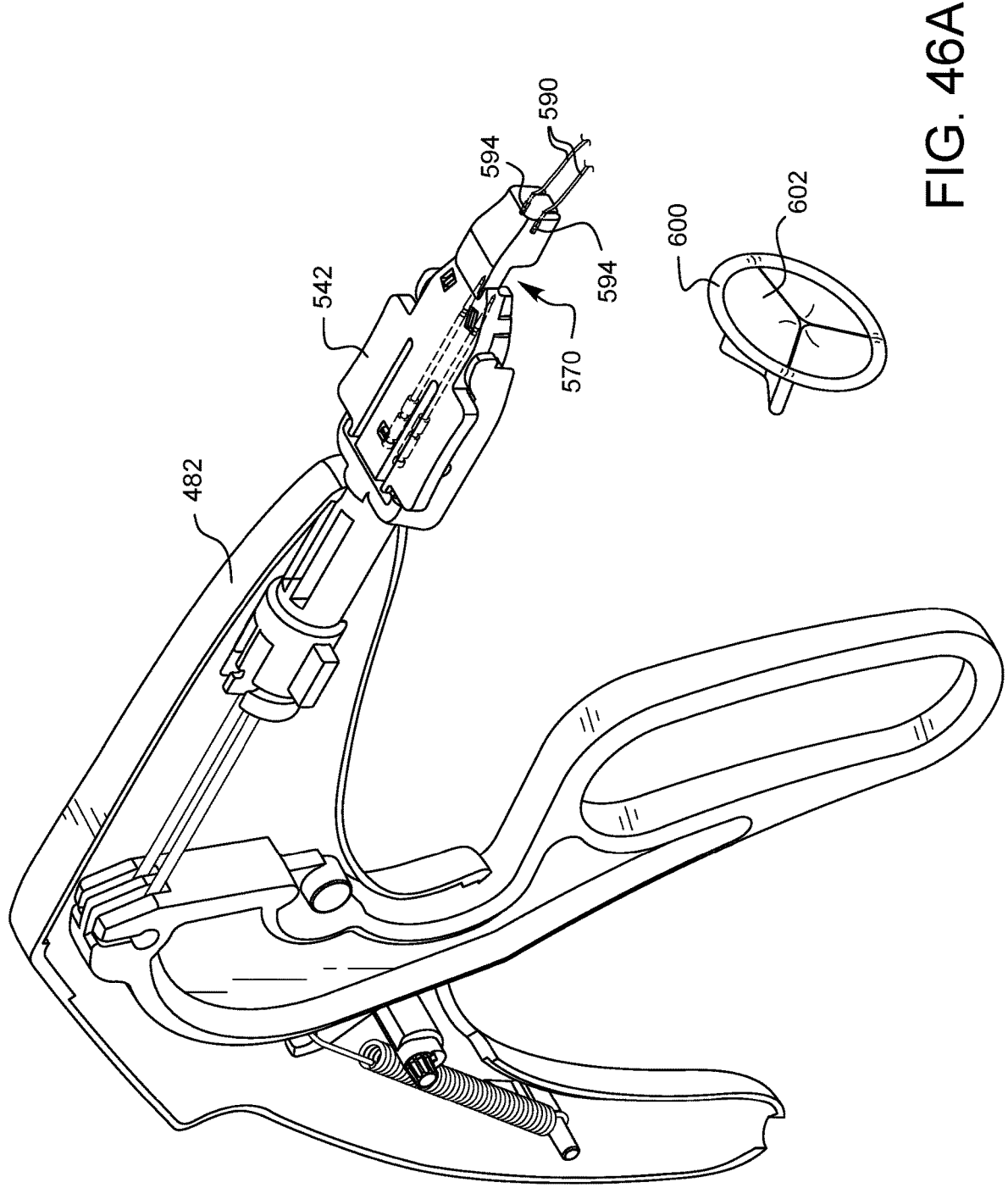

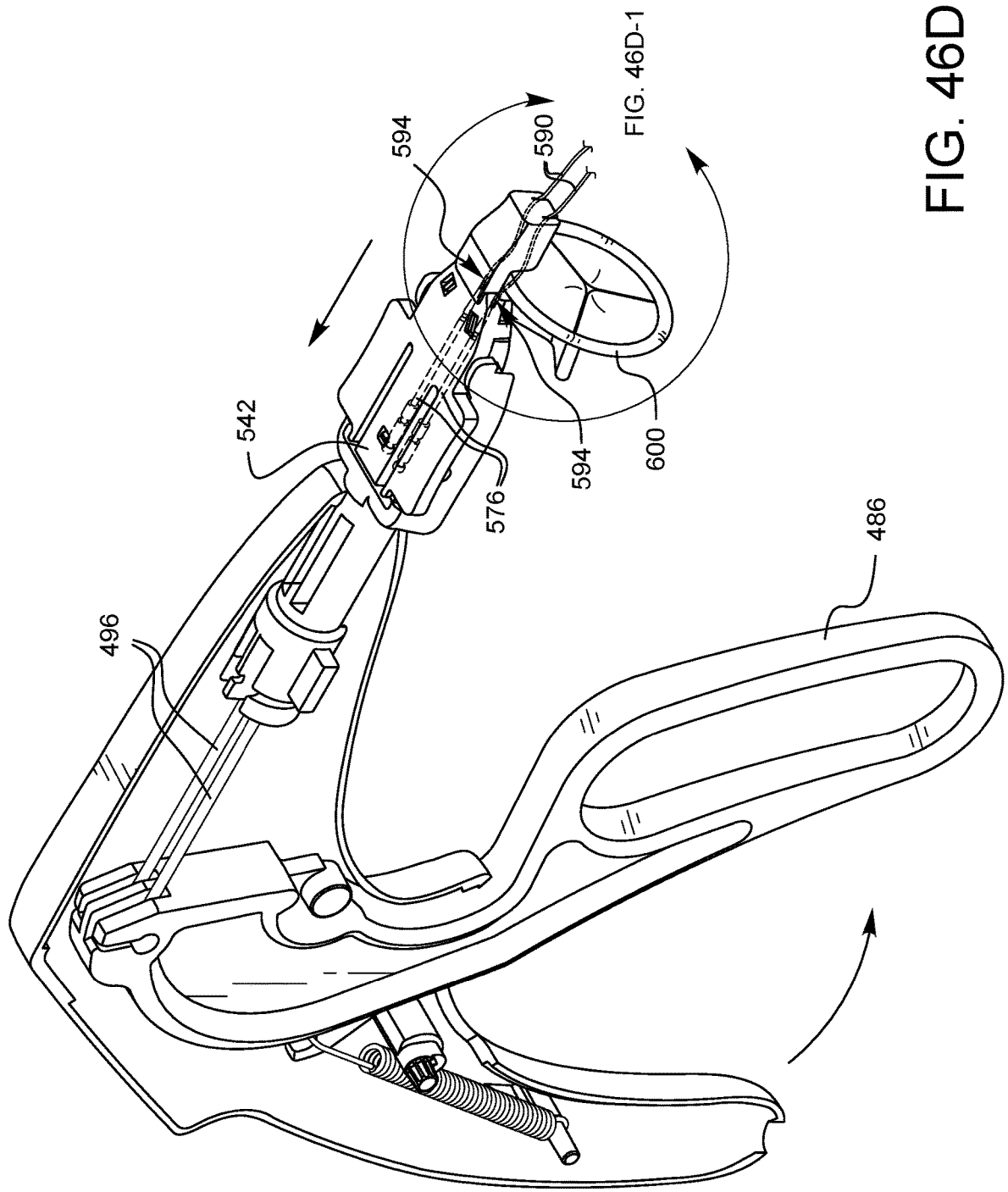

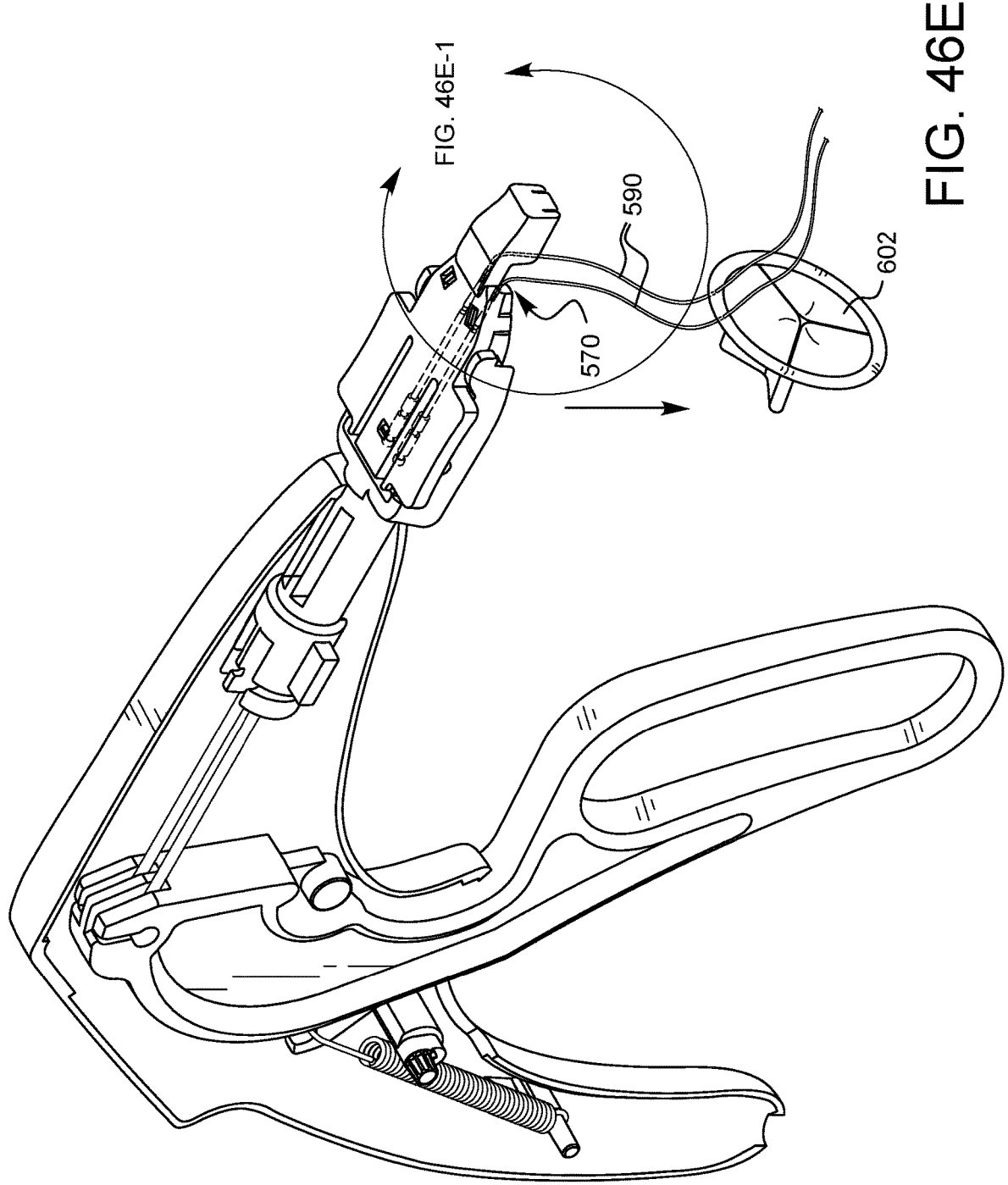

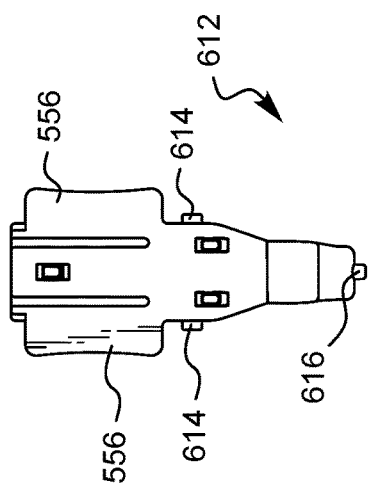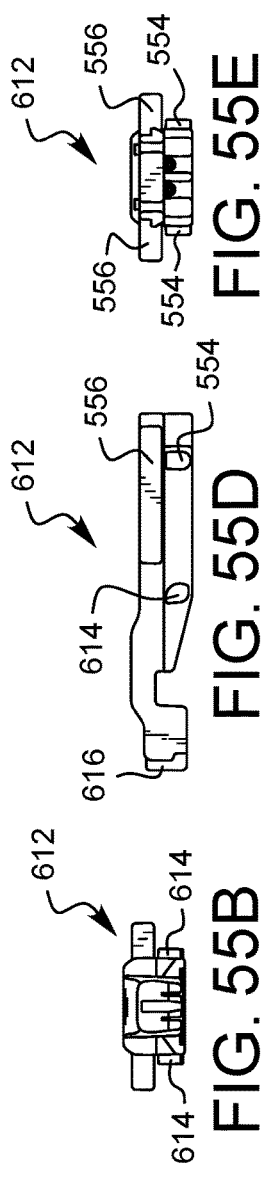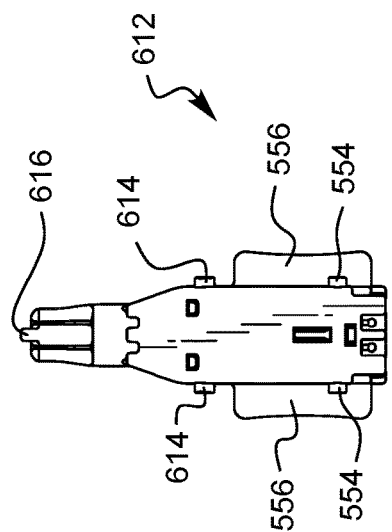

PROSTHETIC SUTURING DEVICE AND METHODS THEREOF

RELATED APPLICATIONS

This application is a 35 U.S.C. 371 national stage application of International PCT Application No. PCT/US2017/057057 filed Oct. 17, 2017, entitled "PROSTHETIC SUTURING DEVICE AND METHODS THEREOF". The PCT/US2017/057057 application claims priority to U.S. Provisional Patent Application No. 62/409,304 filed Oct. 17, 2016 and is entitled "PROSTHETIC SUTURING DEVICE AND METHODS THEREOF". The entire 62/409,304 and PCT/US2017/057057 applications are hereby incorporated by reference in their entirety.

FIELD

The claimed invention relates to surgical suturing devices, and more specifically to surgical suturing devices suitable for use with prosthetic devices, especially cardiac prosthetic devices such as replacement heart valves.

BACKGROUND

Modern advances in cardiac surgery have made it possible to replace heart valves using minimally invasive surgical techniques. As minimally invasive techniques have improved, surgeons are able to operate on patients through smaller and smaller access holes, resulting in less perioperative pain and shorter recovery times. A main focus of innovations in minimally invasive cardiac surgery has been on the tools which pass into the patient, through the small access holes, to place suture stitches more efficiently and reliably. By focusing on improvements to these steps of the surgical procedures, patients are able to be on cardio-pulmonary bypass machines for shorter times, thereby improving patient outcomes. Resultant efficiency improvements while working within the patient further help to reduce stress and fatigue on surgeons.

It would also be advantageous to focus on efficiency outside of the patient. Surgical teams are regularly working to streamline their own processes to enable surgeons to be as efficient as possible. In many minimally invasive surgical procedures, the ends of sutures which have been stitched within a patient are brought back out of the patient through one of the access sites so that the suture ends can be kept organized and then stitched through a sewing ring of a prosthetic device. Unfortunately, the suture ends often have adapters which were previously used to enable a corresponding minimally invasive suturing device to manipulate the suture ends within the patient. While it might be possible to reload the adapters (and therefore the suture ends) into the minimally invasive suturing device, such devices (meant for in-patient use and suturing tissue) are often not compatible with suturing a sewing cuff of a prosthetic device. As a result, surgical teams are forced to cut off the adapters and thread each suture onto a needle in order to manually stitch each suture end through a prosthetic valve's sewing cuff. For many cardiac surgical procedures, unfortunately, this can increase the overall time a patient is on cardio-pulmonary bypass (CPB). Longer CPB times are associated with complications of the inflammatory system, heart, lungs, kidneys, and brain. Therefore, it would be desirable to have a prosthetic suturing device that is compatible with one or more suture adapters which have been used with a minimally invasive surgical suturing device and which has features to increase the efficiency of a surgical team and reduce CPB time.

The human heart relies on a series of one-way valves to help control the flow of blood through the chambers of the heart. For example, referring to FIG. 1A, deoxygenated blood returns to the heart 20, via the superior vena cava 22 and the inferior vena cava 24, entering the right atrium 26. The heart muscle tissue contracts in a rhythmic, coordinated heartbeat, first with an atrial contraction which aids blood in the right atrium 26 to pass through the tricuspid valve 28 and into the right ventricle 30. Following atrial contraction, ventricular contraction occurs and the tricuspid valve 28 closes. Ventricular contraction is stronger than atrial contraction, assisting blood flow through the pulmonic valve 32, out of the heart 20 via the pulmonary artery 34, and to the lungs (not shown) for oxygenation. Following the ventricular contraction, the pulmonic valve 32 closes, preventing the backwards flow of blood from the pulmonary artery 34 into the heart 20.

Oxygenated blood returns to the heart 20, via the pulmonary veins 36, entering the left atrium 38. Left atrial contraction assists blood in the left atrium 38 to pass through the mitral valve 40 and into the left ventricle 42. Following the atrial contraction, ensuing ventricular contraction causes mitral valve 40 closure, and pushes oxygenated blood from the left ventricle 42 through the aortic valve 44 and into the aorta 46 where it then circulates throughout the body. Following left ventricular contraction, the aortic valve 44 closes, preventing the backwards flow of blood from the aorta 46 into the heart 20.

Unfortunately, one or more of a person's heart valves 28, 32, 40, and 44 can have or develop problems which adversely affect their function and, consequently, negatively impact the person's health. Generally, problems with heart valves can be organized into two categories: regurgitation and/or stenosis. Regurgitation occurs if a heart valve does not seal tightly, thereby allowing blood to flow back into a chamber rather than advancing through and out of the heart. This can cause the heart to work harder to remain an effective pump. Regurgitation is frequently observed when the mitral valve 40 prolapses (extends back) into the left atrium 38 during a ventricular contraction. Stenosis, by contrast, is when a heart valve does not fully patent due to stiff or fused leaflets, blood flow tract narrowing, or obstructive material buildup (e.g., calcium). The resultant narrowed outflow causes the heart to work harder to pump blood through it, possibly leading to heart failure.

Fortunately, advances in cardiac surgery, and in particular the evolution of reliable cardio-pulmonary bypass (CPB), have enabled open heart and less-invasive methods for heart valve replacement. During CPB, deoxygenated blood is diverted from the superior vena cava 22 and inferior vena cava 24 in or near the right atrium 26 of the heart 20, brought outside the body to a CPB machine, reoxygenated, and returned to the body at the aorta 46, or other great arterial vessels, thereby bypassing the heart 20 and making it possible to stop the heart 20 for cardiac surgery.

Unfortunately, while such cardiac procedures have become common-place, they are not without risks. In particular, extended time on a CPB machine can increase a patient's chances of developing complications involving the inflammatory system, heart, lungs, kidneys, brain, etc. An inflammatory response can be triggered by blood coming into contact with the foreign substances of the tubing leading to the CPB machine and the components of the machine itself. These types of inflammatory responses can damage the endothelium (inner layer of cells) of blood vessels, making them more susceptible to platelet and clot adhesion, and ultimately to an increased chance of atherosclerosis and other cardiovascular complications. Additionally, aortic clamping, necessary to establish the CPB, may cause inadequate blood flow to certain organs, for example, the heart, lungs, kidneys, or brain, thereby leading to possible ischemic damage to those organs. The risks of complications due to CPB increase dramatically with the amount of time a patient is actively connected to the CPB machine. Accordingly, surgeons rely on a combination of specialized skills, knowledge, technologies, and teamwork to operate as efficiently as possible in order to minimize a patient's time on CPB.

Depending on the number of valves being replaced for a patient, a typical heart valve replacement surgery can last between two to six hours, one to two hours of which can be spent on a CPB machine. While the patient is on CPB, the surgeon must gain access to the heart valve, remove the pathologic valve tissue as necessary, and install a replacement valve at the location of the original valve. The valve installation process, typically requiring suture placement and fastening, can be very time consuming, especially when surgeons are operating through small access sites when employing less-invasive techniques to reduce surgical trauma. Furthermore, a large number of sutures and their loose ends must be effectively managed to track which suture ends go together and ensure the sutures do not get tangled. As an example, FIG. 1B schematically illustrates a surgical situation during a minimally invasive aortic valve replacement. The defective valve tissue has been removed and multiple sutures 48 have been placed into the tissue of the aortic root. These sutures 48 must be managed and sewn through a sewing cuff of a replacement valve 50 before the valve 50 is slid down the suture lines and into the aortic root where the suture ends will be secured to anchor the heart valve 50. The suture management and the sewing into the cuff can be very time consuming. Therefore, there is a need for devices and methods which enable surgeons to operate more efficiently during surgery to replace pathologic anatomical structures, such as, but not limited to, replacement heart valves. Such devices and methods can reduce the amount of time patients need to be attached to a CPB machine, thereby reducing the likelihood of CPB-related side effects. Faster cardiac operations offer additional benefits, such as reduced surgical team fatigue and more efficient use of critical resources. Expediting cardiac surgery can also improve patient outcomes.

BRIEF DESCRIPTION OF THE DRAWINGS

FIG. 2A is a perspective view of one embodiment of a prosthetic suturing device.

FIG. 4A is an enlarged perspective view of one embodiment of a needle guide tube for a prosthetic suturing device.

FIGS. 4B, 4C, and 4D are side, back, and front elevational views, respectively, of the needle guide tube of FIG. 4A.

FIG. 7B is a partially cross-sectioned side view of the prosthetic suturing device of FIG. 2B with the needles in a retracted position.

FIG. 7A is a top view of the device from FIG. 7B, hiding the handle, housing, spring, and hard stop in order to more clearly show the proximal needle orientation.

FIG. 8B is a partially cross-sectioned side view of the prosthetic suturing device of FIG. 2B, with the needles in a partially engaged position as they pass through the cuff-receiving area.

FIG. 8A is a top view of the device from FIG. 8B, hiding the handle, housing, spring, and hard stop in order to more clearly shown the proximal needle orientation.

FIG. 9B is a partially cross-sectioned side view of the prosthetic suturing device of FIG. 2B, with the needles in a fully engaged position and coupled to the suture ferrules held in the distal end of the guide tip.

FIG. 9A is a top view of the device from FIG. 9B, hiding the handle, housing, spring, and hard stop in order to more clearly show the proximal needle orientation.

FIG. 10B is a partially cross-sectioned side view of the prosthetic suturing device of FIG. 2B, with the needles partially retracted and pulling the suture ferrules and suture back through the cuff receiving area.

FIG. 10A is a top view of the device from FIG. 10B, hiding the handle, housing, spring, and hard stop in order to more clearly show the proximal needle orientation.

FIG. 11B is a partially cross-sectioned side view of the prosthetic suturing device of FIG. 2B, with the needles fully retracted.

FIG. 11A is a top view of the device from FIG. 11B, hiding the handle, housing, spring, and hard stop in order to more clearly show the proximal needle orientation.

FIG. 12B is a partially cross-sectioned side view of the prosthetic suturing device of FIG. 2B, with the needles hyper-retracted.

FIG. 12A is a top view of the device from FIG. 12B, hiding the handle, housing, spring, and hard stop in order to more clearly show the proximal needle orientation.

FIGS. 19A-19F illustrate one example of a surgical usage of an embodiment of a prosthetic suturing device.

FIGS. 23A-23F show top, front, left, right, bottom, and rear (upside-down) elevational views, respectively, of the magazine of FIG. 22.

FIGS. 27A-27G are perspective views of the surgical suturing device and magazine of FIG. 20A being used to place a suture stitch in a sewing cuff of a replacement heart valve.

FIGS. 40A, 40B, 40C, 40D, 40E, and 40F are top, front, left, right, back, and bottom views of the cassette of FIG. 38A.

FIG. 41B-1 is an enlarged view of the distal end of the cassette from FIG. 41B showing the ferrules installed in the cassette.

FIG. 44B-1 is an enlarged view of the cassette and cassette receiver of FIG. 44B.

FIGS. 46A-46G illustrate how the surgical suturing device, with its installed cassette, may be used to place a suture stitch in a sewing cuff of a replacement heart valve.

FIGS. 55A, 55B, 55C, 55D, 55E, and 55F are top, front, left, right, back, and bottom views of the cassette of FIG. 53A.

Figure 1A:
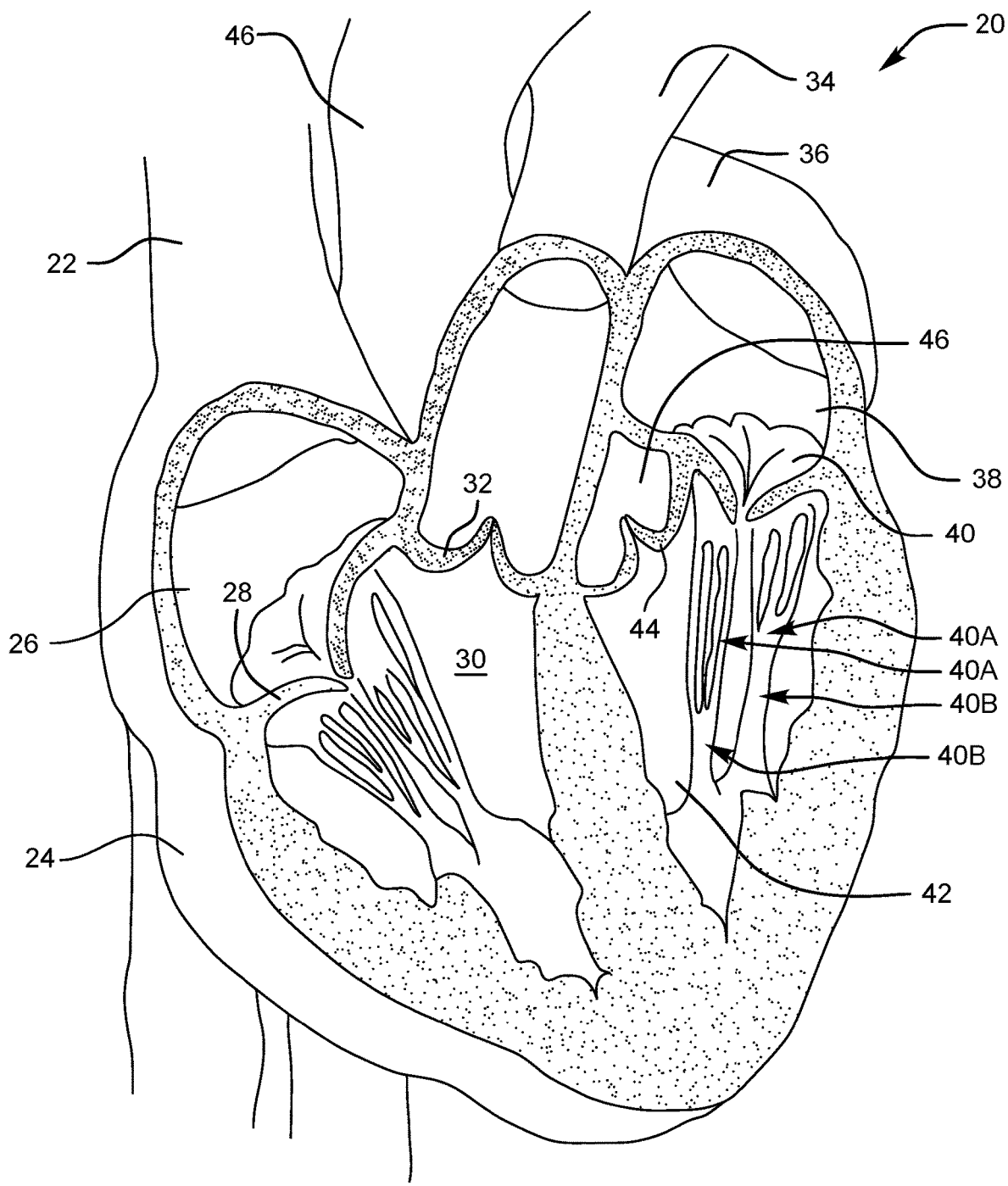
FIG. 1A is a sectional view of a heart.
Figure 1B:
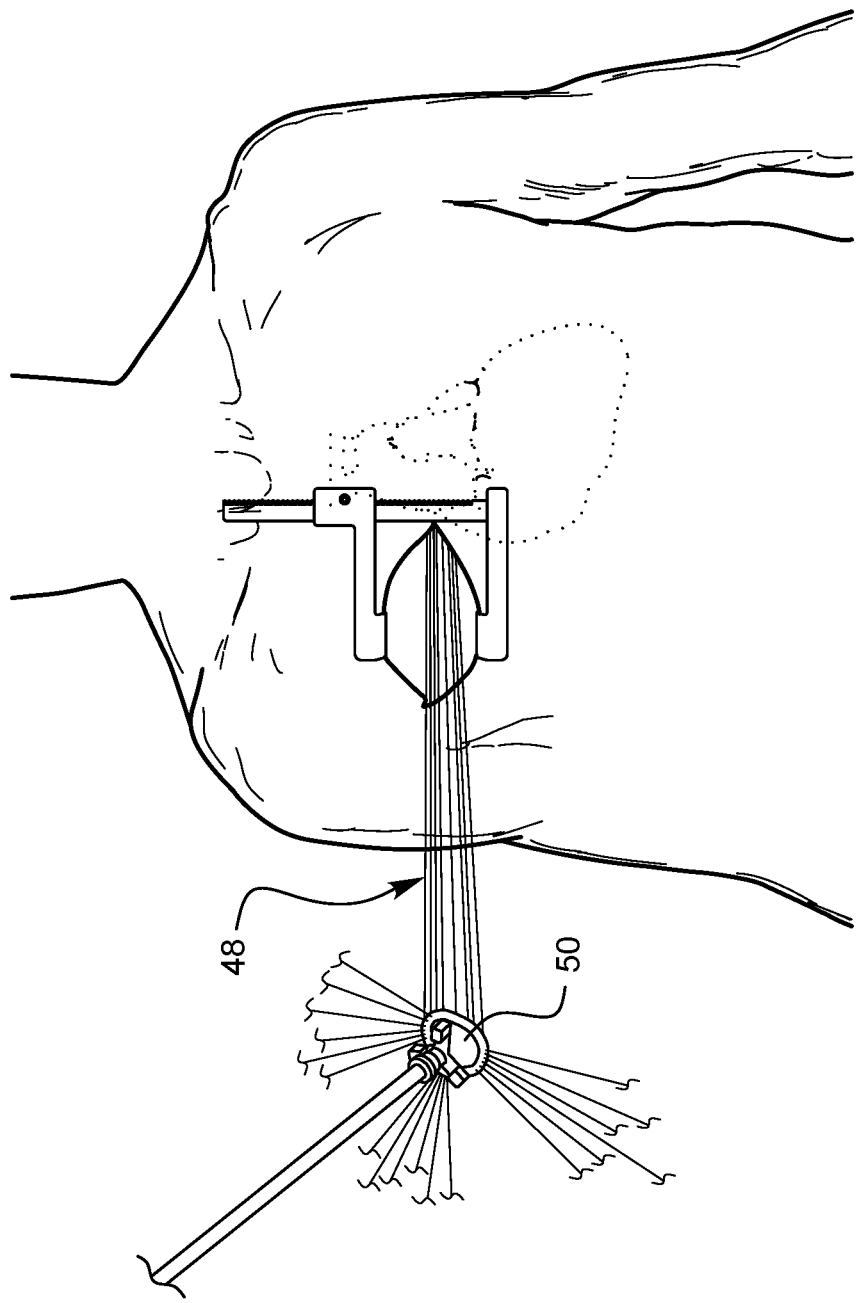
FIG. 1B schematically illustrates a surgical situation during a minimally invasive aortic valve replacement.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 2B:
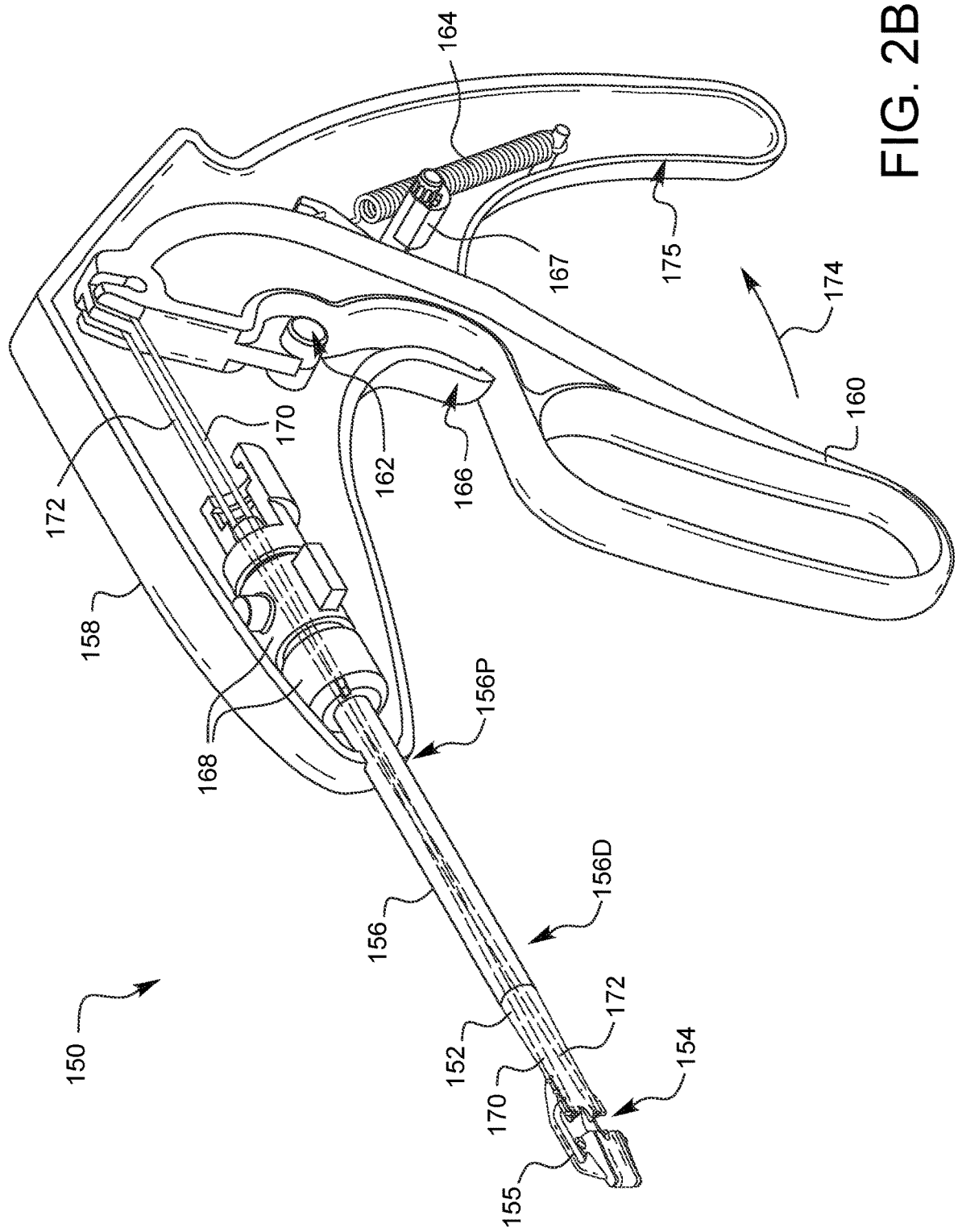
FIG. 2B is a partially exposed perspective view of the prosthetic suturing device of FIG. 1A with a portion of the housing removed.

FIG. 2A is a perspective view of one embodiment of a prosthetic suturing device 150. FIG. 2B is a partially exposed perspective view of the prosthetic suturing device 150 of FIG. 2A with a portion of the housing 158 removed. The prosthetic suturing device 150 has a guide tip 152 that defines a cuff receiving area 154. The cuff receiving area 154 is configured to receive a portion of a sewing cuff of a replacement anatomical structure. The guide tip 152 further includes a cuff support 155 configured to align at least a portion of a sewing cuff for a replacement anatomical structure within the cuff receiving area 154. Examples of a replacement anatomical structure may include, but are not limited to, synthetic replacement heart valves and natural tissue replacement heart valves. The sewing cuff on such a replacement anatomical structure is designed to be sewn with suture against one or more tissue sites inside a patient so that the replacement anatomical structure is held in a desired location. It should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures. Furthermore, for convenience, this specification will often utilize the example of a sewing cuff on a replacement heart valve, however, it should be understood that other types of replacement anatomical structures are contemplated as well. Such replacement anatomical structures having sewing cuffs are known to those skilled in the art.

The guide tip 152 is coupled to a shaft 156 at a distal end 156D of the shaft 156. The prosthetic suturing device also has a housing 158 to which a handle 160 is pivotably coupled at pivot point 162. The handle 160 is biased by spring 164 towards a handle stop 166 which is formed from part of the housing 158. A hard stop 167 is also located in the housing 158, in order to limit the travel of the handle 160 when squeezed in a direction 174.

Shaft holders 168 couple a proximal end 156P of the shaft 156 to the housing 158. First and second needles 170, 172 are in horizontal alignment where they are coupled to the handle 160 within the housing 158. In this embodiment, the needles 170, 172 are routed by a needle guide tube (not visible in this view) so as to be in vertical alignment near the cuff-receiving area 154. Movement 174 of the portion of the handle 160 outside of the housing 158 towards the grip 175 of the housing 158 will move the needles 170, 172 across the cuff receiving area 154. Since the grip 175 is part of the housing 158, portions of this specification may indicate that certain components are coupled to the grip 175, which is accurate because the grip is part of the housing.

Figure 3:
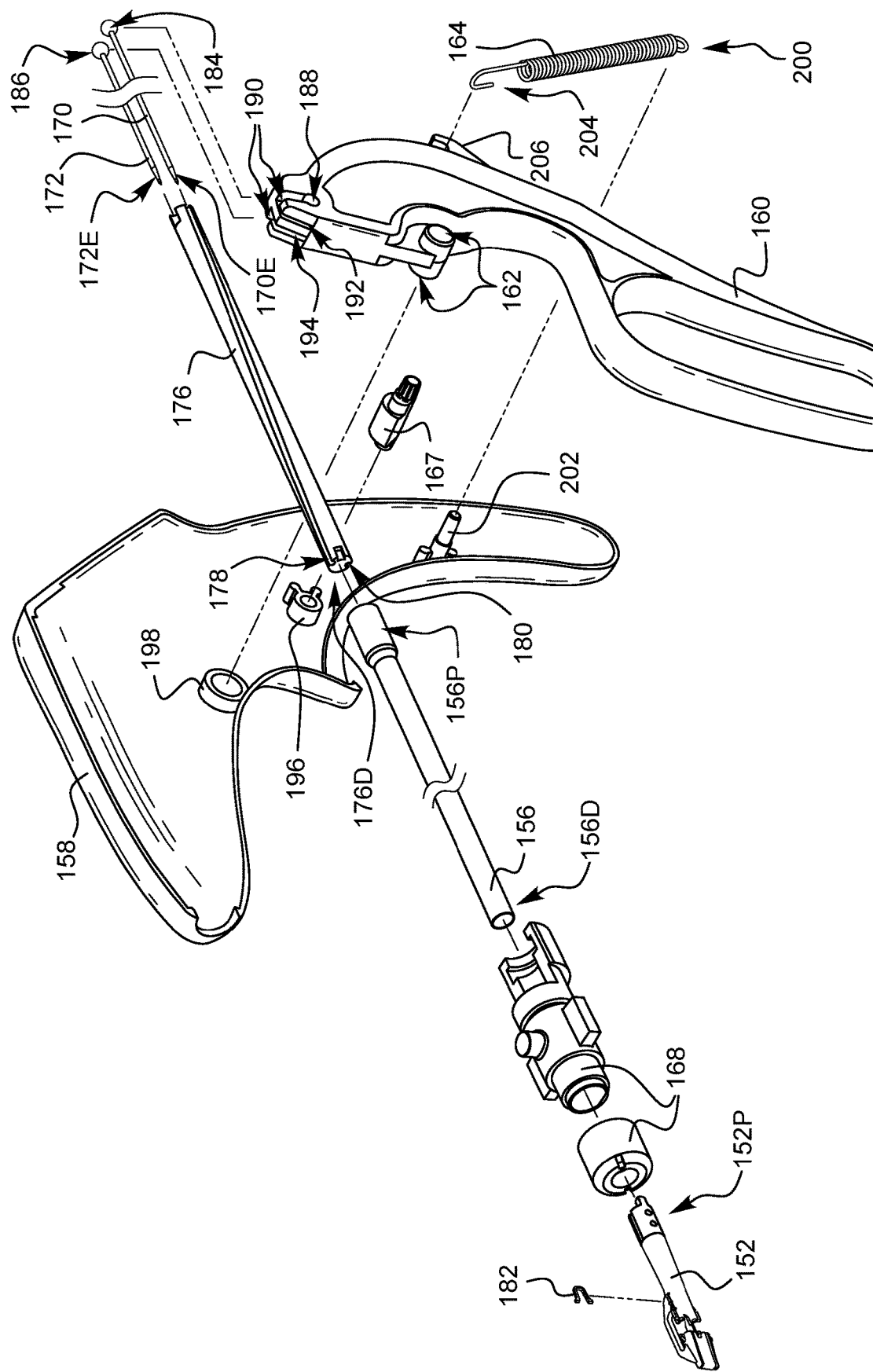
FIG. 3 is an exploded perspective view of the prosthetic suturing device of FIG. 2B.

FIG. 3 is an exploded perspective view of the prosthetic suturing device of FIG. 2B. The distal ends 170E, 172E of the first and second needles 170, 172 are each configured to engage a suture adapter (not shown here, but will be discussed later). A needle guide tube 176 having first and second spiral tracks 178, 180 is inserted into the proximal end 156P of the shaft 156, and shaft holders 168 are placed over the distal end 156D of the shaft 156 and coupled to the proximal end 156P of the shaft. The distal end 156D of the shaft 156 is coupled to the guide tip 152. A distal end 176D of the needle guide tube 176 abuts or lies close to a proximal portion 152P of the guide tip 152 inside a distal end 156D of the shaft 156. Starting with the needle ends 170E, 172E, the first and second needles 170, 172 are inserted into the first and second spiral tracks 178, 180 of the needle guide tube 176 as will be discussed below. The spiral tracks 178, 180 take the needles 170, 172 from a horizontal orientation to a vertical orientation at the proximal end of the device.

In the vertical orientation of the needles at the proximal end of the device, the second needle 172 will be located below the first needle 170. Before the first needle 170 is fully inserted, a ferrule release spring 182 may be inserted into a slot on the top of the guide tip 152 so that it rests against the second needle 172. Then, the first needle 170 can be fully inserted, compressing the ferrule release spring 182 between the two needles 170, 172.

A first ball end 184 is located on the proximal end of the first needle 170. Similarly, a second ball end 186 is located on the proximal end of the second needle 172. The second and first ball ends 186, 184 may be inserted into a side opening 188 in the handle 160. A top needle slot 190 allows the needles 170, 172 to move into the handle 160, and then the needles 170, 172 can be pivoted down into forward slots 192, 194, respectively, also formed in the handle 160. This couples the needles 170, 172 to the handle 160. The forward slots 192, 194 maintain the horizontal needle spacing at the proximal end of the device.

The pivot point 162 of the handle 160 may be aligned in a pivot boss 198 formed in the housing 158. The shaft holders 168 may be held and supported by a variety of features on the inside of the housing 158. Such features are not illustrated for simplicity, but are well known to those skilled in the art. Although only one half of the housing 158 is shown in this exploded view, it should be understood that a complementary half of the housing is also present (though not shown) and would have similar boss features to allow pivoting of the handle 160 and bracing of the shaft holders 168.

The hard stop 167 may be mounted in a hard stop boss 196 to limit travel of the handle 160, while a lower end 200 of spring 164 may be coupled to a fixed spring attachment point 202 on the housing. An upper end 204 of the spring 164 may be hooked onto a handle spring attachment point 206.

FIG. 4A is an enlarged perspective view of one embodiment of a needle guide tube 176 for a prosthetic suturing device. FIGS. 4B, 4C, and 4D are side, back, and front elevational views, respectively, of the needle guide tube 176 of FIG. 4A. In this embodiment, the needle guide tube 176 has a first spiral track 178 and a second spiral track 180. Looking at the back view of FIG. 4C, it can be seen that the spiral tracks 178, 180 will receive the first and second needles (not shown in this view) in a horizontal alignment from a proximal end of the device. Looking at the front view of FIG. 4D, it can be seen that the spiral tracks 178, 180 will have guided the needles into a vertical alignment near the guide tip (not shown in this view). The spiral tracks 178, 180 can provide support for a thinner needle so that the needles do not buckle when rotated to a different orientation. The needle guide tube 176 may also have a keyed portion 208 for mating with and/or aligning with a corresponding feature on the guide tip to ensure the needles exit the needle guide tube 176 and pass smoothly into the guide tip 152.

Figure 5:
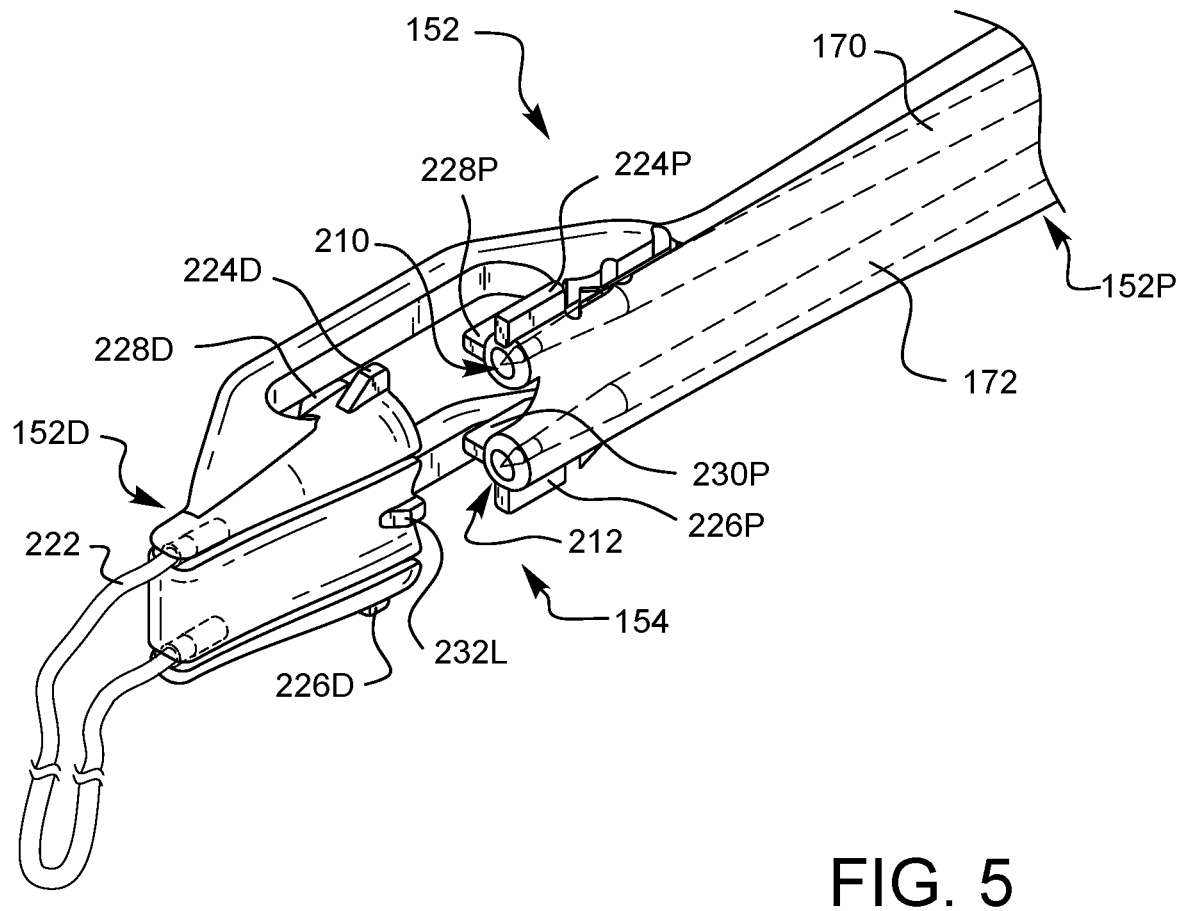
FIG. 5 is an enlarged perspective view of one embodiment of a guide tip for a prosthetic suturing device shown from a distal perspective.
Figure 6:
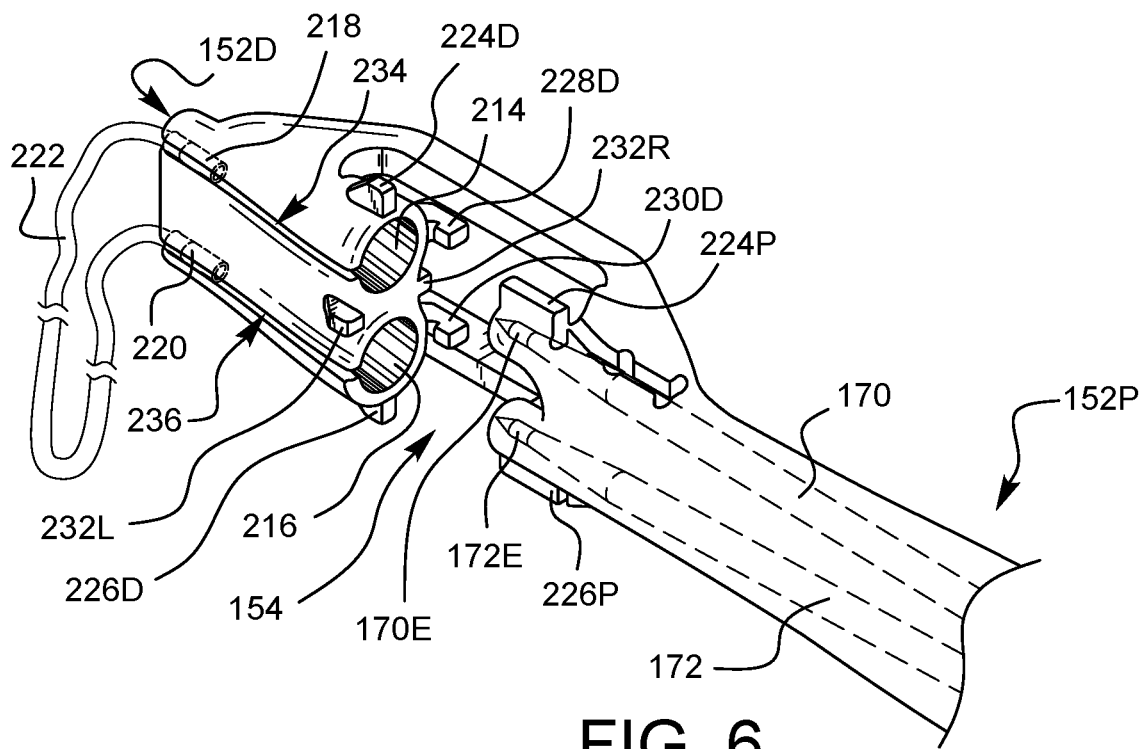
FIG. 6 is an enlarged perspective view of the guide tip from FIG. 5 shown from a proximal perspective.

FIGS. 5 and 6 are enlarged perspective views of one embodiment of a guide tip 152 for a prosthetic suturing device shown from distal and proximal perspectives, respectively. Passages pass within the proximal end 152P of the guide tip 152, guiding the first and second needles 170, 172 towards first and second needle guides 210, 212, respectively. The needle guides 210, 212 help to guide the needles 170, 172 through the cuff receiving area 154 defined by the guide tip 152.

The guide tip 152 also has first and second adapter receiving apertures 214, 216, located in the distal end 152D of the guide tip 152. The adapter receiving apertures 214, 216 are configured to hold first and second suture adapters 218, 220, respectively. The suture adapters 218, 220 may each be coupled to a different end of a suture 222. The suture adapters 218, 220 are designed to be engaged by the ends 170E, 172E of the first and second needles, respectively, such that the needles 170, 172, when contacting the adapters 218, 220 will be able to pull the adapters 218, 220 (and therefore, the ends of the suture 222) back through the cuff receiving area. One non-limiting example of suitable adapters include ferrules into which the needle tips 170E, 172E may be pressed. For convenience, this specification will refer to the adapters 218, 220 as ferrules. Similarly, the specification will also refer to the adapter receiving apertures 214, 216 as ferrule holders, but it should be understood that the broader interpretations apply where the claims are concerned, unless otherwise specified.

The distal end 152D of the guide tip 152 also defines first and second suture removal passages 234, 236 which are in communication with the first and second ferrule holders 214, 216. The removal passages 234, 236 allow the suture 222 which is coupled to the ferrules 218, 220 to be routed out the distal end 152D of the device after the ferrules 218, 220 are placed into the ferrule holders 214, 216.

The ferrule receiving apertures 214, 216 each have flared ends facing the cuff receiving area 154. As will be shown and discussed in more detail later in this specification, a sewing cuff of a replacement heart valve will be placed into the cuff receiving area 154, and then the needles 170, 172 will be advanced, piercing the sewing cuff and continuing on to couple with the ferrules 218, 220 before being withdrawn to pull the suture ends back through the sewing cuff. The sewing cuff material will tend to be pushed into the ferrule receiving apertures 214, 216, so the flared ends are helpful in preventing the sewing cuff material from becoming jammed between the needles 170, 172 and their respective ferrule receiving apertures 214, 216.

This embodiment of a guide tip 152 also has many different alignment guides for helping a user to visualize where the needles (which are mainly hidden from the user) will contact the sewing cuff. For example, the guide tip 152 has a first proximal horizontal needle alignment guide 224P adjacent the first needle guide 210. Similarly, the guide tip 152 has a second proximal horizontal needle alignment guide 226P adjacent the second needle guide 212. The guide tip 152 also has a first distal horizontal needle alignment guide 224D and a second distal horizontal needle alignment guide 226D adjacent the first and second ferrule receiving apertures 214, 216, respectively. As a sewing cuff is moved horizontally in relation to these horizontal needle alignment guides 224P, 224D, 226P, 226D, the intended horizontal penetration location of the needle relative the cuff can be judged from the alignment guides.

The guide tip 152 also has a first proximal vertical needle alignment guide 228P adjacent the first needle guide 210. Similarly, the guide tip 152 has a second proximal vertical needle alignment guide 230P adjacent the second needle guide 212. The guide tip 152 also has a first distal vertical needle alignment guide 228D and a second distal vertical needle alignment guide 230D adjacent the first and second ferrule receiving apertures 214, 216, respectively. As a sewing cuff is moved vertically in relation to these vertical needle alignment guides 228P, 228D, 230P, 230D, the intended vertical penetration location of the needle relative the cuff can be judged from the alignment guides.

The guide tip 152 also has a left central alignment guide 232L and a right central alignment guide 232R which are located on a plane substantially central to the first and second ferrule holders 214, 216 for further needle visualization.

FIG. 7B is a partially cross-sectioned side view of the prosthetic suturing device 150 of FIG. 2B with the needles 170, 172 in a retracted position. FIG. 7A is a top view of the device 150 from FIG. 6B, hiding the handle, housing, spring, and hard stop in order to more clearly show the proximal needle orientation. In this embodiment, on the proximal end, the needles 170, 172 are oriented in a horizontal row, but they are spiraled inside the device to be aligned to pass vertically into the cuff receiving area 154. In the retracted position of FIG. 7B, the ends of the needles 170, 172 are located just inside the guide tip 152 on the proximal side of the cuff receiving area 154.

FIG. 8B is a partially cross-sectioned side view of the prosthetic suturing device 150 of FIG. 2B, with the ends of the needles 170E, 172E in a partially engaged position as they pass through the cuff-receiving area 154. FIG. 8A is a top view of the device from FIG. 8B, hiding the handle, housing, spring, and hard stop in order to more clearly shown the proximal needle orientation. The handle 160 has been moved 174 toward the housing grip 175, causing the needles 170, 172 to be moved in a distal direction 238.

FIG. 9B is a partially cross-sectioned side view of the prosthetic suturing device 150 of FIG. 2B, with the ends of the needles 170E, 172E in a fully engaged position and coupled to the suture ferrules 218, 220 held in the distal end of the guide tip 152. FIG. 9A is a top view of the device from FIG. 9B, hiding the handle, housing, spring, and hard stop in order to more clearly show the proximal needle orientation. The handle 160 has contacted the hard stop 167 to prevent the needles 170E, 172E from pressing too hard into the ferrules 218, 220.

FIG. 10B is a partially cross-sectioned side view of the prosthetic suturing device 150 of FIG. 2B, with the needles 170, 172 partially retracted and pulling the suture ferrules 218, 220 and suture 222 back through the cuff receiving area 154. FIG. 10A is a top view of the device from FIG. 10B, hiding the handle, housing, spring, and hard stop in order to more clearly show the proximal needle orientation. The handle 160 has been partially released, and the spring 164 has caused the handle to move 242 away from the housing grip 175, thereby causing the needles 170, 172 to move in a proximal direction 240.

Figure 11C:
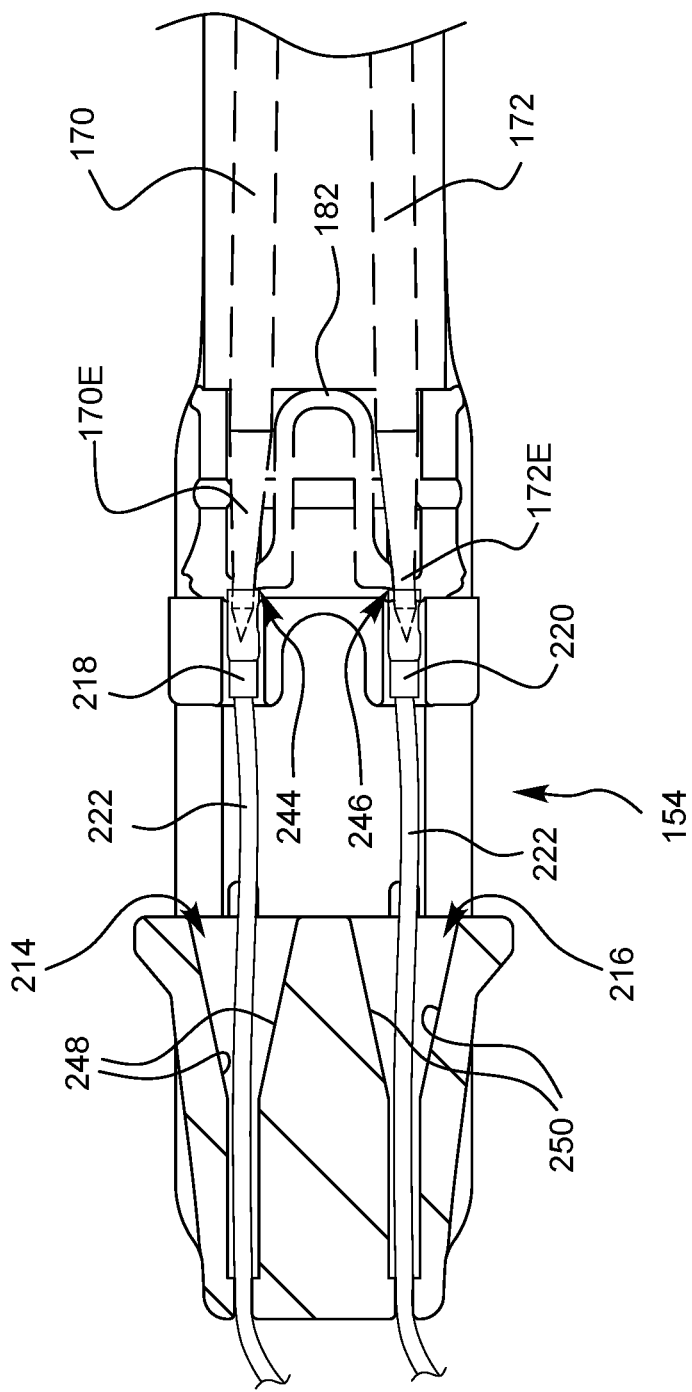
FIG. 11C is an enlarged partial cross-sectional view of the guide tip from FIG. 11B, showing the ferrules coupled to the needles being held distally to the ferrule removal spring.

FIG. 11B is a partially cross-sectioned side view of the prosthetic suturing device 150 of FIG. 2B, with the needles 170, 172 fully retracted. FIG. 11A is a top view of the device from FIG. 11B, hiding the handle, housing, spring, and hard stop in order to more clearly show the proximal needle orientation. The position of the needles 170, 172 in FIG. 11B is the position the needles 170, 172 take when the user is not applying force to the handle 160. FIG. 11C is an enlarged partial cross-sectional view of the guide tip 152 from FIG. 11B, showing the ferrules 218, 220 coupled to the ends of the needles 170E, 172E being held distally to the ferrule removal spring 182. The ferrule removal spring 182 has a first edge 244 which rides on the first needle 170 and which is positioned to push the ferrule 218 off of the first needle 170 if the needle 170 is moved more in a proximal direction. The ferrule removal spring 182 also has a second edge 246 which rides the second needle 172 and which is positioned to push the ferrule 220 off of the second needle 172 if the needle 172 is moved more in a proximal direction. As it stands in the view of FIG. 11C, however, the ferrules 218, 220 are still coupled to their respective needle ends 170E, 172E. The suture 222 has been pulled through the cuff receiving area 154 on a path where the needles 170, 172 had been pulled back. As will be shown and described in later figures, if there had been a sewing cuff located in the cuff receiving area, the suture 222 would have been pulled back through the sewing cuff in two locations (where the first and second needles 170, 172 had passed).

The view of FIG. 11C also offers a cross-sectional look at the first and second ferrule receiving apertures 214, 216. The flared end 248 of the first ferrule receiving aperture 214 and the flared end 250 of the second ferrule receiving aperture 216 can be seen more clearly in this view.

Figure 12C:
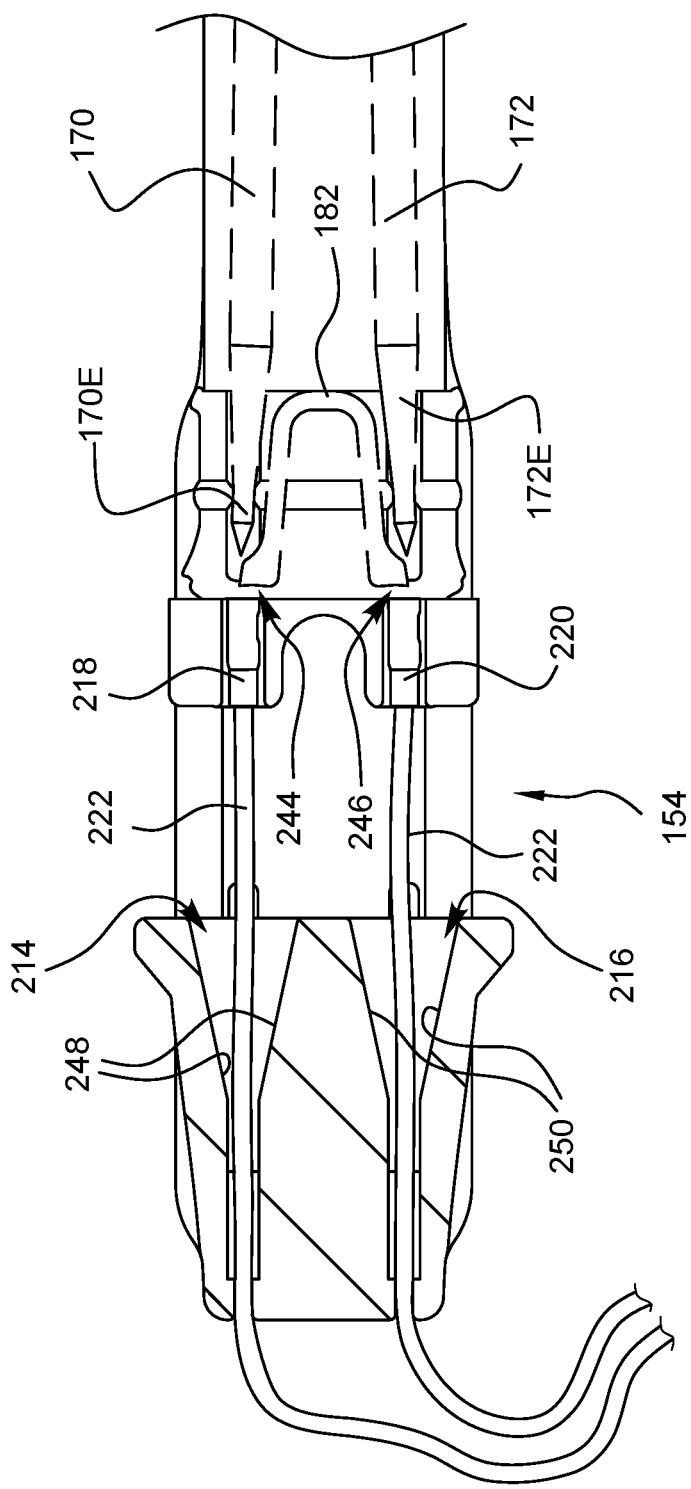
FIG. 12C is an enlarged partial cross-sectional view of the guide tip from FIG. 12B, showing the ferrules decoupled from the needles after having been removed from the needles by the ferrule removal spring.

FIG. 12B is a partially cross-sectioned side view of the prosthetic suturing device 150 of FIG. 2B, with the needles 170, 172 hyper-retracted. FIG. 12A is a top view of the device from FIG. 12B, hiding the handle, housing, spring, and hard stop in order to more clearly show the proximal needle orientation. In FIG. 12B, the user has applied a force to the handle 160 in a direction away 242 from the grip 175. The handle 160 may contact the handle stop 166 which can be designed to flex or give in order to allow the handle to move in this direction 242. This causes the needles 170, 172 to retract more than the normal resting state of FIG. 11B in a proximal direction 240. FIG. 12C is an enlarged partial cross-sectional view of the guide tip 152 from FIG. 12B, showing what happens when the needles 170, 172 are hyper-retracted in this fashion. The ferrules 218, 220 are decoupled from the ends of the needles 170E, 172E after having been pushed off of the needles 170E, 172E by the ferrule removal spring 182. This allows the suture to be removed from the device 150, and a new set of ferrules may be loaded into the device. This can be helpful in a cardiac surgery where there are often many pairs of suture ends which have been sewn into tissue and which then have to be sewn into corresponding positions in a sewing cuff of a replacement anatomical structure.

Figure 13:
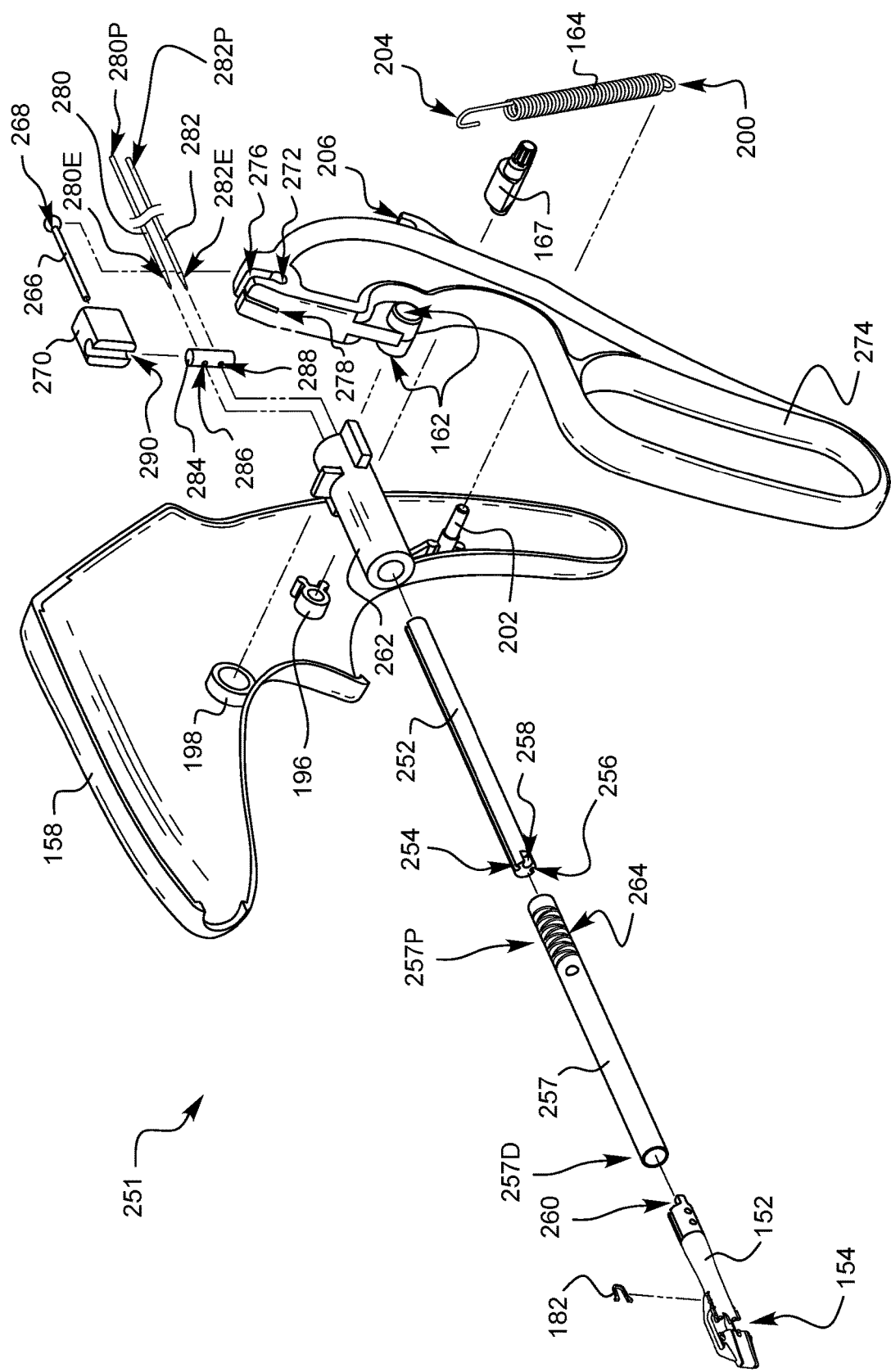
FIG. 13 is an exploded perspective view of another embodiment of a prosthetic suturing device.

FIG. 13 is an exploded perspective view of another embodiment of a prosthetic suturing device 251. The main difference between this embodiment and the previous embodiments is that the needles retain a vertical alignment throughout, rather than starting in a horizontal alignment and then being twisted into a vertical alignment. A needle guide tube 252, this one having a first straight track 254 and a second straight track 256, is placed into a proximal end 257P of shaft 257. A guide tip 152 is placed into a distal end 257D of the shaft 257, and a notch 258 of the needle guide tube 252 is aligned with a key 260 of the guide tip 152 inside of the shaft 257. A shaft holder 262 is coupled to grooves 264 of the shaft 257.

A drive rod 266 has a ball end 268 on a proximal end of the drive rod 266. The distal end of the drive rod 266 is coupled to a drive block 270. The ball end 268 of the drive rod 266 is placed into a side opening 272 in the handle 274, while the drive rod is pulled across a top slot 276 and down a forward slot 278 in the handle. A first needle 280 has an end 280E configured to engage a suture adapter, such as a ferrule. The first needle 280 also has a proximal needle end 280P. A second needle 282 has an end 282E configured to engage a suture adapter such as a ferrule. The second needle 282 also has a proximal needle end 282P. The second needle 282 is placed into the second straight track 256 of the needle guide tube 252, end 282E first. The ferrule release spring 182 may be placed into a slot in the top of the guide tip 152 and rested on the second needle 282. The first needle 280 may then be placed into the first straight track 254 of the needle guide tube 252, end 280E first, so that the spring 182 is compressed between the two needles 280, 282 as in previous embodiments.

A needle connector 284 has first and second connector holes 286, 288 into which the proximal ends of the first and second needles 280P, 282P are placed, such that the proximal ends 280P, 282P are coupled to their respective connector holes 286, 288. The needle connector 284 is coupled to a connector receptacle 290 in the drive block 270, completing the link between the needles 280, 282 and the handle 274.

The pivot point 162 of the handle 274 may be aligned in a pivot boss 198 formed in the housing 158. The shaft holder 262 may be held and supported by a variety of features on the inside of the housing 158. Such features are not illustrated for simplicity, but are well known to those skilled in the art. Although only one half of the housing 158 is shown in this exploded view, it should be understood that a complementary half of the housing is also present (though not shown) and would have similar boss features to allow pivoting of the handle 274 and bracing of the shaft holder 262.

The hard stop 167 may be mounted in a hard stop boss 196 to limit travel of the handle 274, while a lower end 200 of spring 164 may be coupled to a fixed spring attachment point 202 on the housing. An upper end 204 of the spring 164 may be hooked onto a handle spring attachment point 206.

Figure 14:
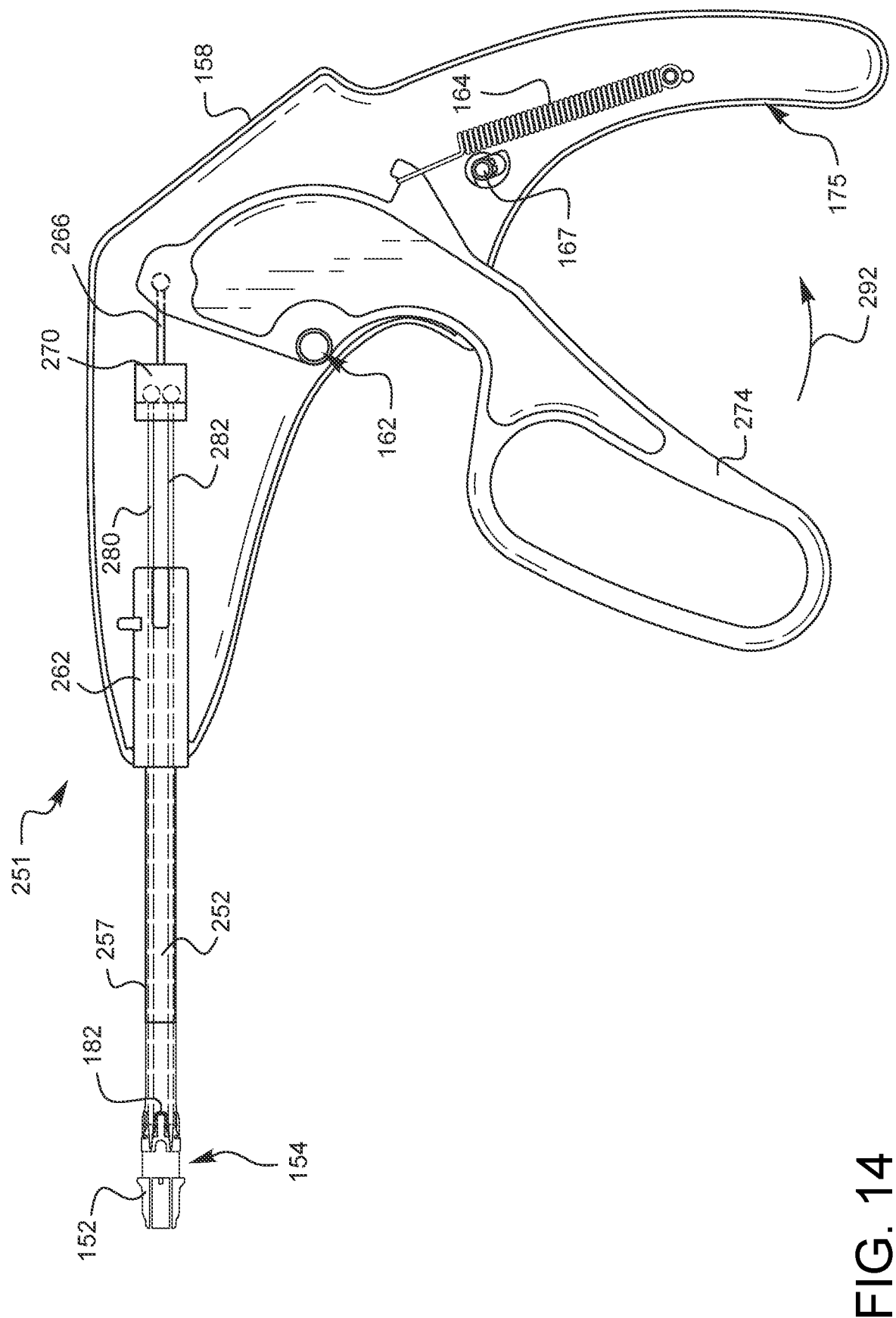
FIG. 14 is a partially exposed side view of the prosthetic suturing device of FIG. 13.

FIG. 14 is a partially exposed side view of the prosthetic suturing device 251 of FIG. 13. When the handle 274 is squeezed 292 towards the grip 175, the first and second needles 280, 282 are moved distally through the cuff receiving area 154 in a manner as shown in the previous embodiments.

Figure 15:
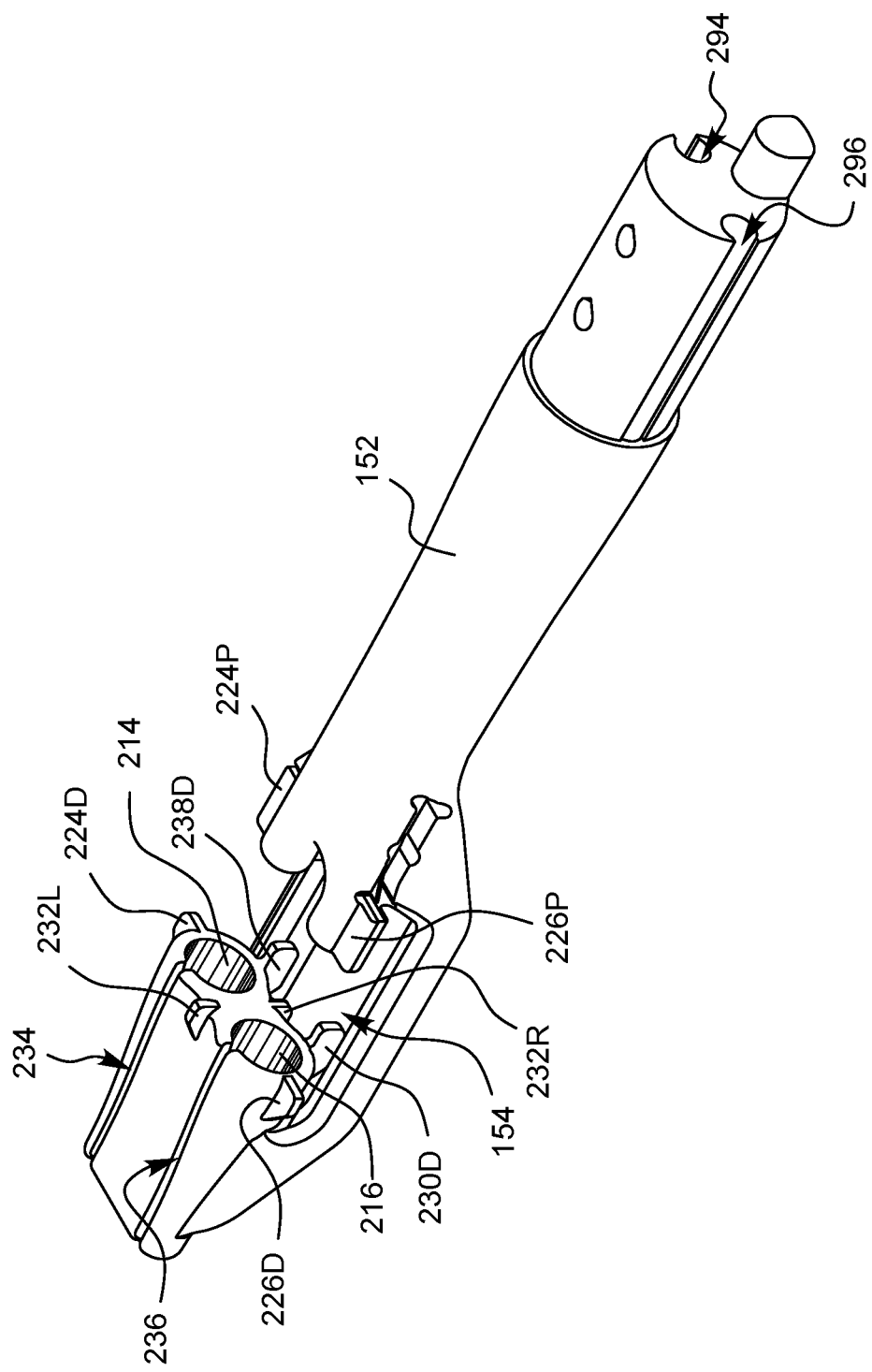
FIG. 15 is a perspective view of one embodiment of a guide tip for a prosthetic suturing device.

FIG. 15 is a perspective view of one embodiment of a guide tip 152 for a prosthetic suturing device. Most features of this embodiment of a guide tip 152 have been discussed above, however, this embodiment can also be seen to have first and second proximal needle guides 294, 296. These guides 294, 296 work with the needle guides 210, 212 (not visible in this view, but discussed previously) in order to help guide the needles 280, 282 through the cuff receiving area while maintaining an expected vertical alignment and spacing between the needles 280, 282.

Figure 16:
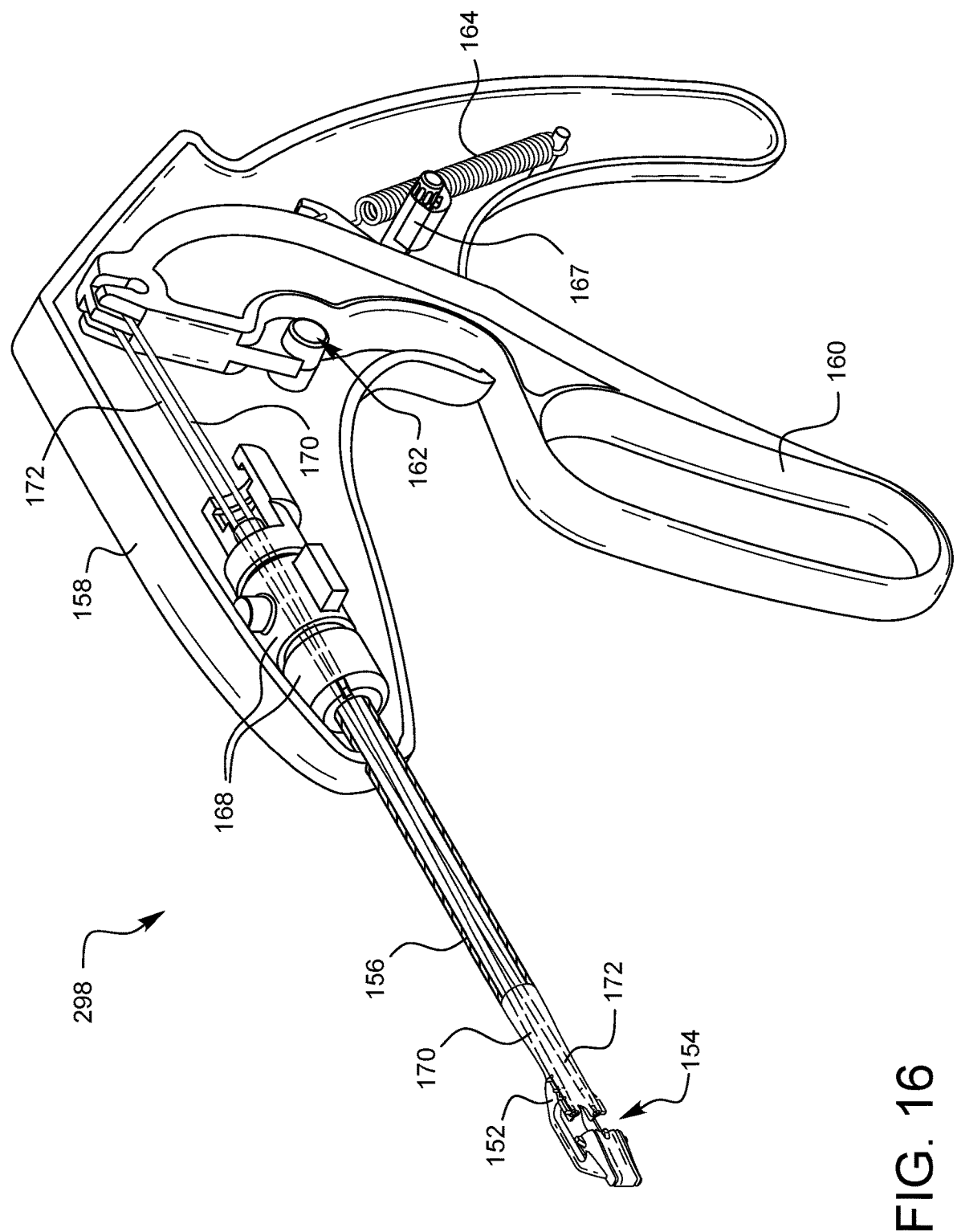
FIG. 16 is a partially exposed partial cross-sectional perspective view of another embodiment of a prosthetic suturing device, utilizing the guide tip of FIG. 15 without a needle guide tube.

Depending on the embodiment, the needle guides 294, 296 in the guide tip 152 may be used to force needles which start horizontally into a vertical alignment without the need for a needle guide tube. FIG. 16 illustrates just such an embodiment, and is a partially exposed partial cross-sectional perspective view of another embodiment of a prosthetic suturing device 298, utilizing the guide tip of FIG. 15 without a needle guide tube. The features of this embodiment are just like those of the embodiment of FIG. 2B, however, this device 298 does not use the a needle guide tube. Instead, the needles 170, 172 start horizontally as held by the handle 160, but are then twisted into vertical orientation by the guide tip 152. In order to prevent the needles from buckling, it may be necessary to go with a heavier gauge needle when a suture guide tube is not used.

Figure 17:
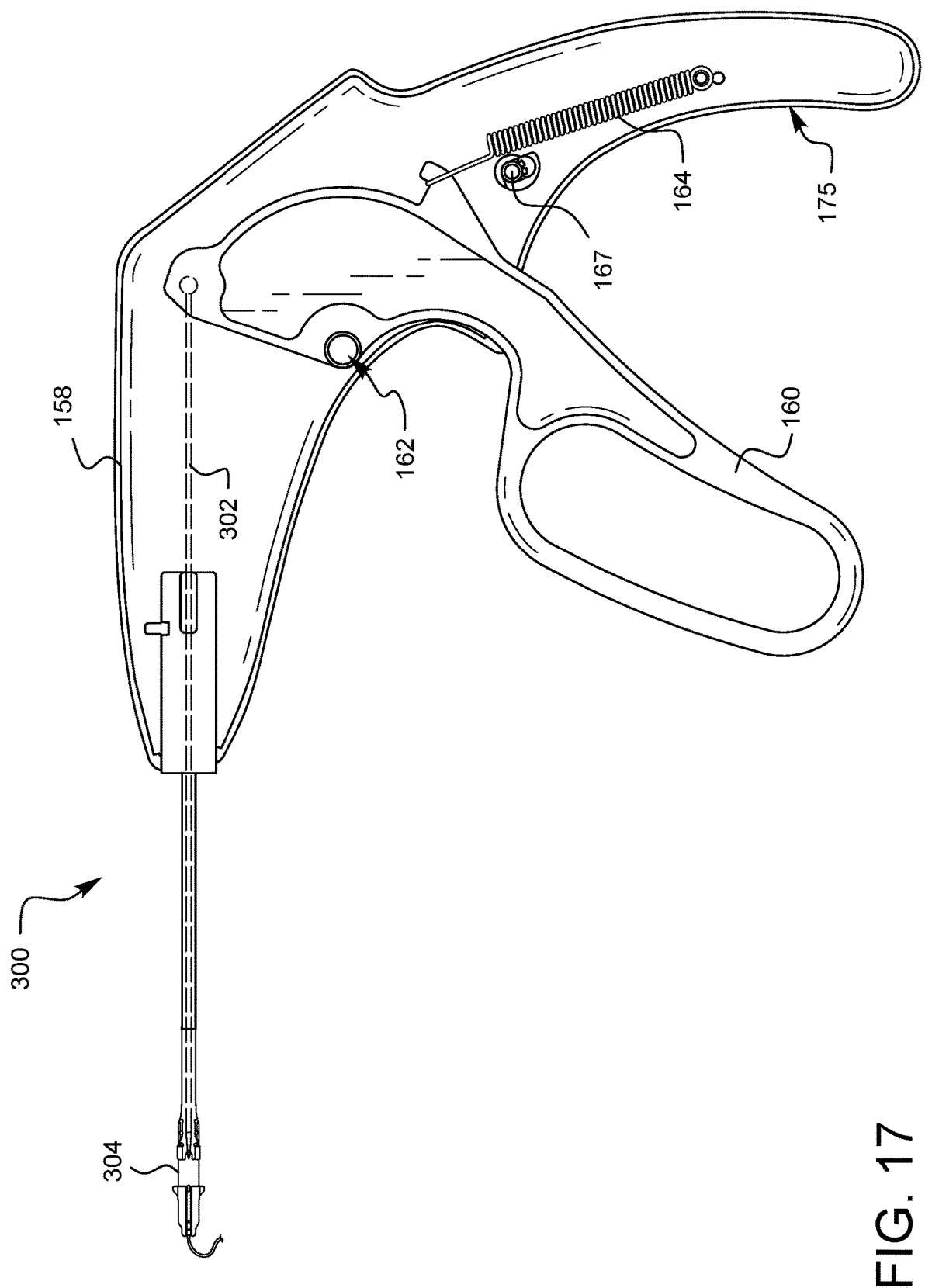
FIG. 17 is a partially exposed side view of a further embodiment of a prosthetic suturing device.

FIG. 17 is a partially exposed side view of a further embodiment of a prosthetic suturing device 300. This embodiment only has a single needle 302 and a place for a corresponding ferrule holder in the guide tip 304, but the cuff receiving area is still facing left while the handle 160 and grip 175 substantially point down (as in previous embodiments).

Figure 18:
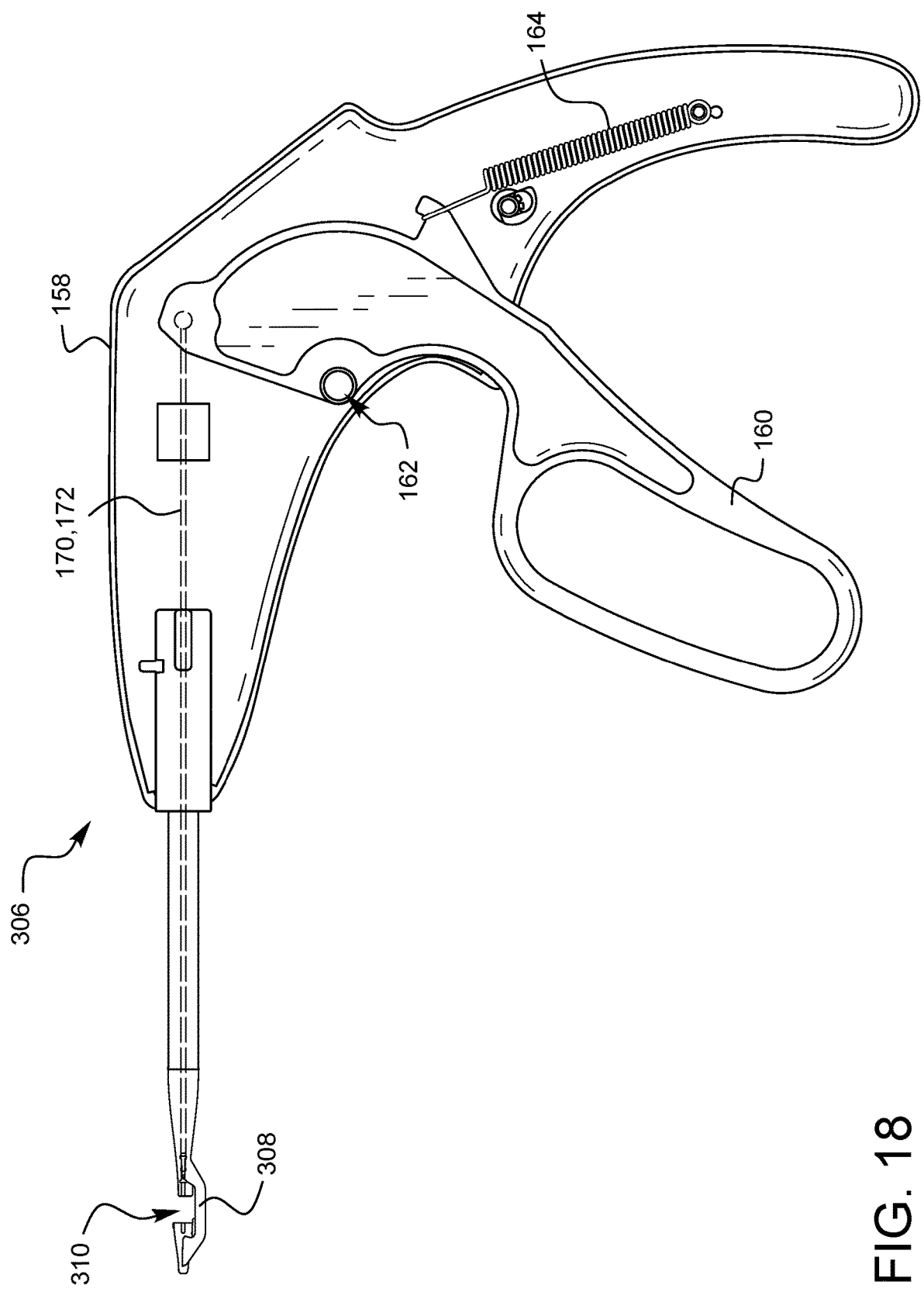
FIG. 18 is a partially exposed side view of another embodiment of a prosthetic suturing device.

FIG. 18 is a partially exposed side view of another embodiment of a prosthetic suturing device 306. In this embodiment, the guide tip 308 has a vertical opening (rather than a horizontal opening like previous embodiments) which defines a cuff receiving area. The needles 170, 172 in this embodiment are aligned horizontally, and otherwise, this device operates like the previous embodiments.

Figure 19B:
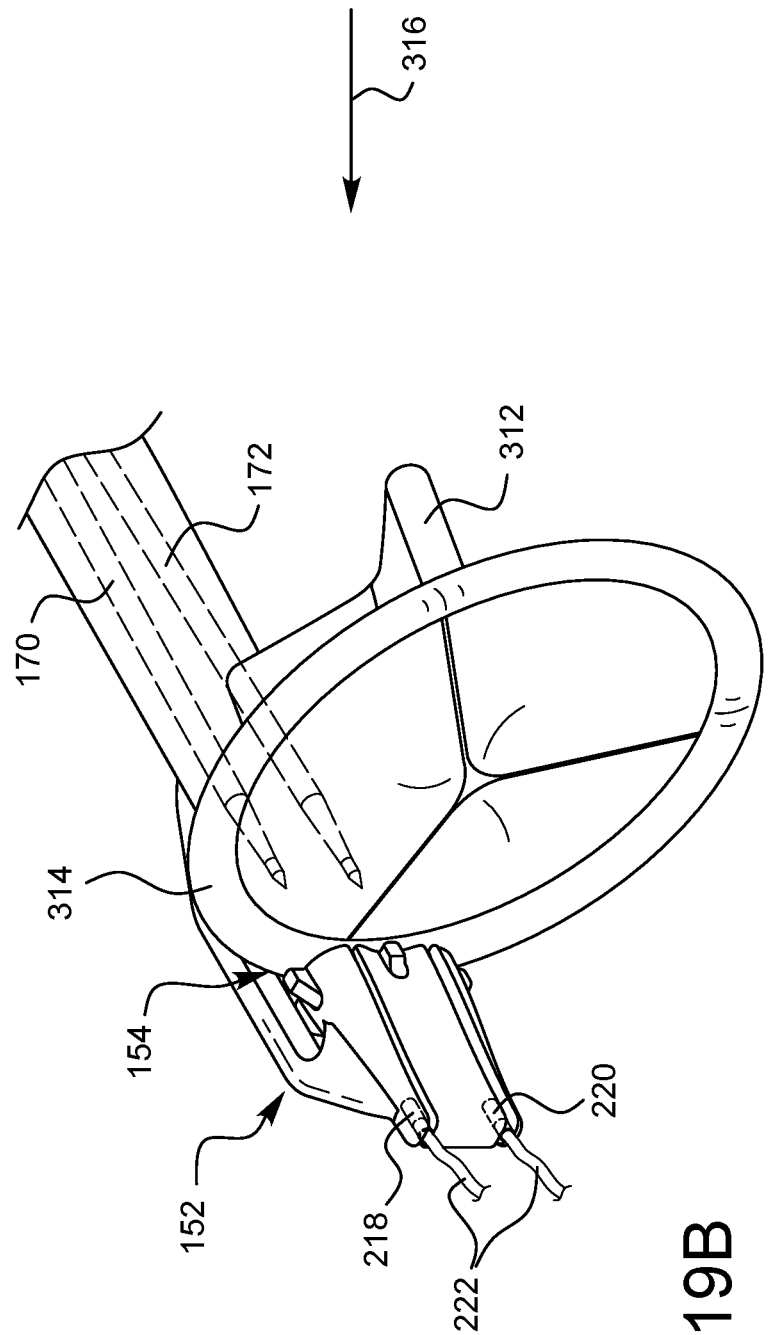
Figure 19D:
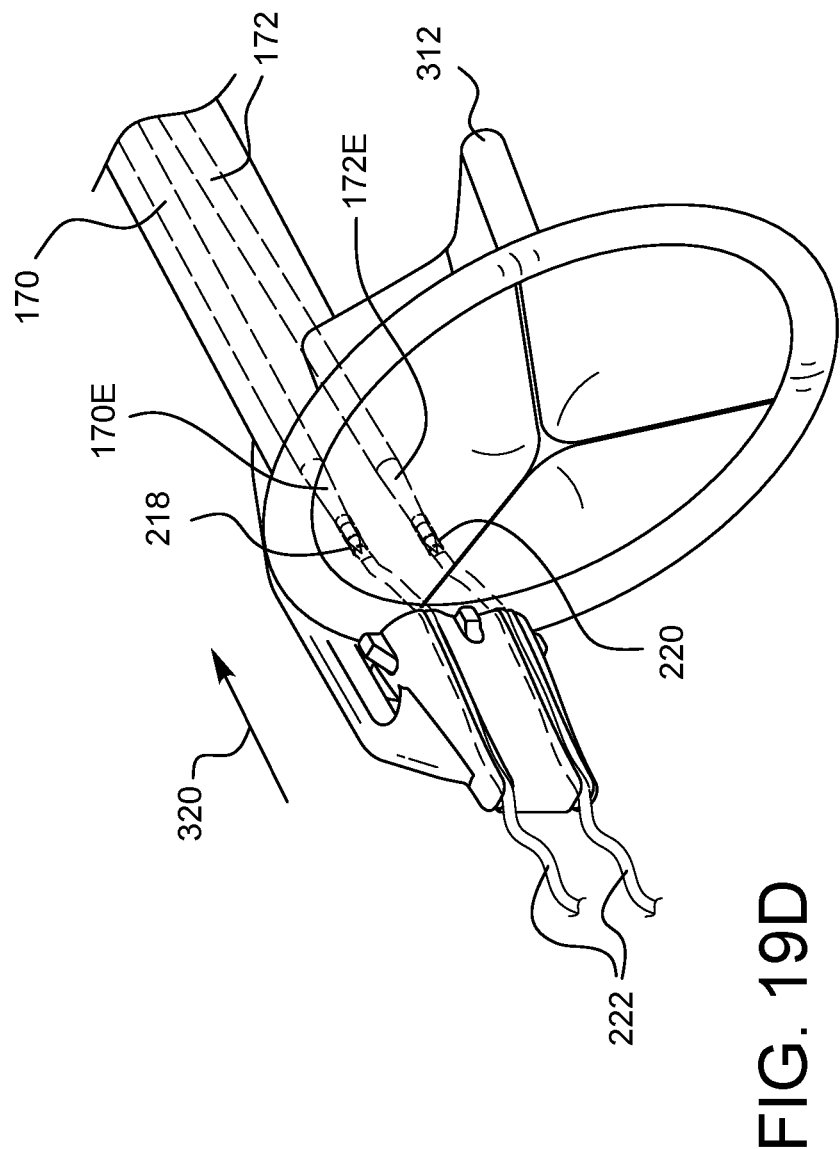

FIGS. 19A-19F illustrate one example of a surgical usage of an embodiment of a prosthetic suturing device. For convenience, only the guide tip 152 of the device is shown in FIGS. 19A-19F. The guide tip 152 is like that of FIGS. 5 and 6, and as noted in the examples above, there are many actuator examples which would result in the vertically aligned needles 170, 172 illustrated here. The surgical situation of this example is as follows, and as illustrated in FIG. 19A: In preparation for installation of a replacement anatomical structure 312 (here, illustrated as a replacement heart valve), a suture 222 has been sewn through a tissue 315 inside of a patient. This could have been done by hand, but preferably with a minimally invasive suturing device which is compatible with ferrules (or some other type of suture adapter). The ferrules 218, 220 were removed from the minimally invasive suturing device and then loaded into the ferrule holders in the distal end of the guide tip 152 outside of the patient. The replacement anatomical structure 312, having a sewing cuff 314, is standing by.

Figure 19E:
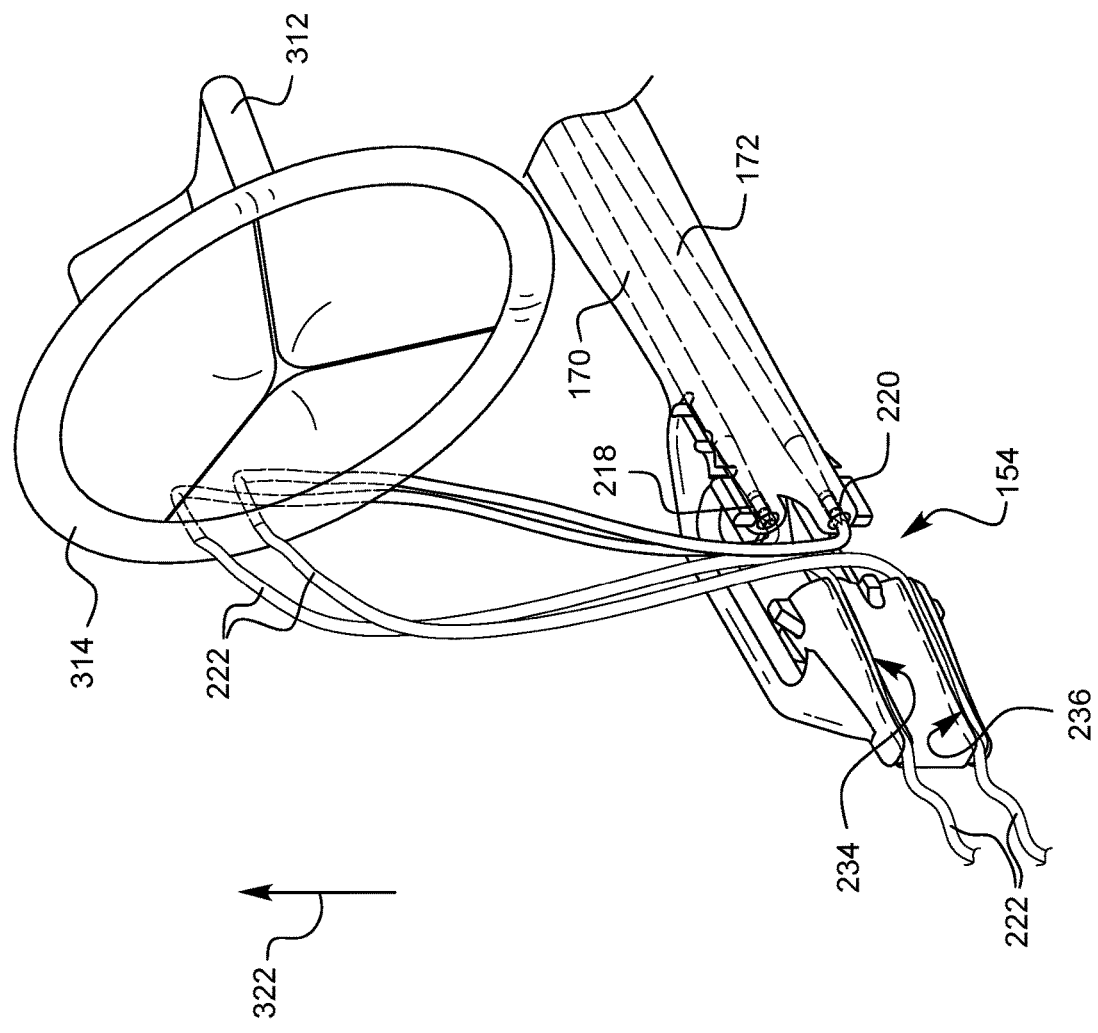
Figure 19F:
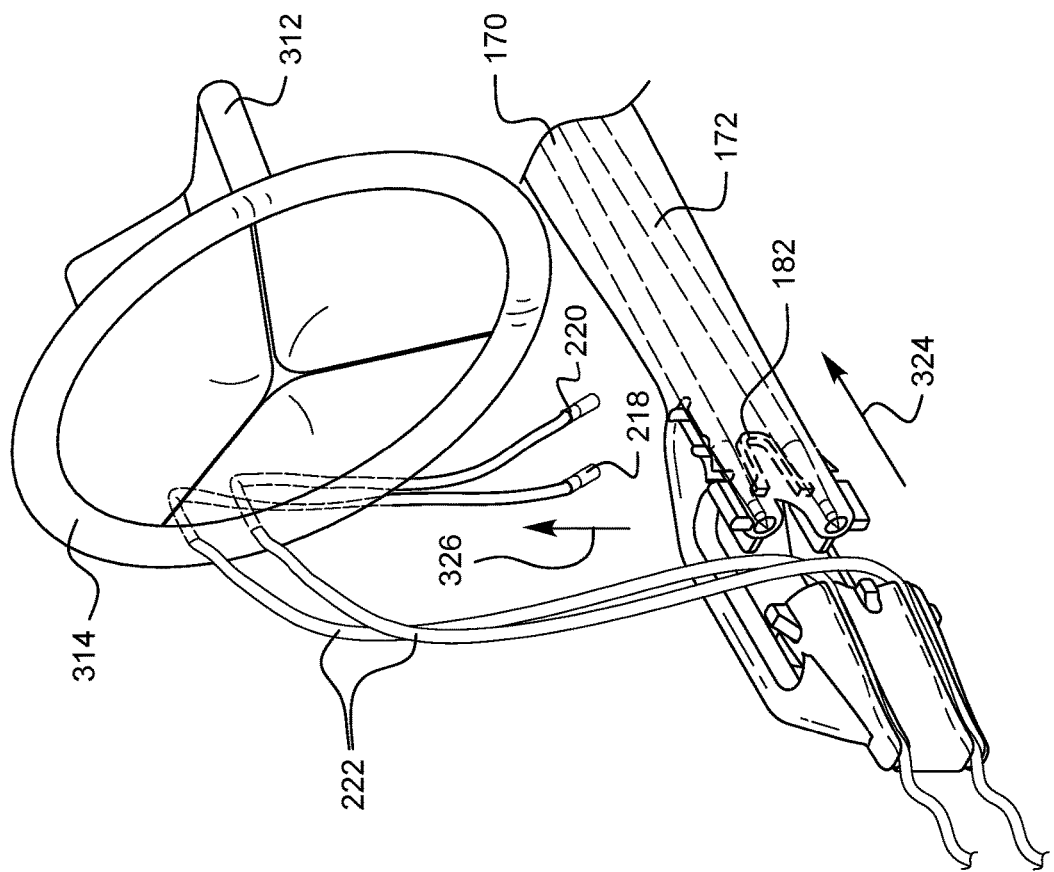

As shown in FIG. 19B, the sewing cuff 314 of the replacement valve 312 is placed 316 into the cuff receiving area 154 of the guide tip 152. As described previously, the needle alignment guides can be used to help position the sewing cuff as desired. Since the cuff receiving area faces to the side, while the handle and grip face substantially downward, it is easier for a surgeon to hold the suturing device with one hand while positioning the valve 312 with the other hand. As shown in FIG. 19C, the device handle (not shown) is squeezed to cause the needles 170, 172 to move distally 318, pierce the sewing cuff 314, and then engage the ferrules 218, 220 with respective ends 170E, 172E of the needles 170, 172. As shown in 19D, the device handle (not shown) is released to cause the needle ends 170E, 172E to move proximally 320 back through the sewing cuff 314, pulling the ferrules 218, 220 and the suture 222 back through the sewing cuff as well. As shown in FIG. 19E, the replacement anatomical structure 312 can be removed 322 from the from the cuff receiving area 154 while the ferrules 218, 220 remain coupled to the needles 170, 172 in the proximal end of the guide tip 152. Although the suture 222 is still illustrated as passing through the ferrule holders in the distal end of the device, it should be understood that the suture 222 can be removed from the ferrule holders by passing it through the suture removal passages 234, 236. As shown in FIG. 19F, the needles 170, 172 may be further moved in a proximal direction 324 (as discussed above) so that the ferrules 218, 220 are pushed off of the needles 170, 172 by the ferrule removal spring 182, thereby releasing the ferrules 218, 220 to move free 326 of the device. By loading other suture ends into the device, this process can be repeated with other suture pairs around the circumference of the sewing cuff 314. This device and method greatly simplify and speed up the process of placing sutures through a sewing cuff of a replacement anatomical structure. Once the desired number of suture ends have been passed through the sewing cuff, those skilled in the art know how to run the replacement anatomical structure down the sutures and against the tissue where the sutures were first placed. The pairs of suture ends may then be tied off with hand-tied or mechanical knots as desired.

Figure 20A:
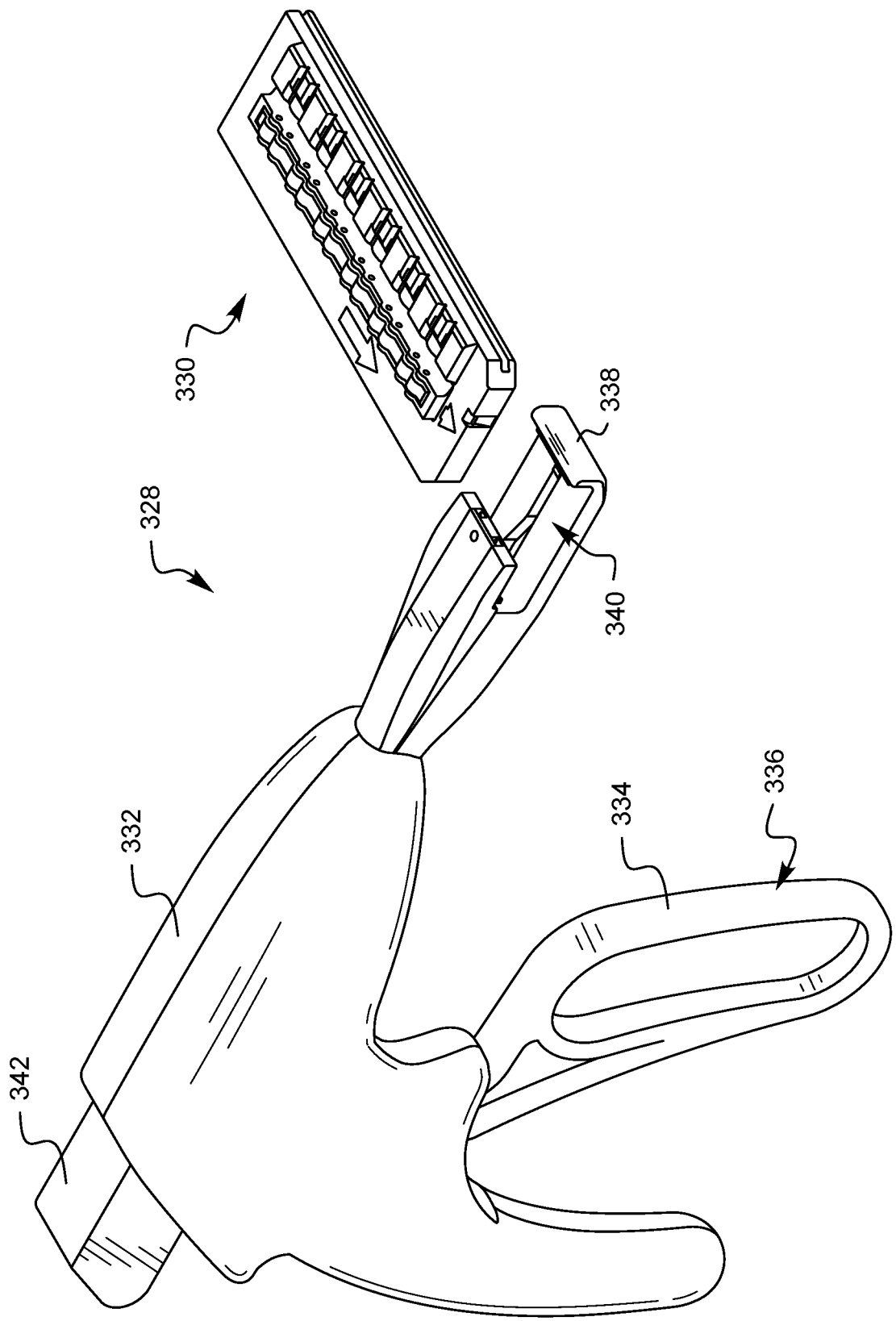
FIG. 20A is a perspective view of one embodiment of a surgical suturing device and one embodiment of a magazine for the surgical suturing device.
Figure 20B:
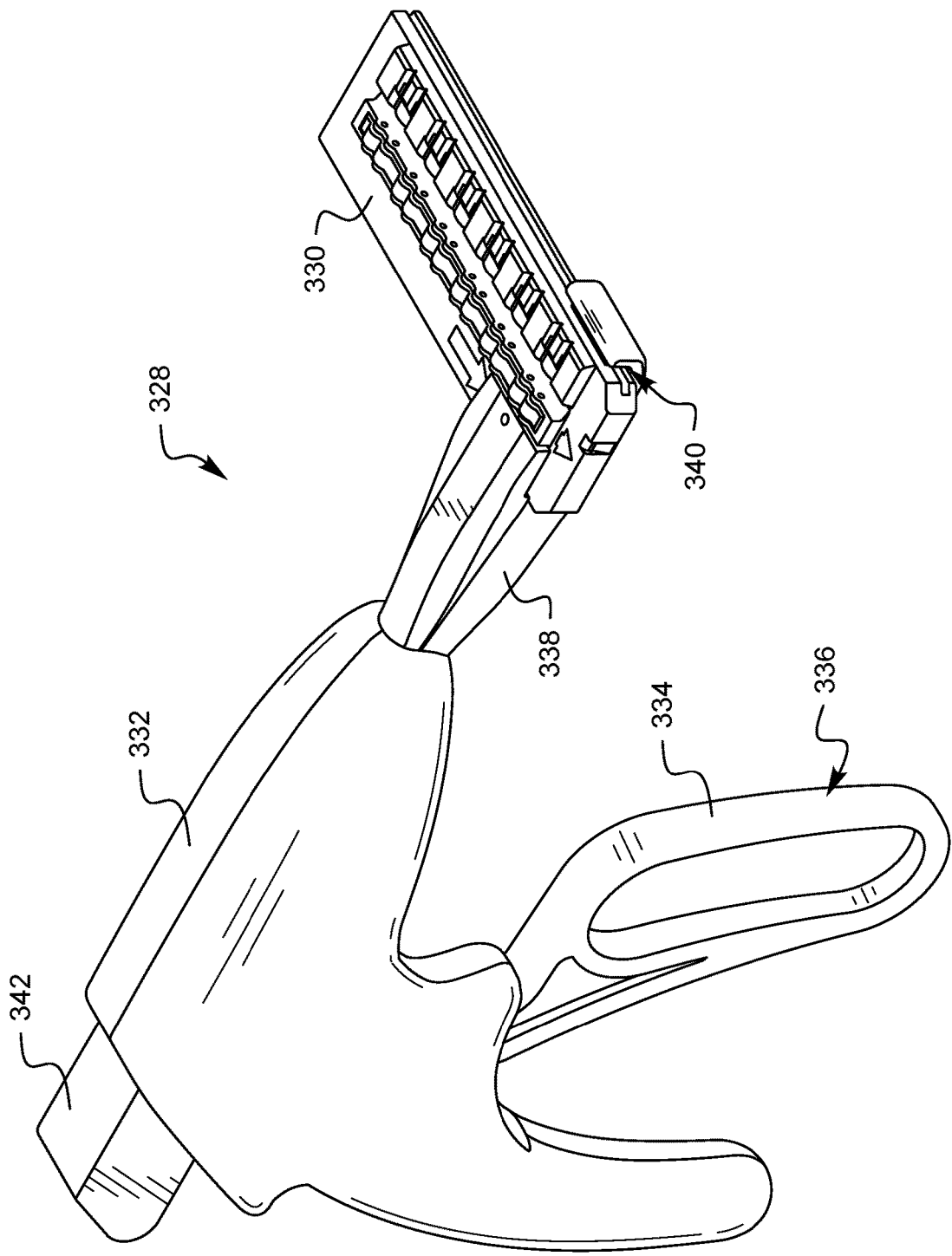
FIG. 20B is a perspective view of the embodiment of the surgical suturing device of FIG. 20A with the magazine installed in a suture magazine receiver of the surgical suturing device.

FIG. 20A is a perspective view of one embodiment of a surgical suturing device 328 and one embodiment of a magazine 330 for the surgical suturing device 328. The surgical suturing device 328 has a housing 332 and an actuator 334 (only the lever handle 336 of which may be seen in this view). The suturing device also has a tip 338 which has a suture magazine receiver 340. The suturing device 328 also has an indexer. Most of the features of the indexer cannot be seen in this view, with the exception of the indexer's push button 342 which can be seen in this view. The indexer is operationally coupled to the suture magazine receiver 340 to be able to move the suture magazine 330 (once installed) from one suturing position to another. This indexing movement will be discussed in more detail in later views. In FIG. 20A, the magazine 330 is shown separated from the surgical suturing device. In FIG. 20B, the magazine 330 is shown installed in the suture magazine receiver 340 of the suturing device. Details of the magazine 330 will be discussed in more detail later in this description.

Figure 21:
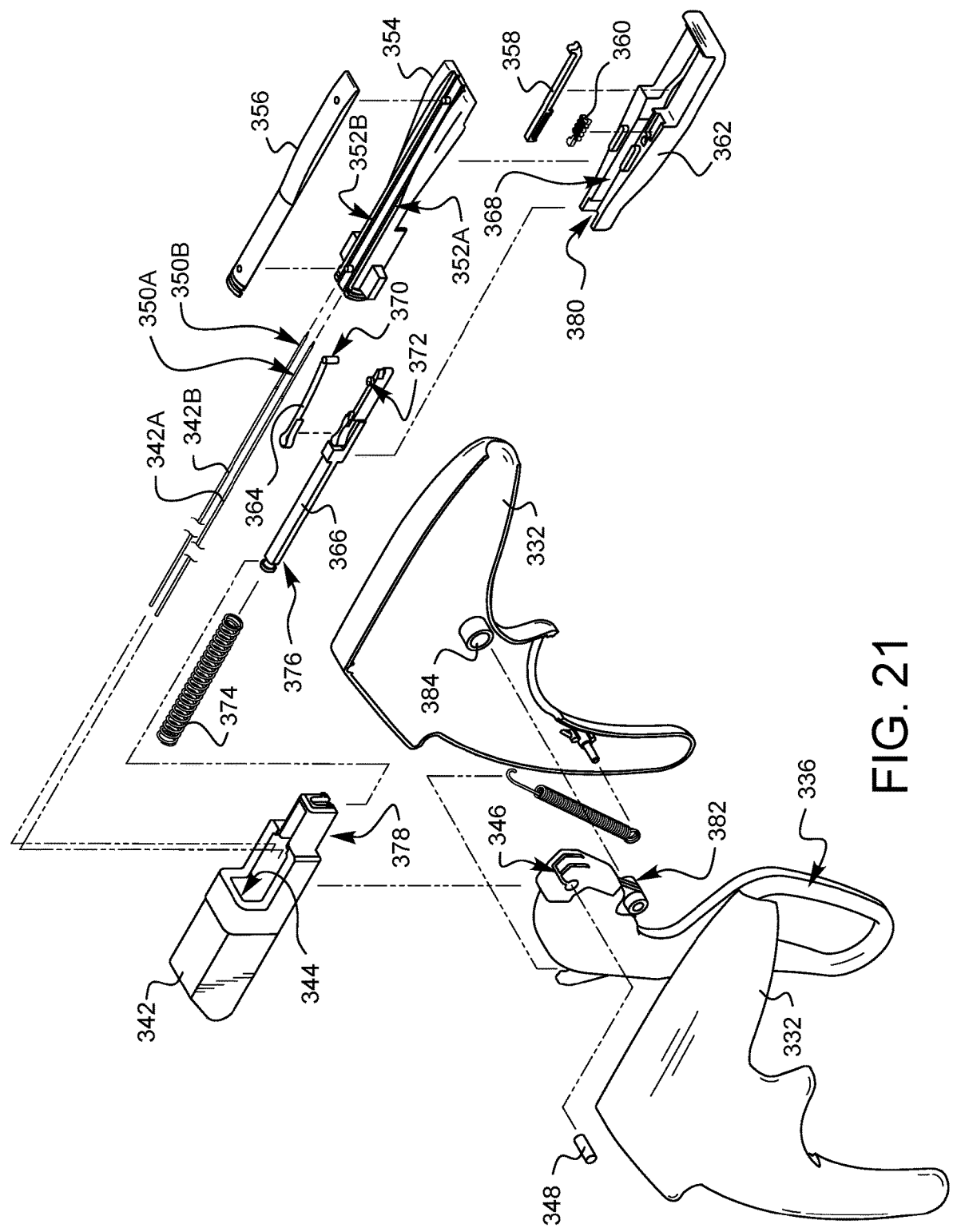
FIG. 21 is an exploded view of the surgical suturing device of FIG. 20A.

FIG. 21 is an exploded view of the surgical suturing device of FIG. 20A. For assembly, a pair of needles 342A, 342B is passed down through an opening 344 in the push button 342 (push control) where they can be inserted into a needle receiver 346 in the actuator handle 336. A needle pin 348 (which may be pre-attached to the two needles) holds the needles pivotably in place in the handle 336. The distal end of the needles 350A, 350B rests in needle guides 352A, 352B formed by middle 354 and top 356 portions of the device tip which are coupled together around the needles 342A, 342B. A forward stop 358 and a stop spring 360 are set into respective grooves of a bottom portion 362 of the device tip. An indexing flexure 364 is coupled to a pusher 366 which is then set into a pushing channel 368 of the tip bottom. For later reference, the indexing flexure 364 has a primary cam 370 and the pusher 366 has a secondary cam 372. A pusher spring element 374 is slid over the proximal end 376 of the pusher 366 and the proximal end 376 of the pusher 366 is coupled to the push button 342. The pusher spring 374 is compressed between the forward end 378 of the push button 342 and a pusher spring receiver 380 of the tip formed when the bottom 362 of the tip is coupled to the middle 354 of the device tip. A pivot point 382 of the handle 336 is aligned with pivot bosses 384 of the housing 332 as the two portions of the housing 332 are brought together. The housing 332 also holds the tip 338 (made of upper, middle, and lower portions 356, 354, and 362) and provides a slideable guide for the push button 342.

Figure 22:
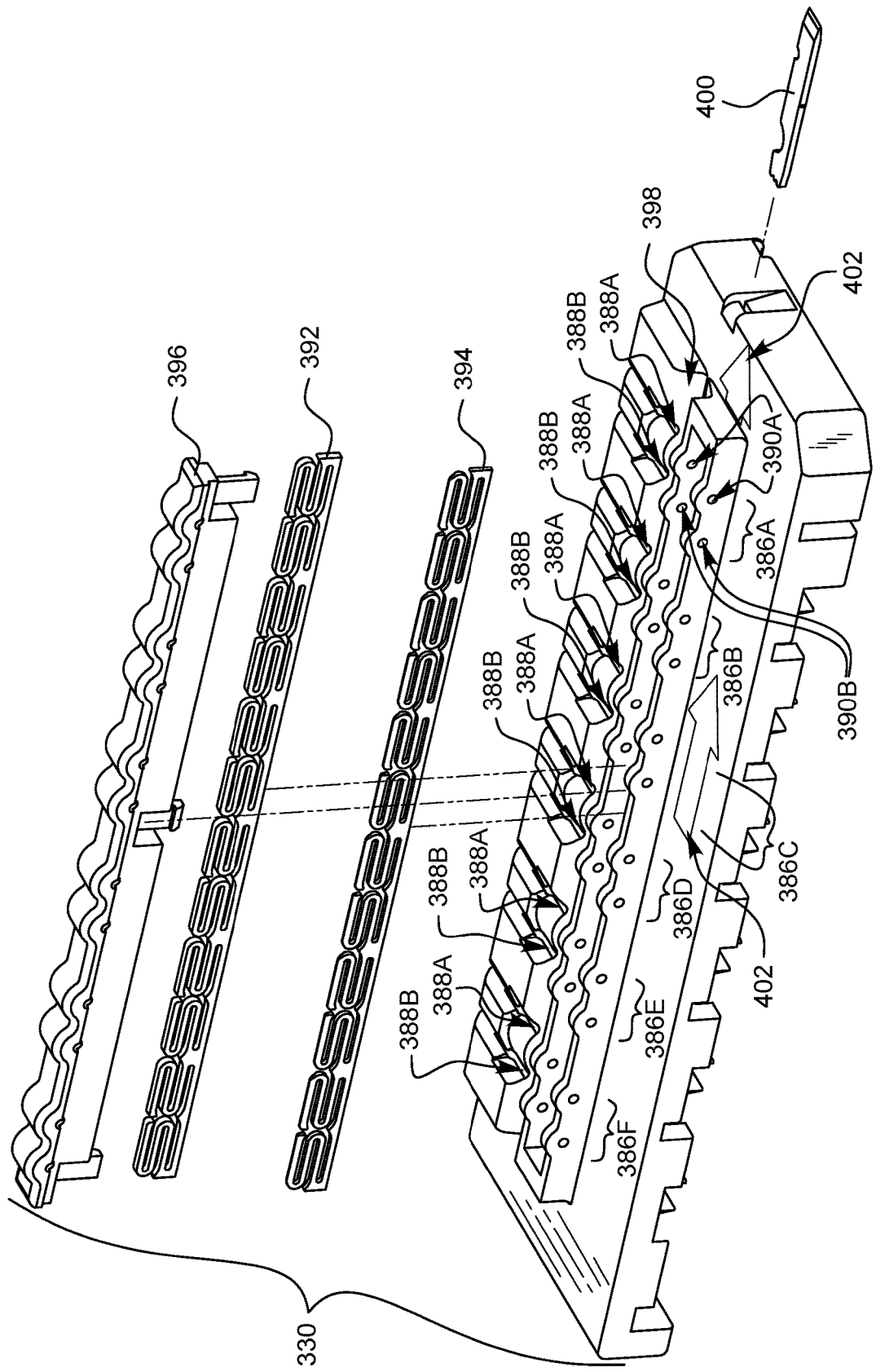
FIG. 22 is an exploded view of the suturing magazine of FIG. 20A.

FIG. 22 is an exploded view of the suturing magazine 330 of FIG. 20A. It has a plurality of suturing positions 386A-386F. In this embodiment, each suturing position 386A-386F has two ferrule holders 388A, 388B to correspond to the two needles 342A, 342B of the suturing device 328. Other embodiments may have more or fewer ferrule holders in each suturing position. A ferrule holder is configured to hold a ferrule which is attached to the end of a suture. A ferrule is an object which can be picked up by a needle which comes into contact with it. Embodiments of ferrules will be discussed further below. In many cardiac surgical procedures, the sutures which have been sewn into the heart tissue where a replacement valve will be anchored will often have ferrules attached to their ends. The suture ferrules can be installed by a surgeon, or someone on his/her staff, into the ferrule holders 388A, 388B of the magazine. In this embodiment, the ferrules on two ends of the same suture may be placed into ferrule holders 388A, 388B of the same suture position in the magazine. The positions 386A-386F in a magazine may be filled in order so that the suture ends are managed, tracked, and kept untangled. Although this embodiment shows a magazine with six suture positions 386A-386F, other embodiments may have fewer or more suture positions.

As will be seen in the discussion below, after the magazine 330 has been inserted into a suturing device 328, the needles 342A, 342B can traverse over the magazine 330 on their way to the ferrules which are held in the ferrule holders 388A, 388B. In order to help keep the needles 342A, 342B aligned with the ferrules as the needles 342A, 342B move, this embodiment of the magazine 330 has two needle alignment guides 390A, 390B in line with each ferrule holder 388A, 388B, respectively. Other embodiments may have fewer or more alignment guides for each needle.

The magazine 330 has a ferrule remover 392 and a ferrule gate 394 which are spaced apart and held in place by a ferrule capture 396. In this embodiment, the ferrule gate 392 is a distal ferrule spring and the ferrule remover 394 is a proximal ferrule spring. The ferrule remover 394 and the ferrule gate 392 may each be a series of separate components or one continuous component. The operation of the ferrule gate 392, the ferrule remover 394, and the ferrule capture 396 will be discussed in more detail below, but it should be noted that the ferrule capture 396 may advantageously be made of a transparent or translucent material in some embodiments to facilitate observation of ferrules which should become captured therein. A sewing cuff receiver 398 is located between the ferrule holders 388A, 388B and the ferrule capture 396.

This embodiment of a magazine also has a cutter 400 which can be held in a portion of the magazine 330 for convenient cutting of sutures when needed. The cutter 400 can be recessed to avoid injury to the people handling the magazine 330 or to the patient. Other embodiments may not have a cutter.

This embodiment of the magazine 330 further has one or more direction indicators 402 to assist the operator in determining the correct direction to insert the magazine 330 into the suturing device.

Embodiments of the magazine will also have an indexable feature configured to enable the magazine to be moved between the plurality of suturing positions. The indexable feature can include, but is not limited to, one or more of the following features: one or more primary cam paths, one or more secondary cam paths, and/or one or more stop receivers, examples of which will be discussed in more detail below. Other embodiments of the indexable feature may include a gear rack.

FIGS. 23A-23F show top, front, left, right, bottom, and rear (upside-down) elevational views, respectively, of the magazine of FIG. 22. In addition to the features already discussed, the primary cam paths 404A-404F, the secondary cam paths 406A-406F, and stop receivers 408A-408F can be seen more clearly. A receiver mating 410 feature is also visible. Some embodiments may not have a receiver mating feature, but a magazine's receiver mating feature is configured to engage a corresponding magazine mating feature in the magazine receiver of the suturing device.

Figure 24:
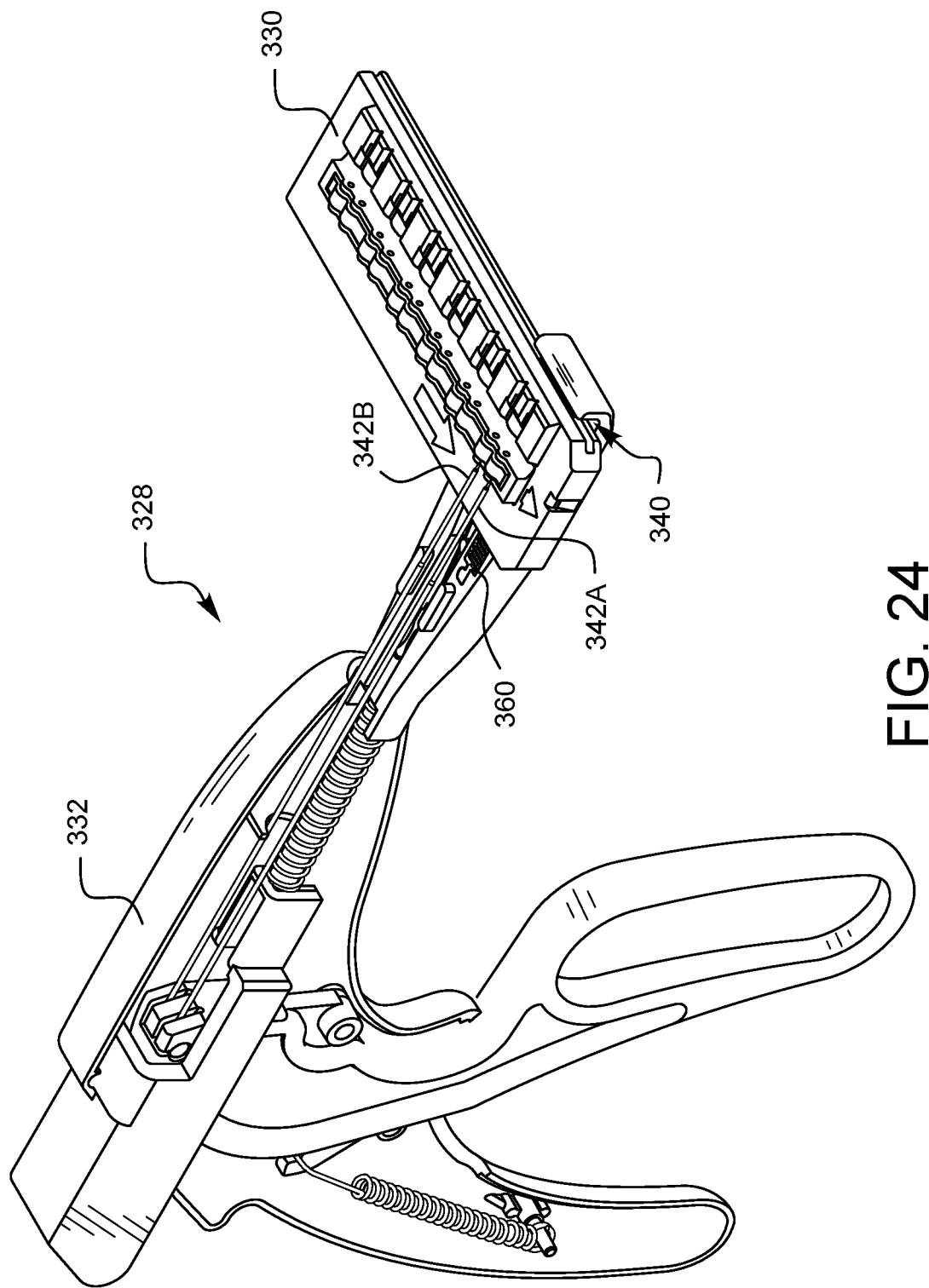
FIG. 24 shows an embodiment of the magazine inserted into the magazine receiver of the suturing device.
Figure 25A:
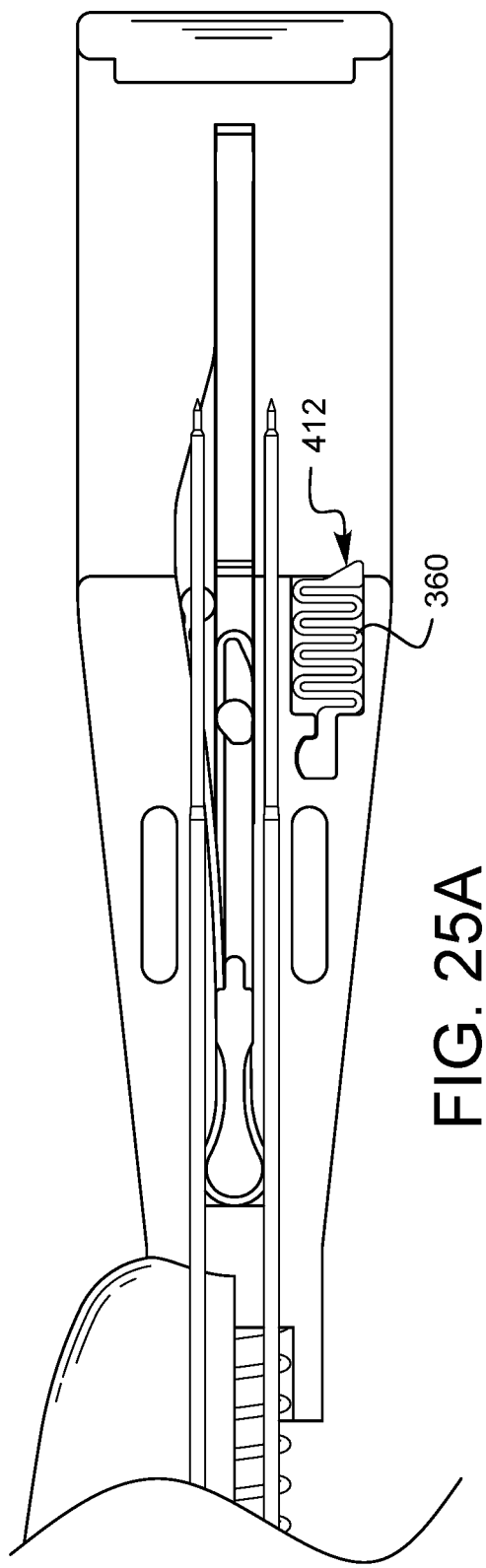
FIGS. 25A and 25B are exposed top and side views, respectively, of the surgical suturing device tip of the device from FIG. 20A.
Figure 25B:
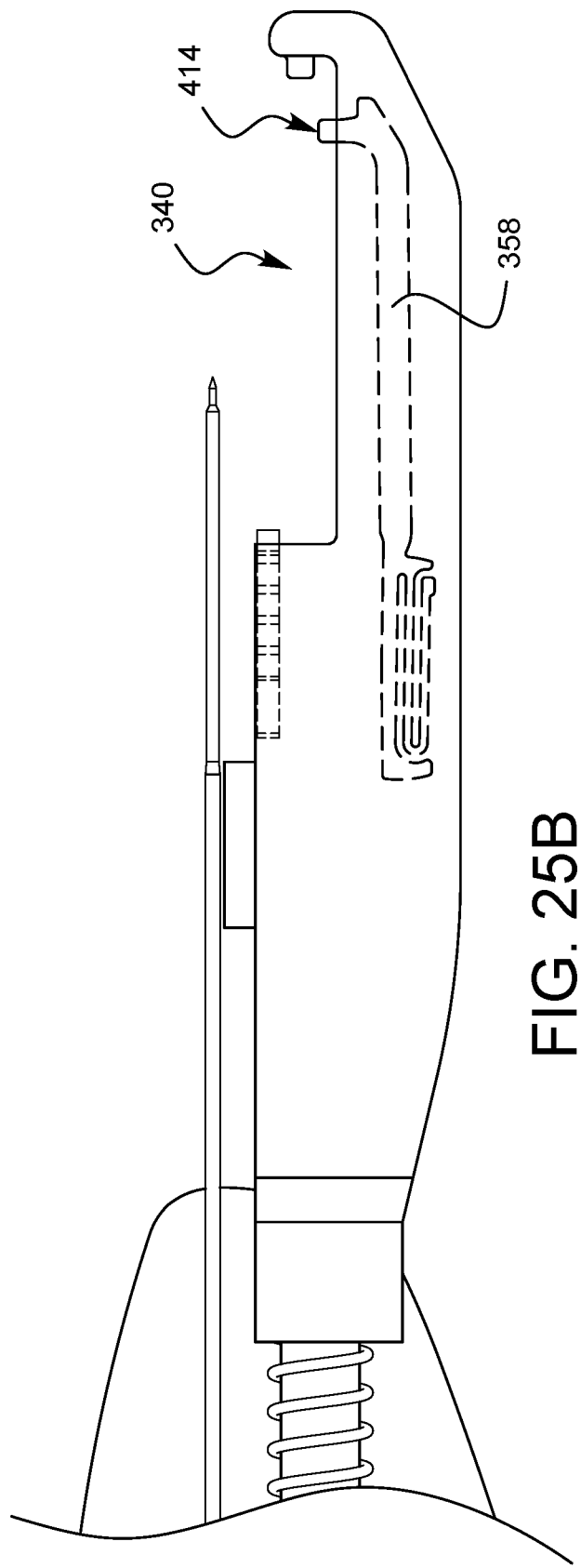

FIG. 24 shows an embodiment of the magazine 330 inserted into the magazine receiver 340 of the suturing device 328. One half of the housing 332 has been removed, along with the middle and top portions of the tip so that some of the hidden elements may more clearly be seen. The tip of the stop spring 360 has engaged the first stop receiver 408A on the magazine, and the first suturing position 386A is in alignment with the two device needles 342A, 342B. The stop spring 360 may be seen more clearly in the exposed top view of FIG. 25A, showing the sewing device from the top. The ramped shape of the tip 412 of the stop spring 360 facilitates movement of the magazine 330 (when installed) in a single direction if an external force is applied. Additionally, the forward stop 358 is normally protruding upward into a stop receiver on the bottom of the magazine. The forward stop 358 may be seen more clearly in the exposed side view of FIG. 25B. The tip 414 of the forward stop 358 rises into the suture magazine receiver 340 to help hold the magazine in a given suturing position, but the forward stop may be disengaged, as will be discussed in more detail below.

Figure 26A:
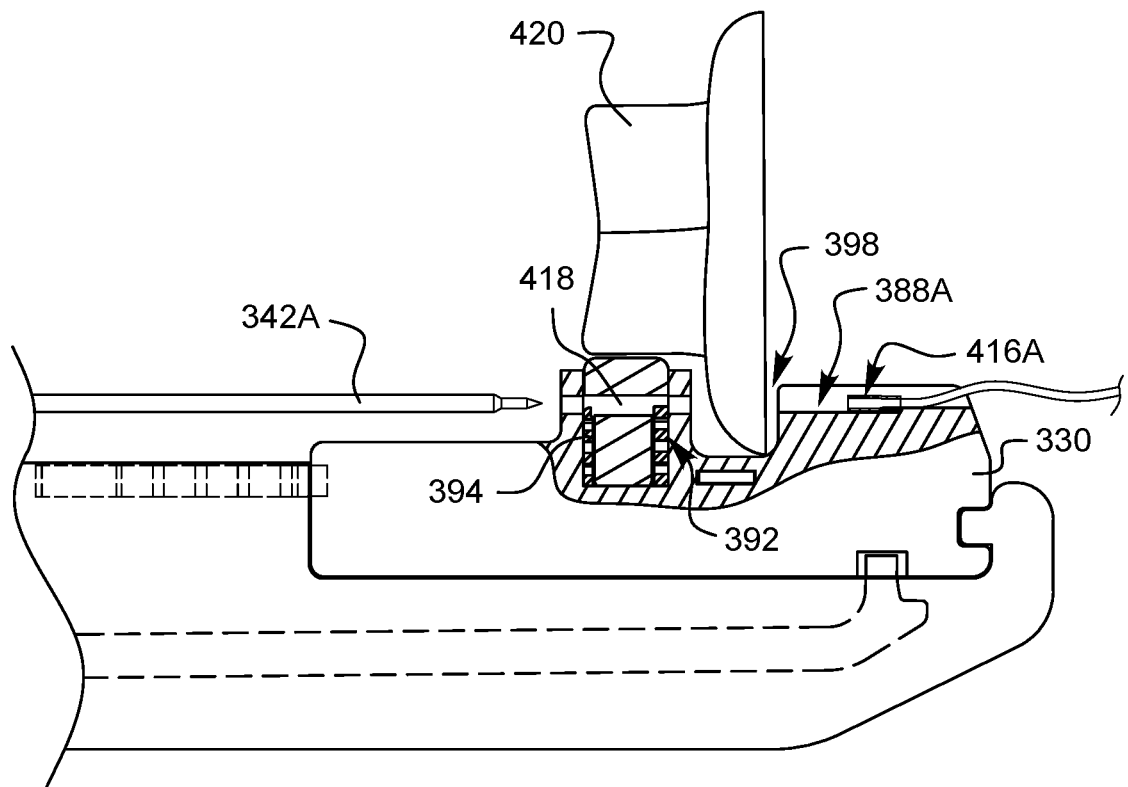
FIGS. 26A-26E are partial cross-sectional side views of the surgical suturing device and magazine of FIG. 20A being used to place a suture stitch in a sewing cuff of a replacement heart valve.

Ferrules may be loaded into the magazine either after, or preferably before, the magazine is inserted into the suturing device. FIG. 26A illustrates a partial cross-sectional side view of a magazine 330 having a ferrule 416A loaded into a suture holder 388A. The magazine 330 is loaded into the suturing device to the first suturing position, and the visible needle 342A is aligned with the ferrule 416A in the ferrule holder 388A. The ferrule remover 394 and the ferrule gate 392 are protruding slightly into a passage 418 of ferrule capture. A replacement anatomical device 420 (in this example, a replacement heart valve) has been placed into a sewing cuff receiver 398 of the magazine 330.

Figure 26B:
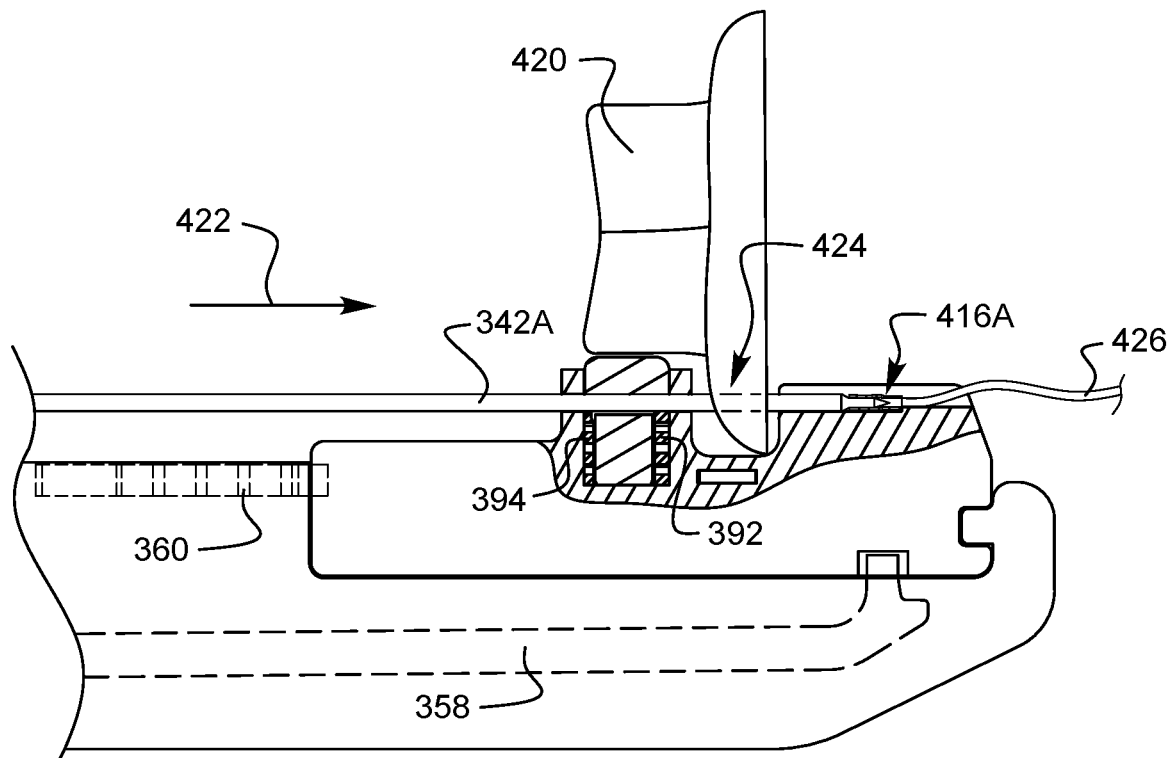

In FIG. 26B, the needle 342A has been actuated in a distal direction 422, causing it to pass against the ferrule remover spring 394 (pushing it down), pass through the passage 418 in the ferrule capture, pass against the ferrule gate spring 392 (pushing it down), pass through the sewing cuff 424 of the replacement valve 420, and into contact with the ferrule 416A at the end of the suture 426. In this embodiment, the tip of the needle fits within the ferrule and holds onto the ferrule.

Figure 26C:
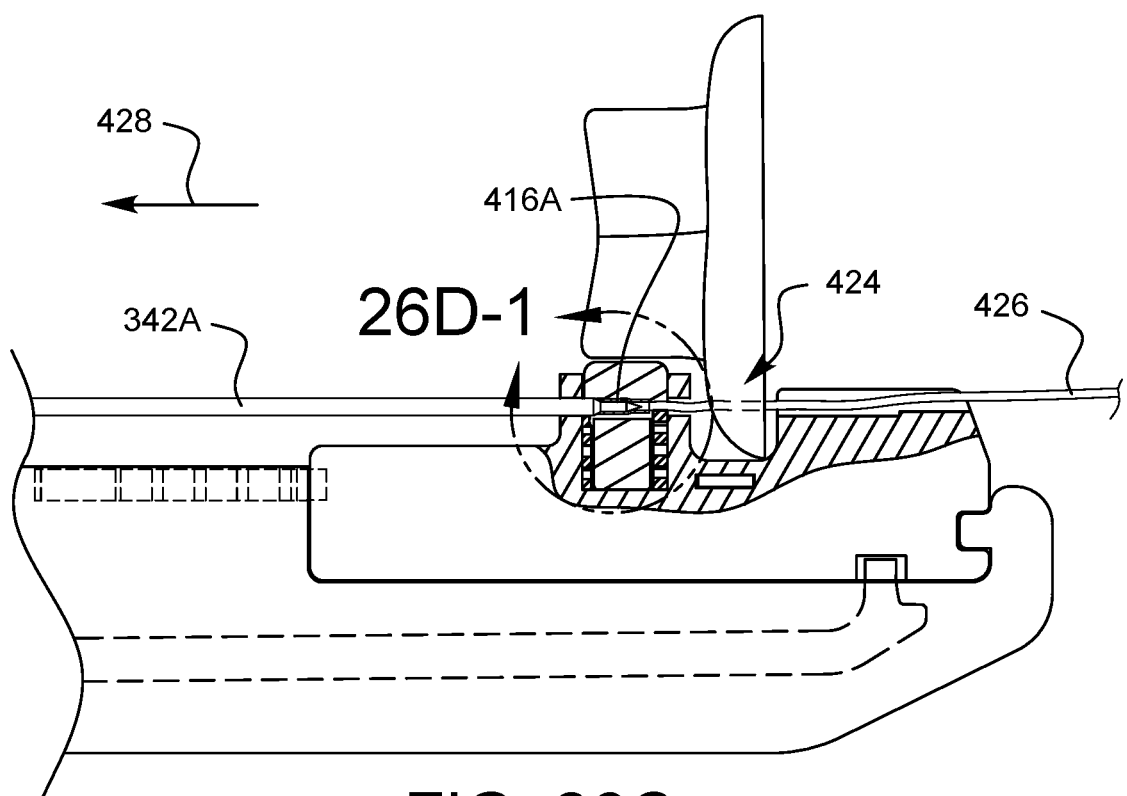
Figures 1, 26D:
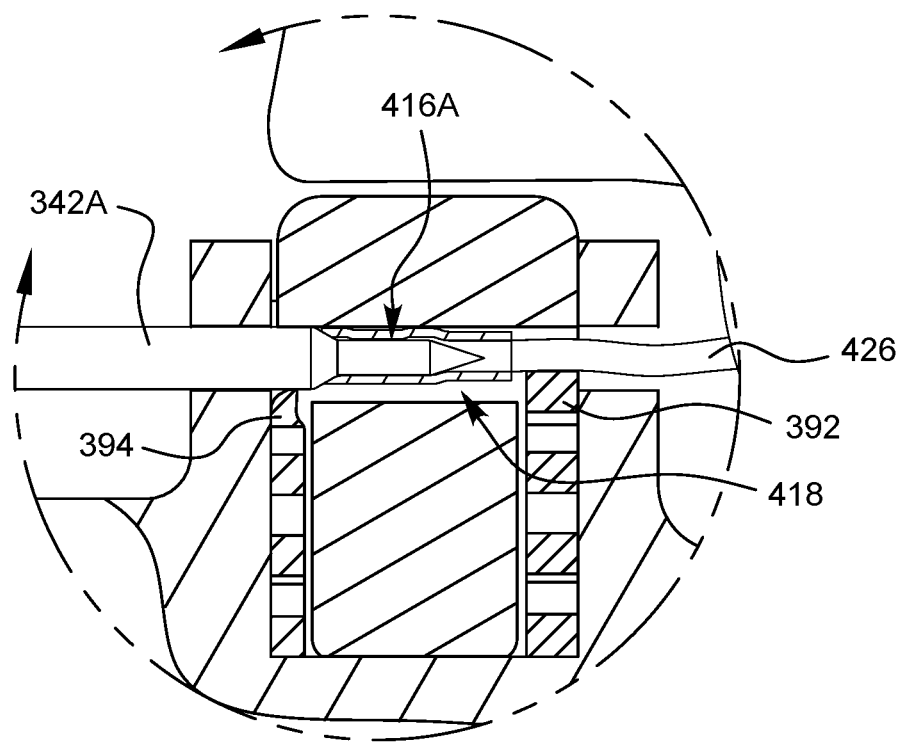
Figures 2, 26D:
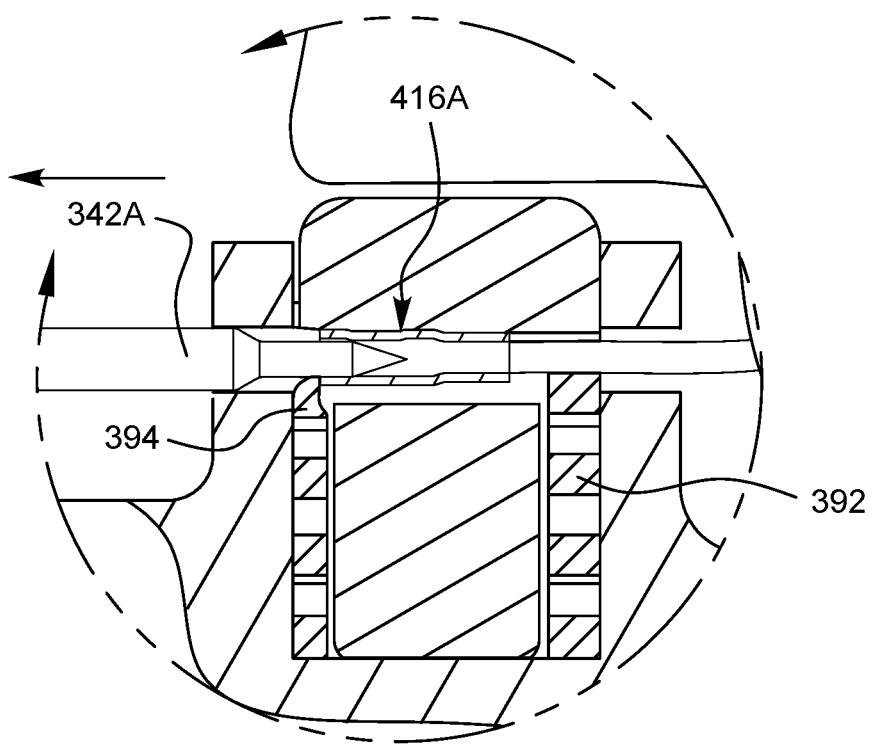
Figure 26E:
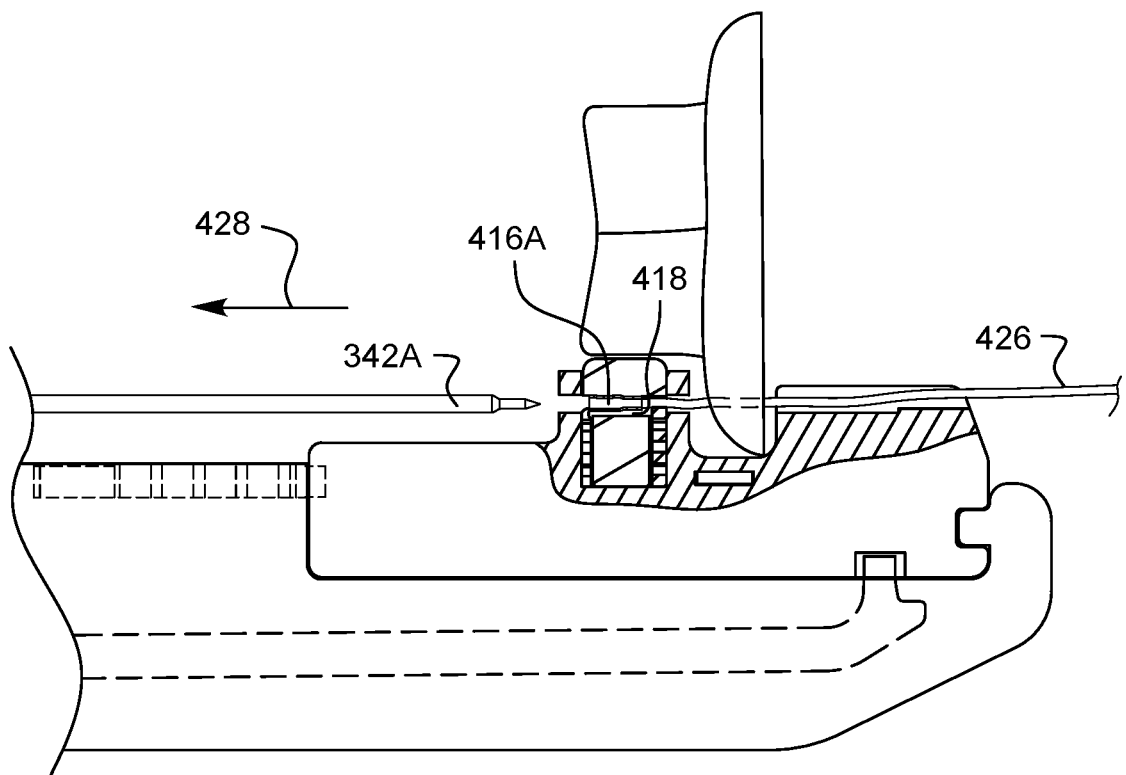

In FIG. 26C, the needle 342A has been partially withdrawn in a proximal direction 428 so that the ferrule 416A and its attached suture 426 are pulled back through the sewing cuff 424, over the ferrule gate spring 392, and into the passage 418 of the ferrule capture. The ferrule 416A held by the needle 342A tip in the ferrule capture 418 may be seen more clearly in the enlarged view of FIG. 26D-1. In the enlarged view of FIG. 26D-2, as the needle 342A continues in a proximal direction, an edge of the ferrule remover spring 394 catches on the lip of the ferrule 416A and starts to remove the ferrule 416A from the needle's 342A tip. As shown in FIG. 26E, as the needle 342A continues in the proximal direction 428, the ferrule 416A is completely removed from the needle 342A and held in the ferrule capture 418. The ferrule trap ensures that the ferrule does not pull back out of the ferrule capture 418, even if the suture 426 attached thereto is pulled.

Figure 27A:
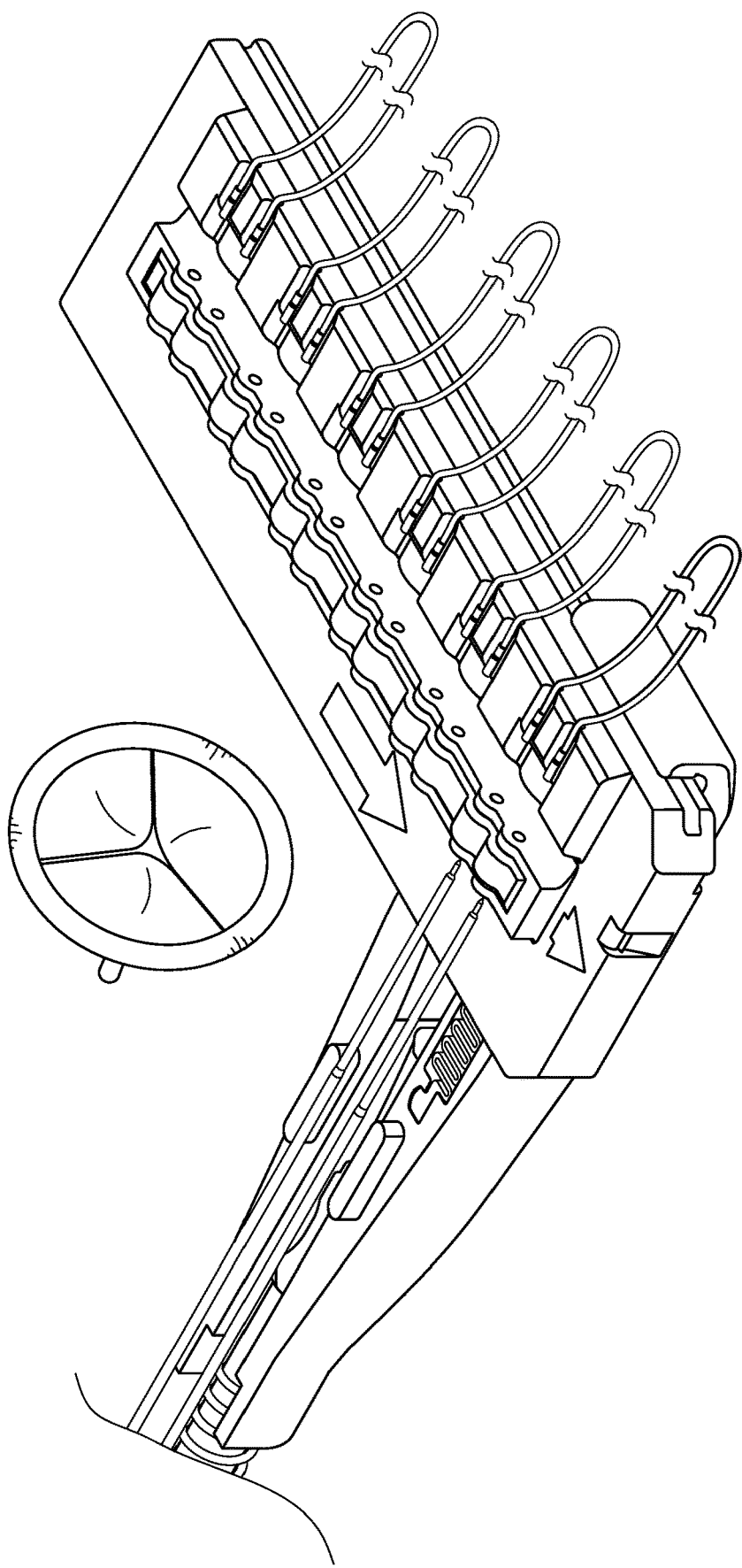
Figure 27B:
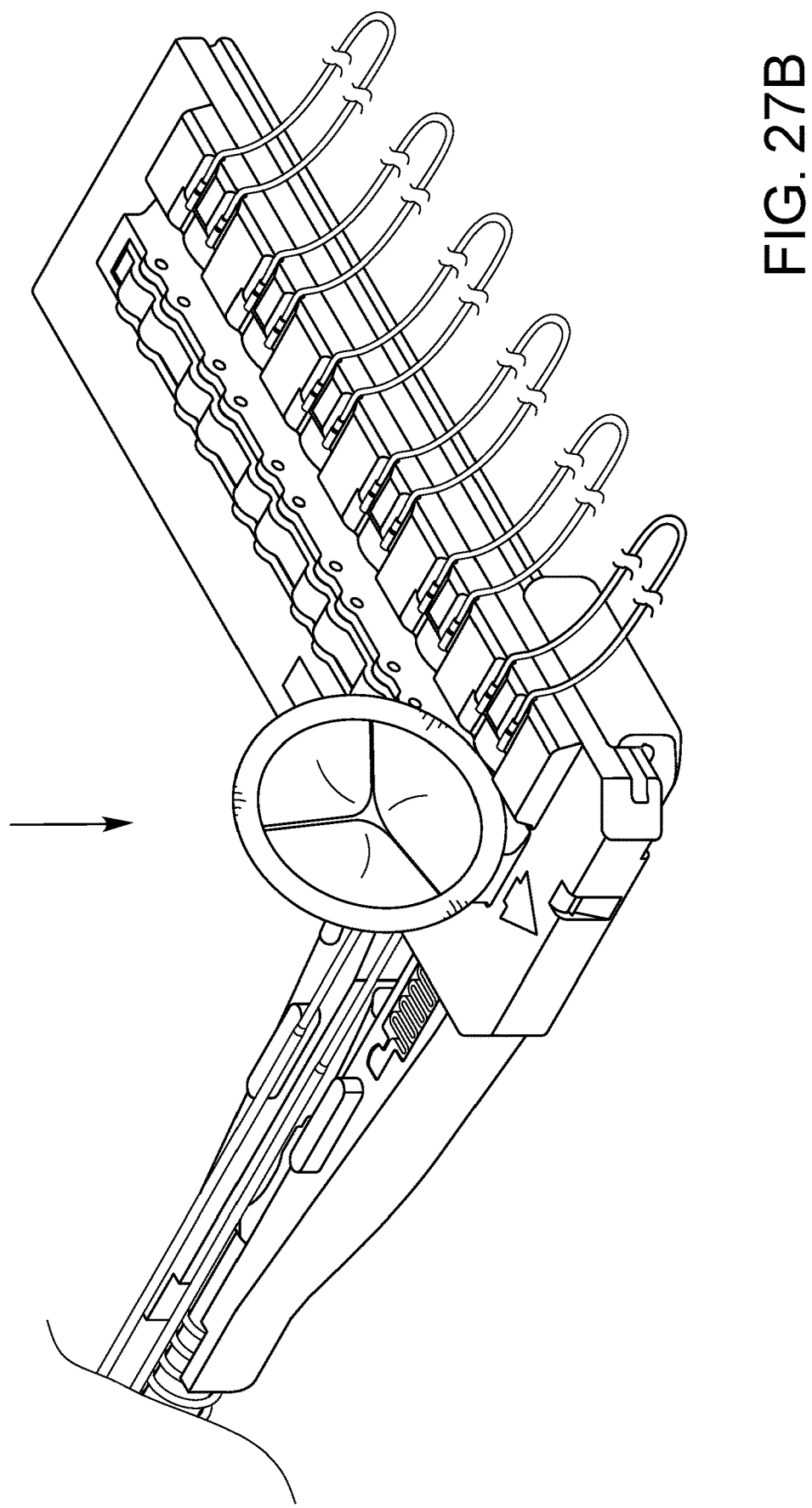
Figure 27D:
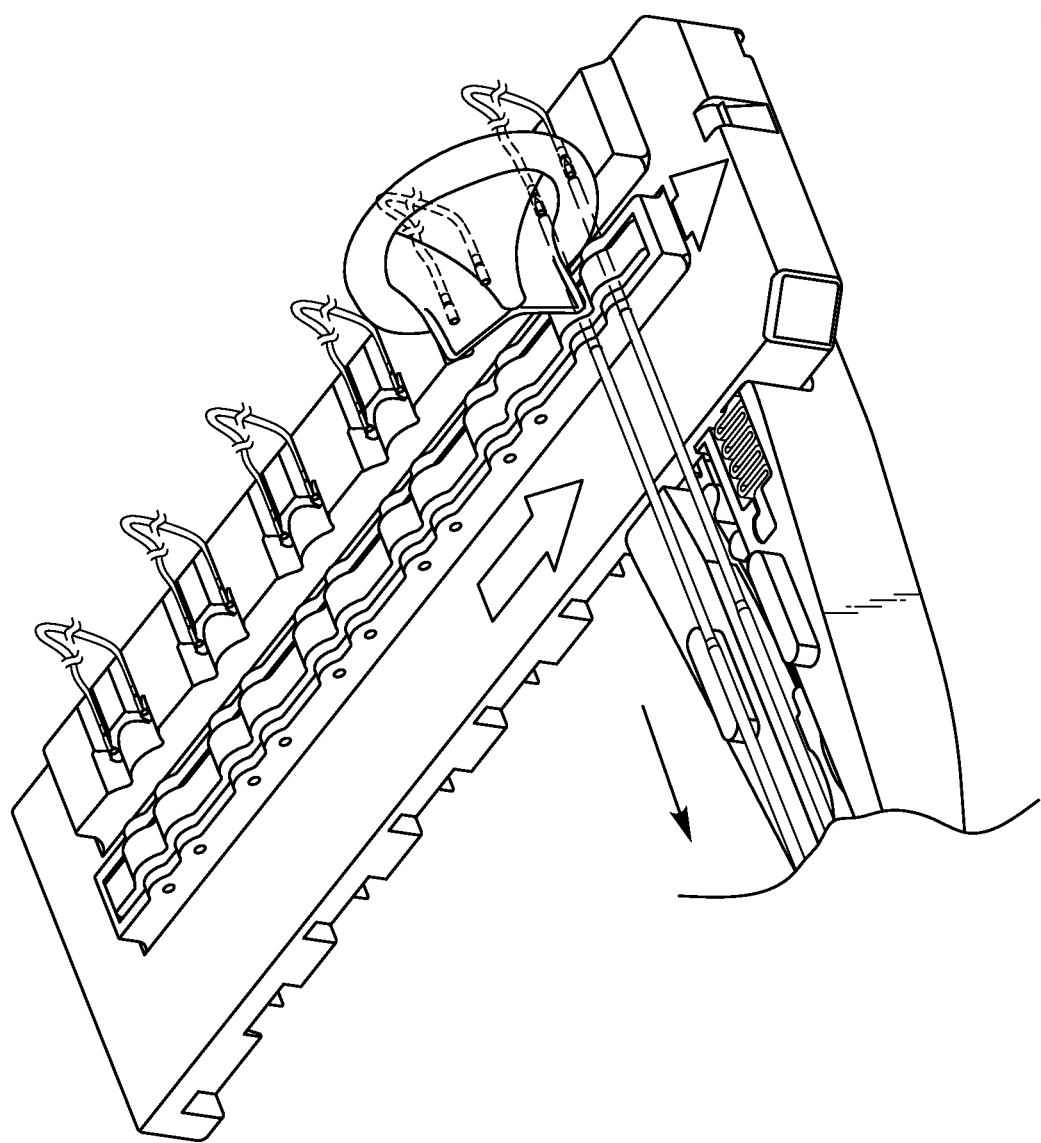
Figure 27E:
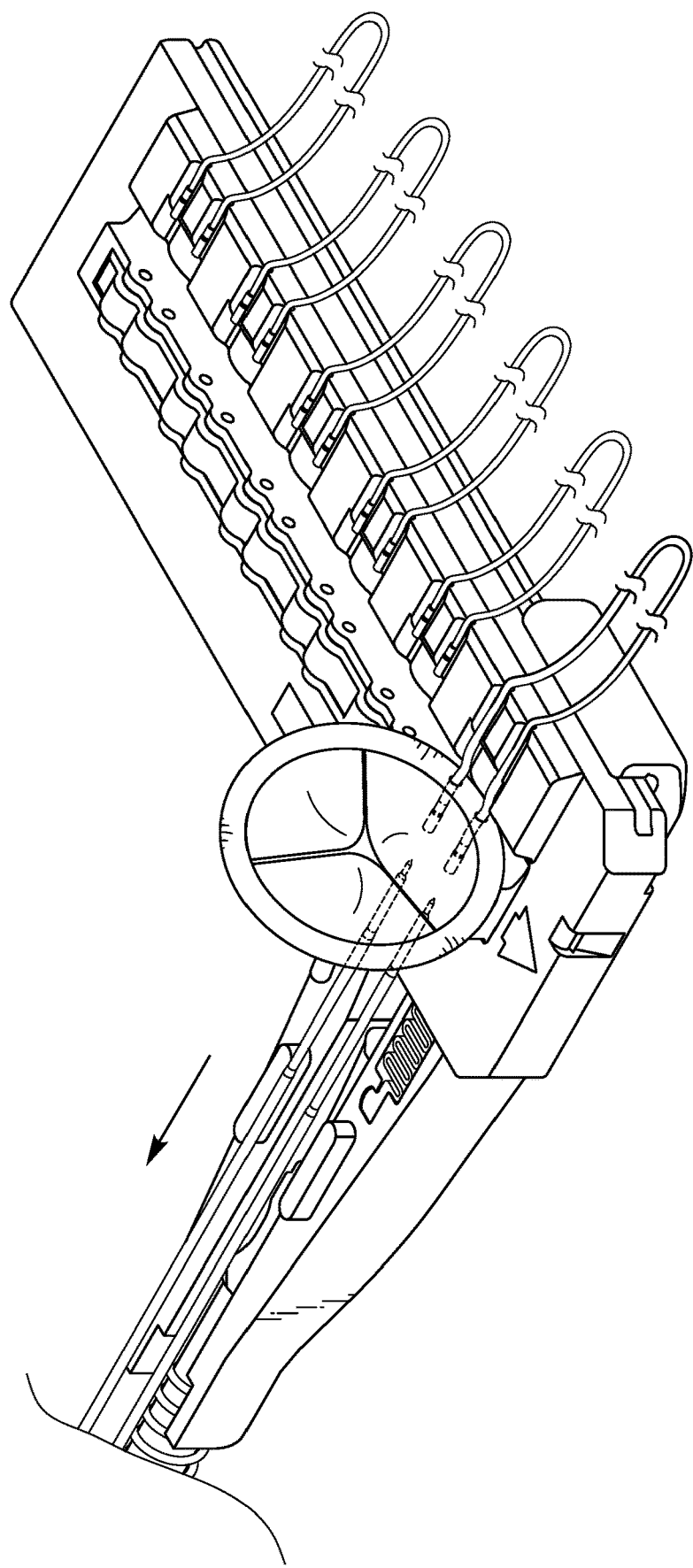
Figure 27F:
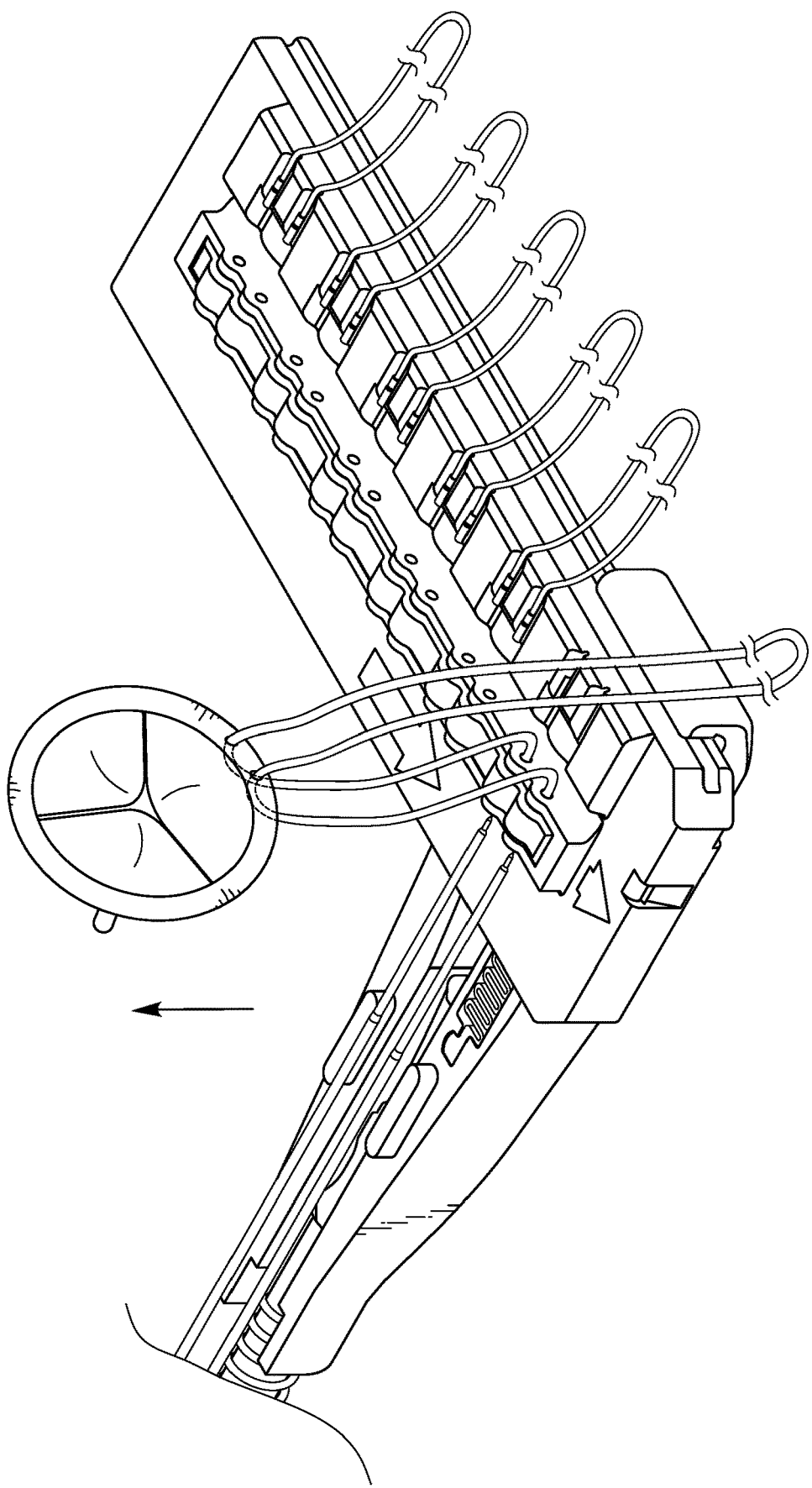
Figure 27G:
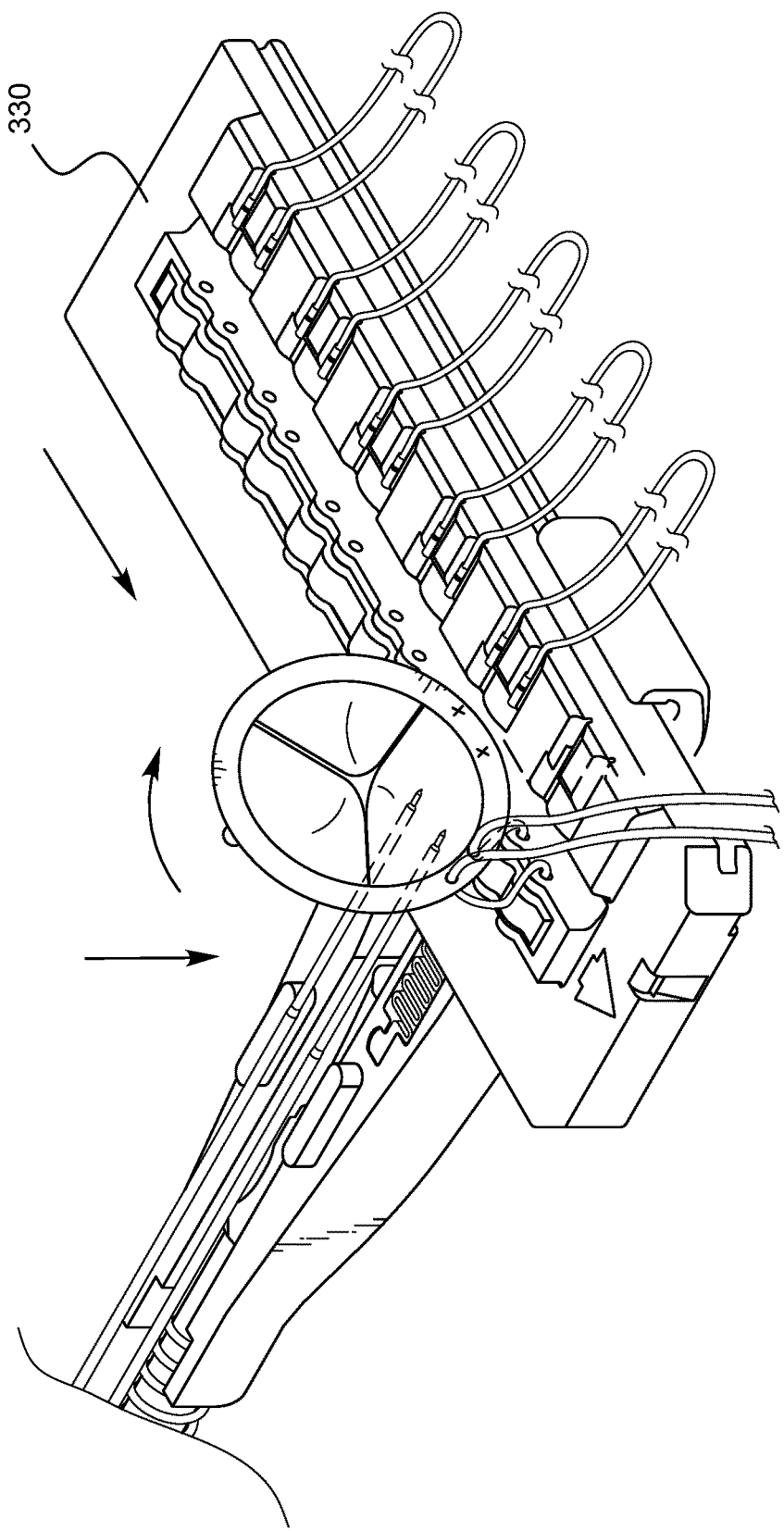

FIGS. 27A-27H show a similar sewing process for a single suturing position in a partially exposed view which highlights the dual needle embodiment. FIG. 27G illustrates the magazine 330 having been indexed to a second suturing position, and the replacement valve is being rotated and placed back into the sewing cuff receiver so that the needles may penetrate the sewing cuff at another position to pull the second suture set back through. The second stitch would occur much like the first, just with a second set of ferrules attached to the ends of a second suture.

FIGS. 28A-28G schematically illustrate one embodiment of how the indexer portion of the suturing device and the indexable feature of the magazine work together to index or move the magazine from one suturing position to another. The viewpoint of FIGS. 28A-28G is from the bottom of the device, and for clarity, the device tip is shown as being transparent with visible edges so the features of the magazine behind it may more clearly be seen with solid lines. For simplicity, certain portions of the device are not shown in FIGS. 28A-28G to provide clarity to the explanation.

Figure 28A:
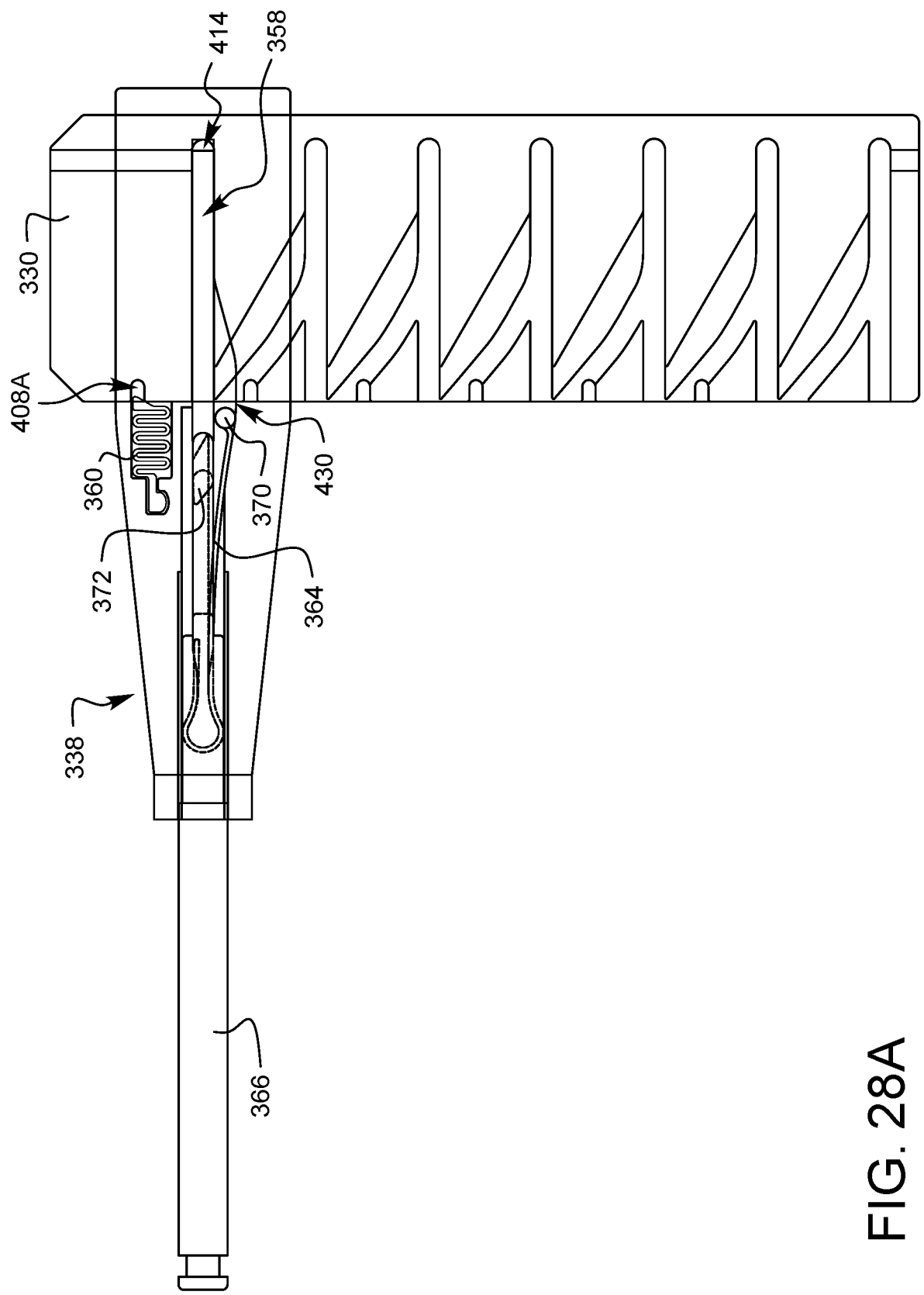
FIGS. 28A-28G schematically illustrate one embodiment of how the indexer portion of the suturing device and the indexable feature of the magazine work together to index or move the magazine from one position to another.

In FIG. 28A, the primary cam 370 of the indexing flexure 364 is seen resting in its track 430 of the device tip 338 in a retracted position, while the pusher 366 and the secondary cam 372 coupled to it are also in retracted positions. We can tell the magazine 330 is in a first suturing position because the stop spring 360 is engaged in the first stop receiver 408A on the side of the magazine. The tip 414 of the forward stop 358 is also engaging a depression in the magazine.

Figure 28B:
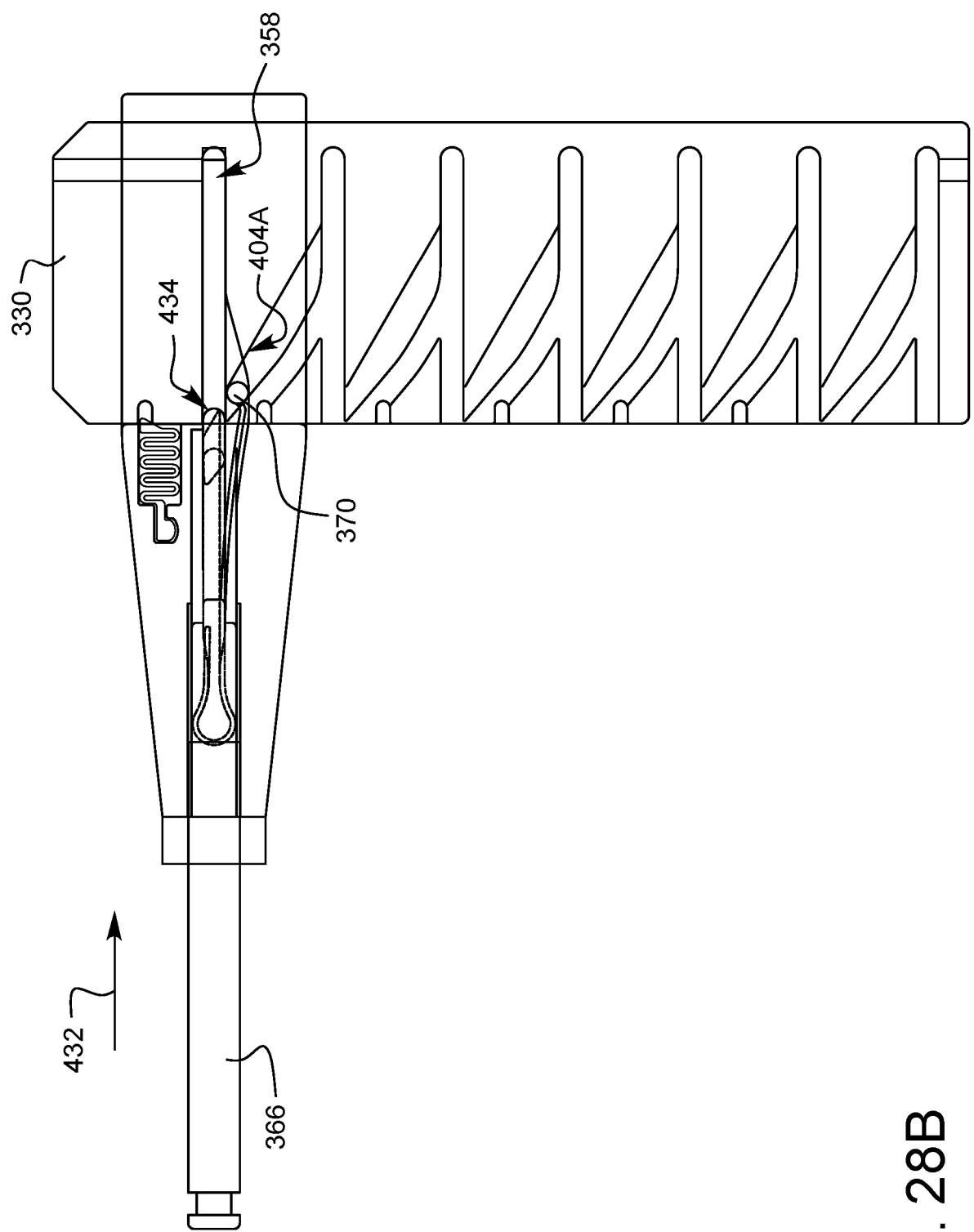

In FIG. 28B, the pusher 366 has started to move in a distal 432 direction, causing the primary cam 370 to move into contact with the primary cam path 404A of the magazine 330. Additionally, the forward portion 434 of the pusher 366 engages the forward stop 358, pushing it out of engagement with the magazine 330 (This movement of the forward stop 358 is towards the viewer in the orientation of FIG. 28B, away from the magazine 330 so that the tip of the forward stop no longer engages the depression in the magazine).

Figure 28C:
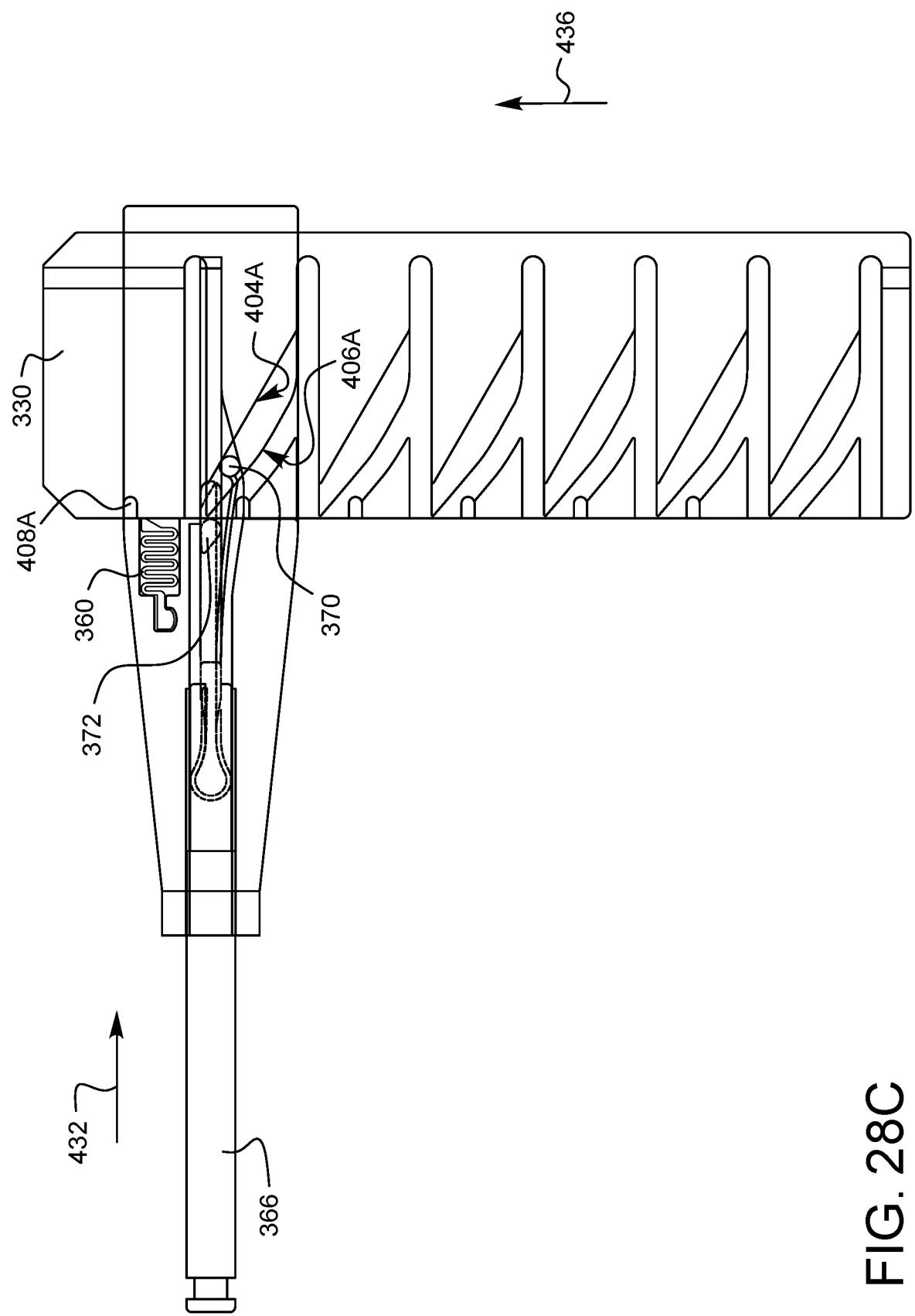

In FIG. 28C, the pusher 366 continues to move distally 432, and the interference of the primary cam 370 with a ramped wall of the primary cam path 404A causes the magazine 330 to start to move in a direction lateral 436 to the pusher movement The secondary cam 372 on the pusher 366 also is aligned to enter the secondary cam path 406A defined by the magazine 330. Since the magazine 330 is moving, the stop spring 360 has been pushed out of the stop receiver 408A in the magazine 330.

Figure 28D:
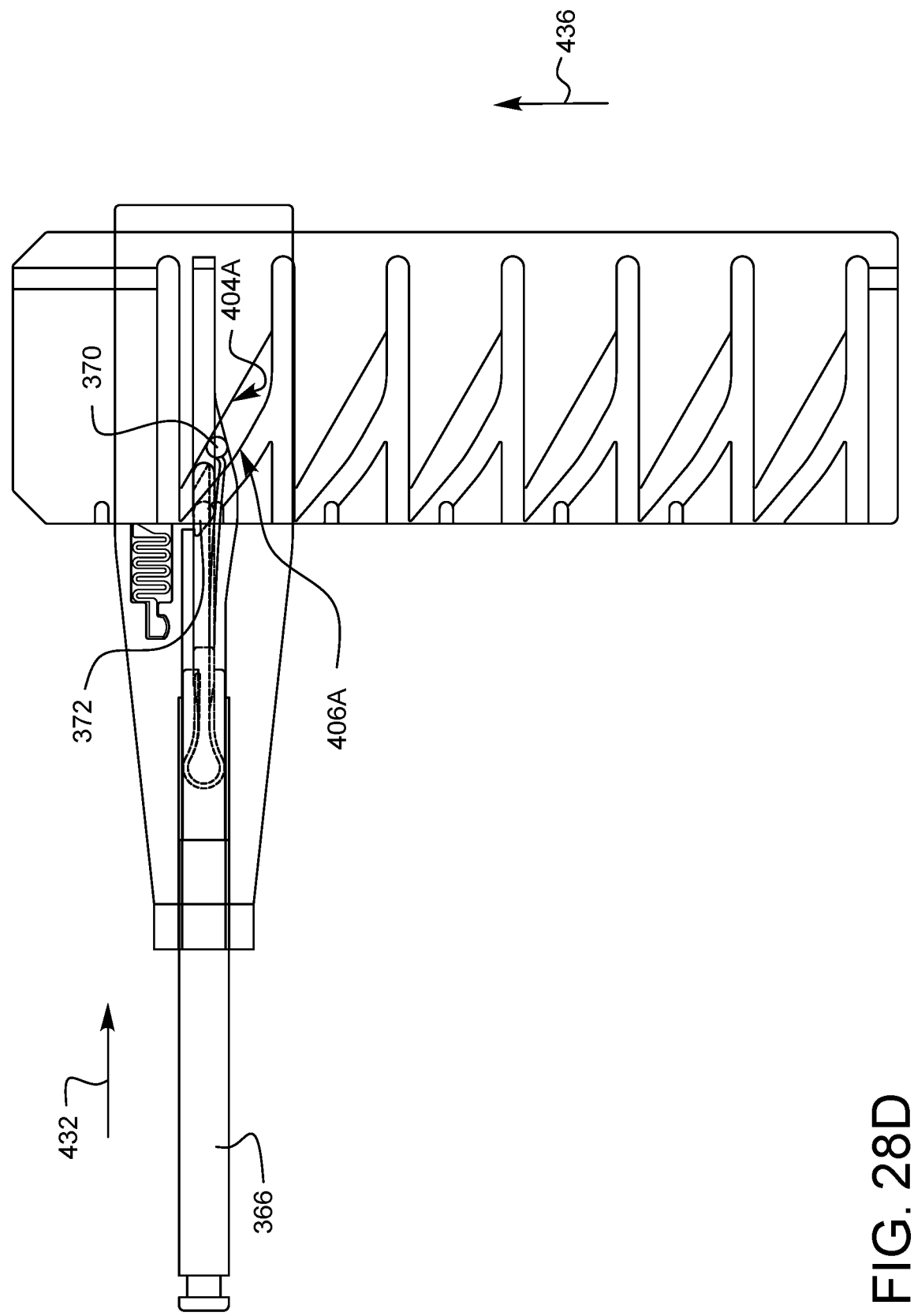
Figure 28E:
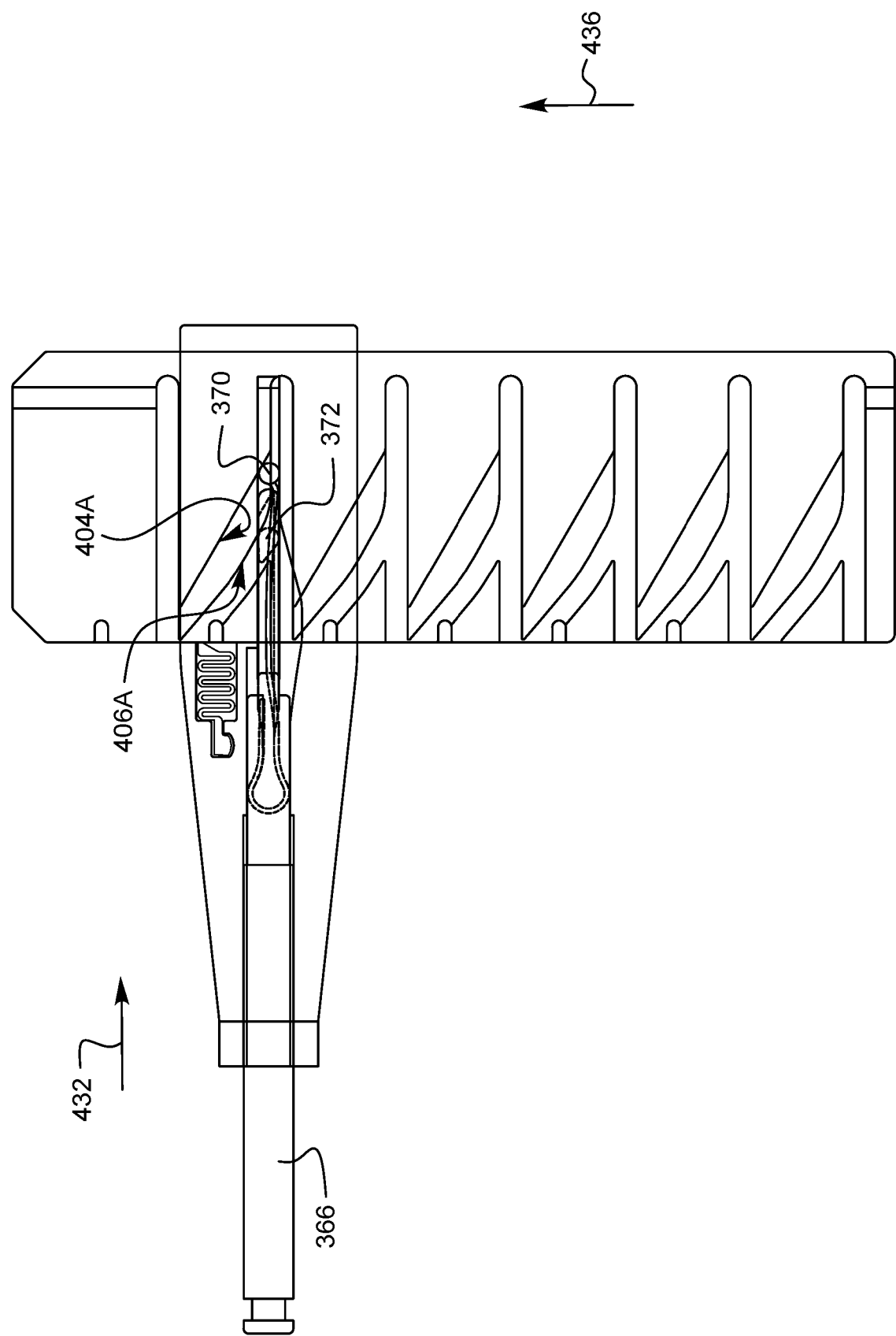

In FIGS. 28D and 28E, the pusher 366 continues moving in a distal direction, causing the primary and secondary cams 370, 372 to move down the primary and secondary cam paths 404A, 406A, respectively, resulting in more lateral movement 436 of the magazine.

Figure 28F:
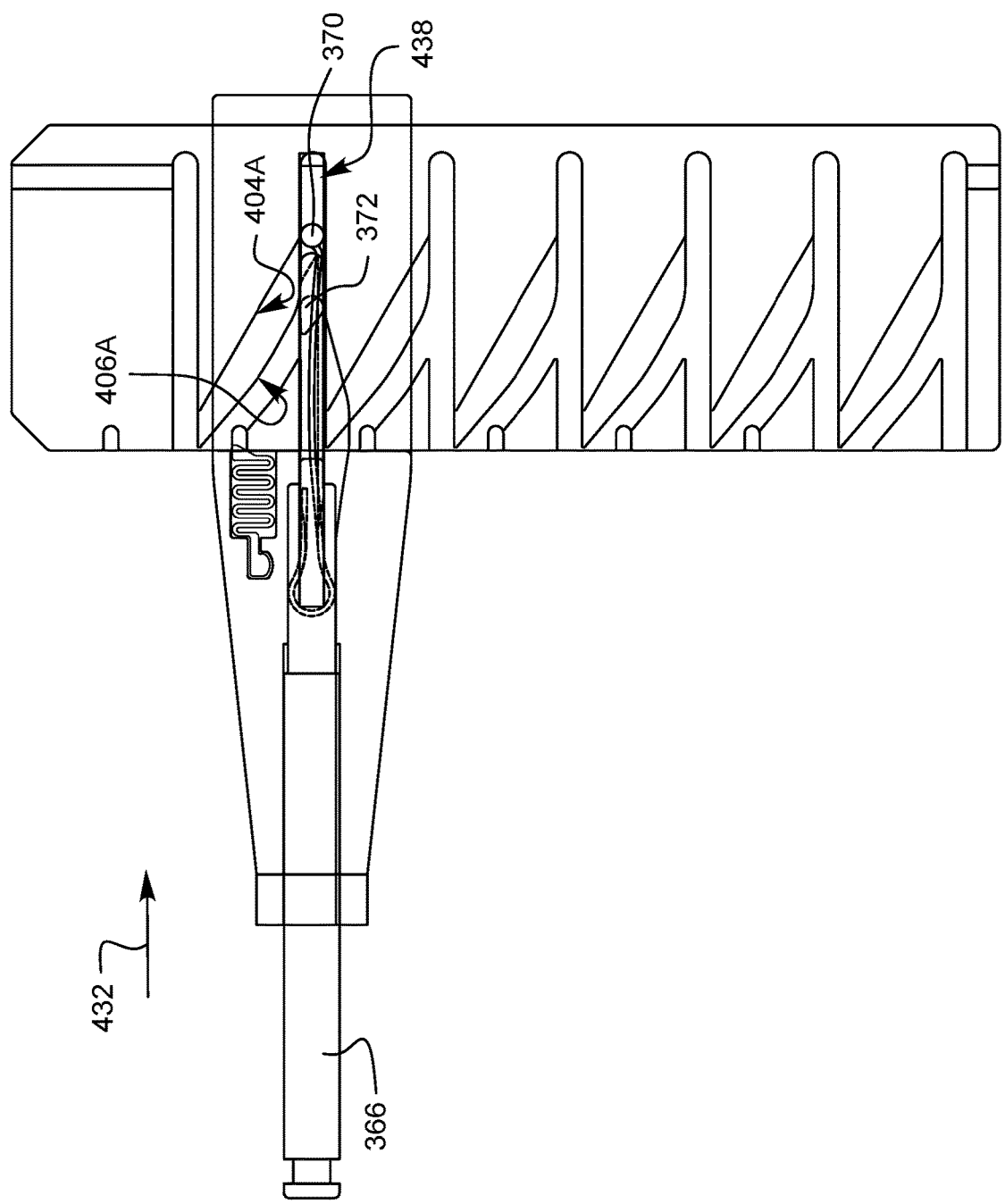
Figure 28G:
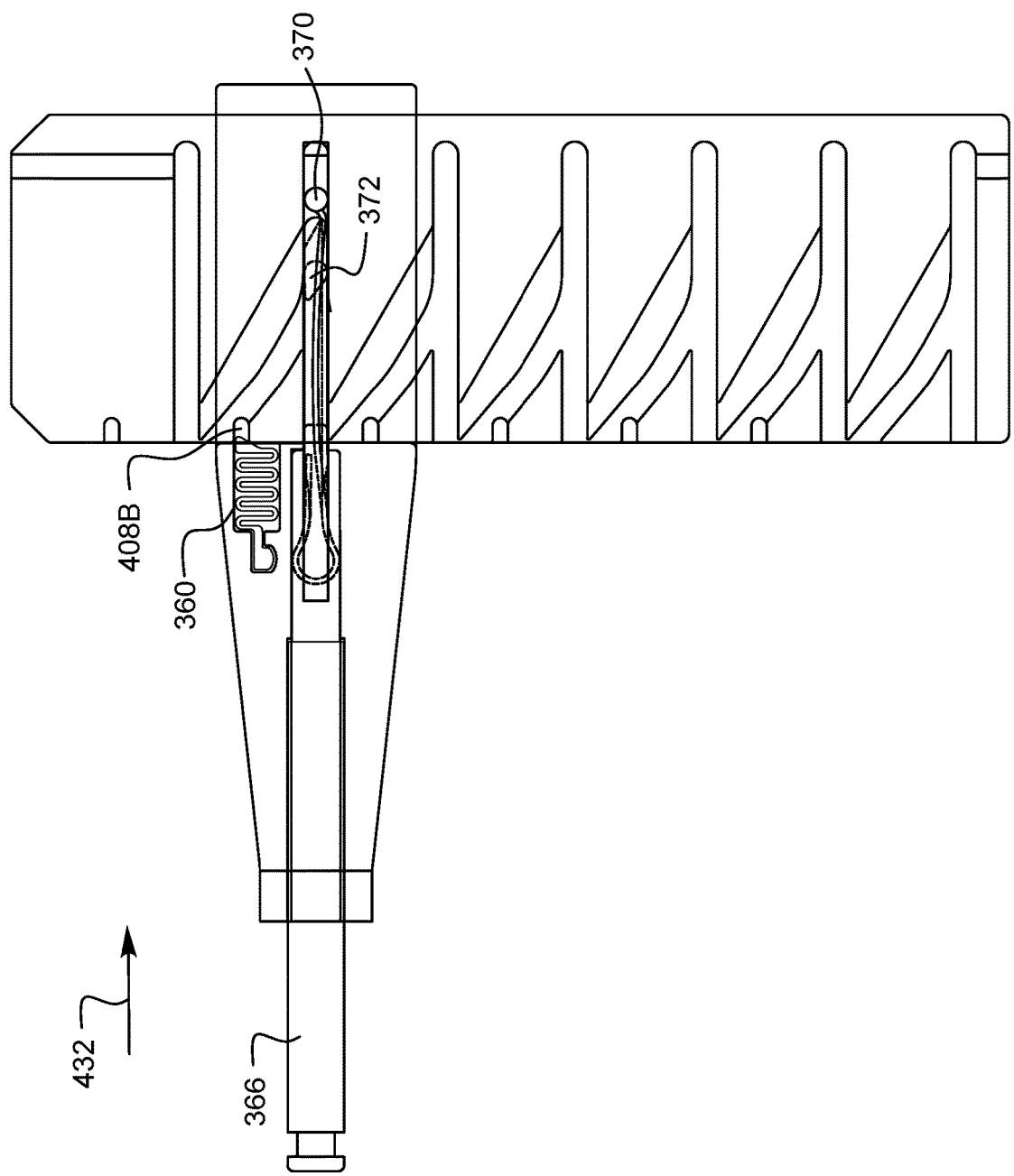

In FIG. 28F, the pusher 366 continues moving in a distal direction 432, causing the primary and secondary cams 370, 372 to move onto respective portions of the primary and secondary cam paths 404A, 406A which are parallel 438 to the motion of the pusher 366. At this point, the lateral movement of the magazine will stop, even if the pusher 366 continues to move forward as in FIG. 28G. The stop spring 360 has engaged the second stop receiver 408B, and the indexing movement has been accomplished in this embodiment with just the distal movement of the pusher 366. Although not shown in this view, the needles are now aligned with the second set of ferrules in the second suturing position. If pressure on the pusher 366 is released, the pusher spring (not shown here) will retract the pusher and the primary and secondary cams 370, 372. The indexing may then be repeated as desired.

Thus far, all of the illustrated embodiments show separate controls for needle actuation and indexing. The handle lever actuates the needles and the push button (coupled to the pusher) causes a magazine to index. However, as will be apparent to those skilled in the art, it is possible to have both functions controlled by a single actuator. As one example, energy could be stored in an energy storage spring as the lever is squeezed. Then, as the lever is released, and once the needles were clear of the magazine, the energy stored in the storage spring could be used to drive the indexing movement. In other embodiments, movement of the lever in a first direction could engage the needles, which might be spring biased to automatically retract at the end of a lever stroke. Movement of the lever back to the starting direction could cause indexing to occur.

Furthermore, the indexing and needle actuation could be accomplished in a wide variety of other ways. All manner of alternatives will be apparent to those skilled in the art upon reading this specification. As some non-limiting examples, the actuator or the indexer may include one or more levers, gears, pulleys, friction wheels, solenoids, motors, or any combination thereof. When those skilled in the art consider other actuator embodiments, such as electronically controlled actuators, many ways will become apparent for a single "actuator", from the user's point of view, to instigate the needle actuation and the magazine indexing, rather than having two manual controls.

Figure 29:
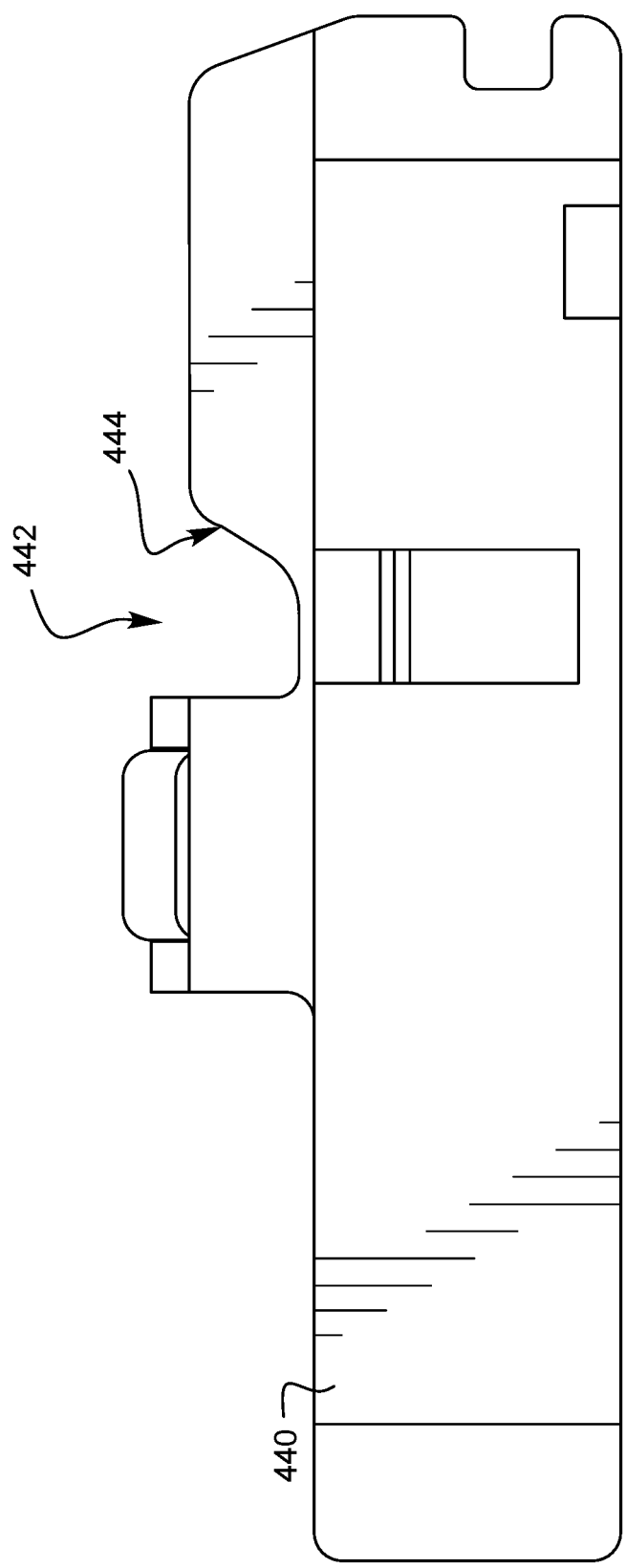
FIG. 29 is a side view of another embodiment of a magazine for a suturing device.

FIG. 29 is a side view of another embodiment of a magazine 440 for a suturing device. While the sewing cuff receiver of the previously discussed embodiments was symmetrical from a side view, this embodiment has an asymmetrical sewing cuff receiver 442 when viewed from this side view. Depending on the embodiment, the shape of the sewing cuff receiver 442 may be designed to conform to the shape of a particular sewing cuff. In some embodiments, the sewing cuff receiver may have a ramp 444, curve, or slope to enable surgeons to prop the sewing cuff inserted therein at a desired height, thereby offering surgeons more control over suture placement.

FIGS. 30A, 31A, 32A, and 33A schematically illustrate different side views of a suture magazine receiver 446, 448, 450, 452, respectively, in a suturing device (only the device tip is pictured). Each of the different embodiments in FIGS. 30A, 31A, 32A, and 33A has a magazine receiver with a differing number of receiving surfaces. The magazine receiver 446 of FIG. 30A has four receiving surfaces 446A, 446B, 446C, 446D. The magazine receiver 448 of FIG. 31 has three receiving surfaces 448A, 448B, 448C. The magazine receiver 450 of FIG. 32A has two receiving surfaces 450A, 450B. The magazine receiver 452 of FIG. 33A has one receiving surface 452A. The receiving surfaces can help guide a magazine when inserted therein. FIGS. 30A, 31A, 32A, and 33A also include different embodiments of magazine mating features 454, 456, 458, 460, 462. The magazine mating features can be protruding 454, 456, 458, 460, or they can be inset 462, or any combination thereof. Any number (zero or greater) of magazine mating features may be included in the magazine receiver. The magazine mating features may have any desired shape, and not all mating features need to be used for any given magazine, depending on the embodiment. This might enable a single suturing device to interact with different magazines having a variety of different corresponding mating features.

Figure 30A:
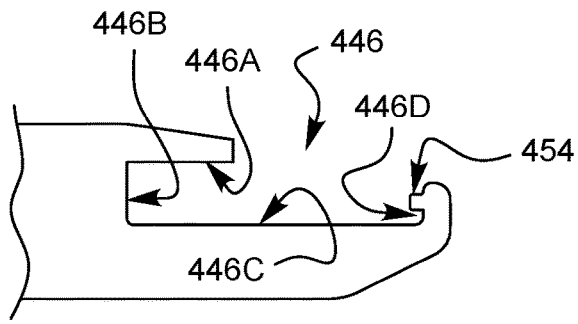
FIGS. 30A-33B schematically illustrate side views of different suture magazine receivers and corresponding magazines for use in a suturing device.
Figure 30B:
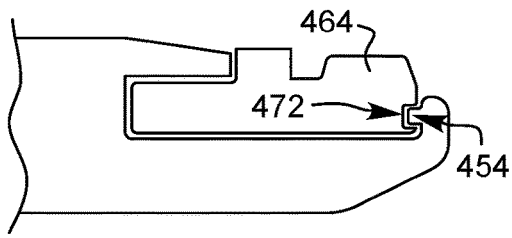
Figure 31A:
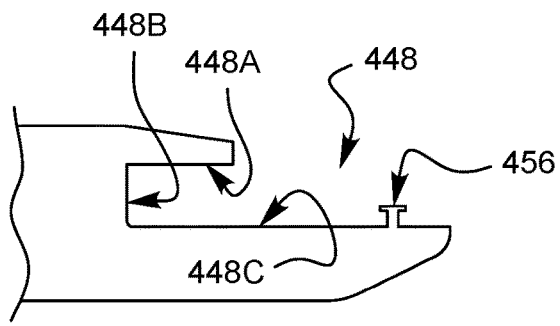
Figure 31B:
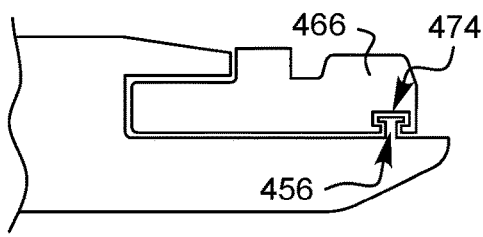
Figure 32A:
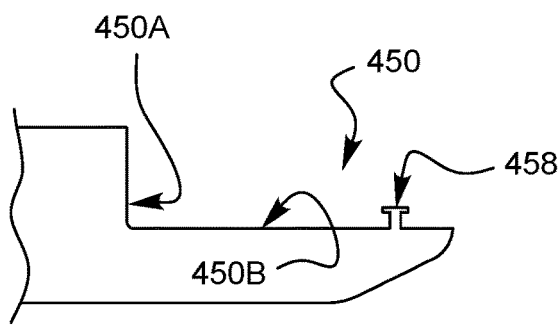
Figure 32B:
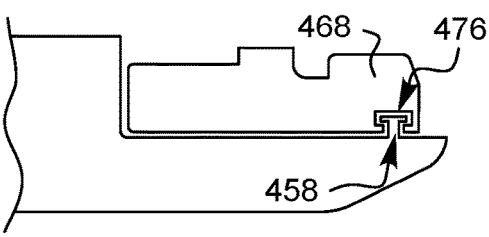
Figure 33A:
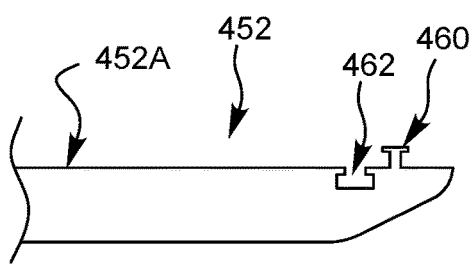
Figure 33B:
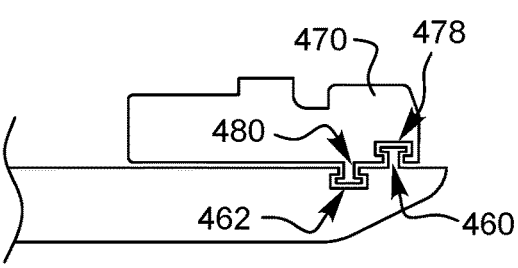

FIG. 30B illustrates one embodiment of a suture magazine 464 installed in the suture magazine receiver of FIG. 30A. FIG. 31B illustrates one embodiment of a suture magazine 466 installed in the suture magazine receiver of FIG. 31A. FIG. 32B illustrates one embodiment of a suture magazine 468 installed in the suture magazine receiver of FIG. 32A. FIG. 33B illustrates one embodiment of a suture magazine 470 installed in the suture magazine receiver of FIG. 33A. Each magazine in FIGS. 30B, 31B, 32B, and 33B has one or more receiver mating features which correspond to the magazine mating features of the magazine receiver. For example, magazine 464 has receiver mating feature 472 which corresponds to magazine mating feature 454. Magazine 466 has receiver mating feature 474 which corresponds to magazine mating feature 456. Magazine 468 has receiver mating feature 476 which corresponds to mating feature 458. Magazine 470 has receiver mating features 478, 480 which correspond to magazine mating features 460, 462, respectively.

Figure 34A:
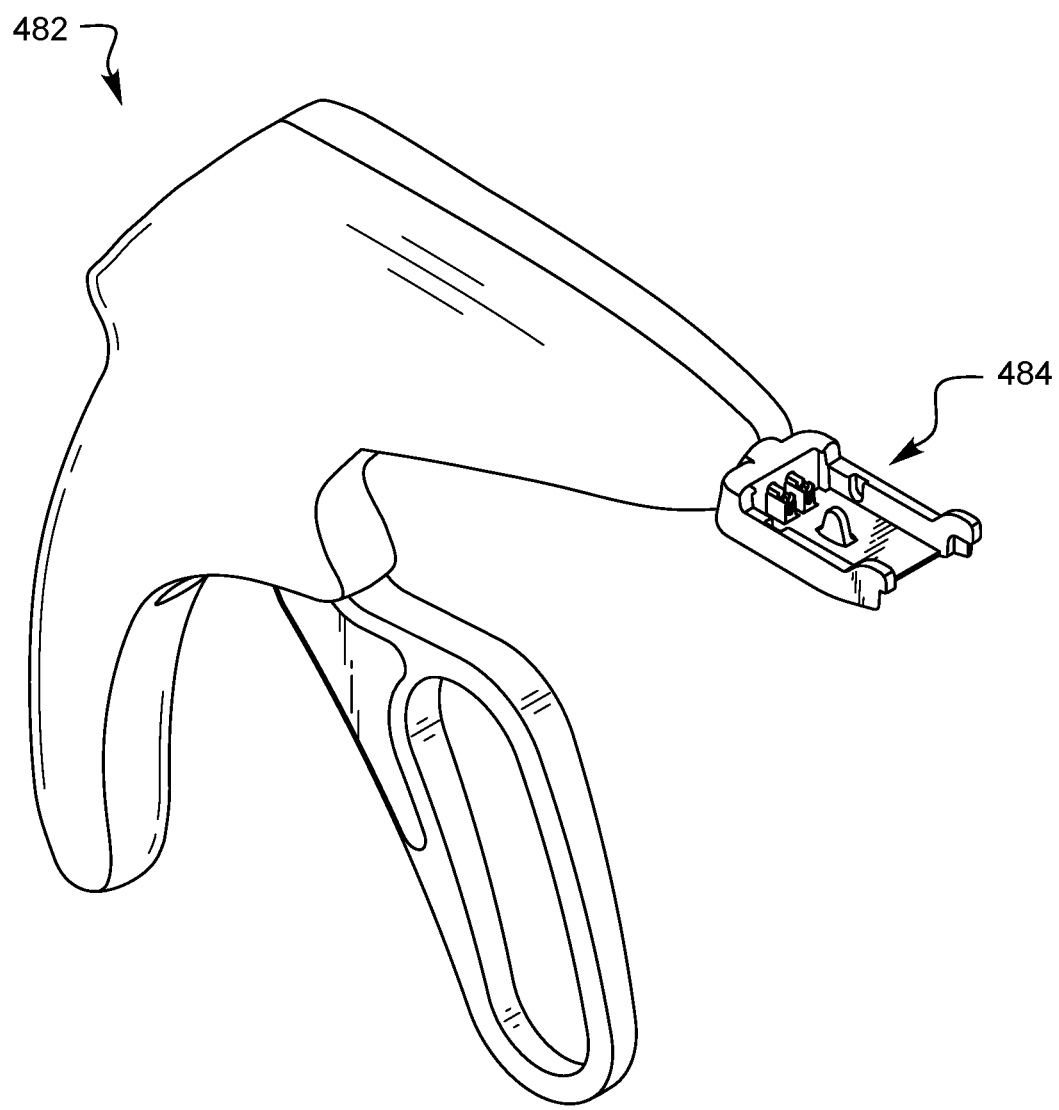
FIG. 34A illustrates one embodiment of a surgical suturing device having a cassette receiver.
Figure 34B:
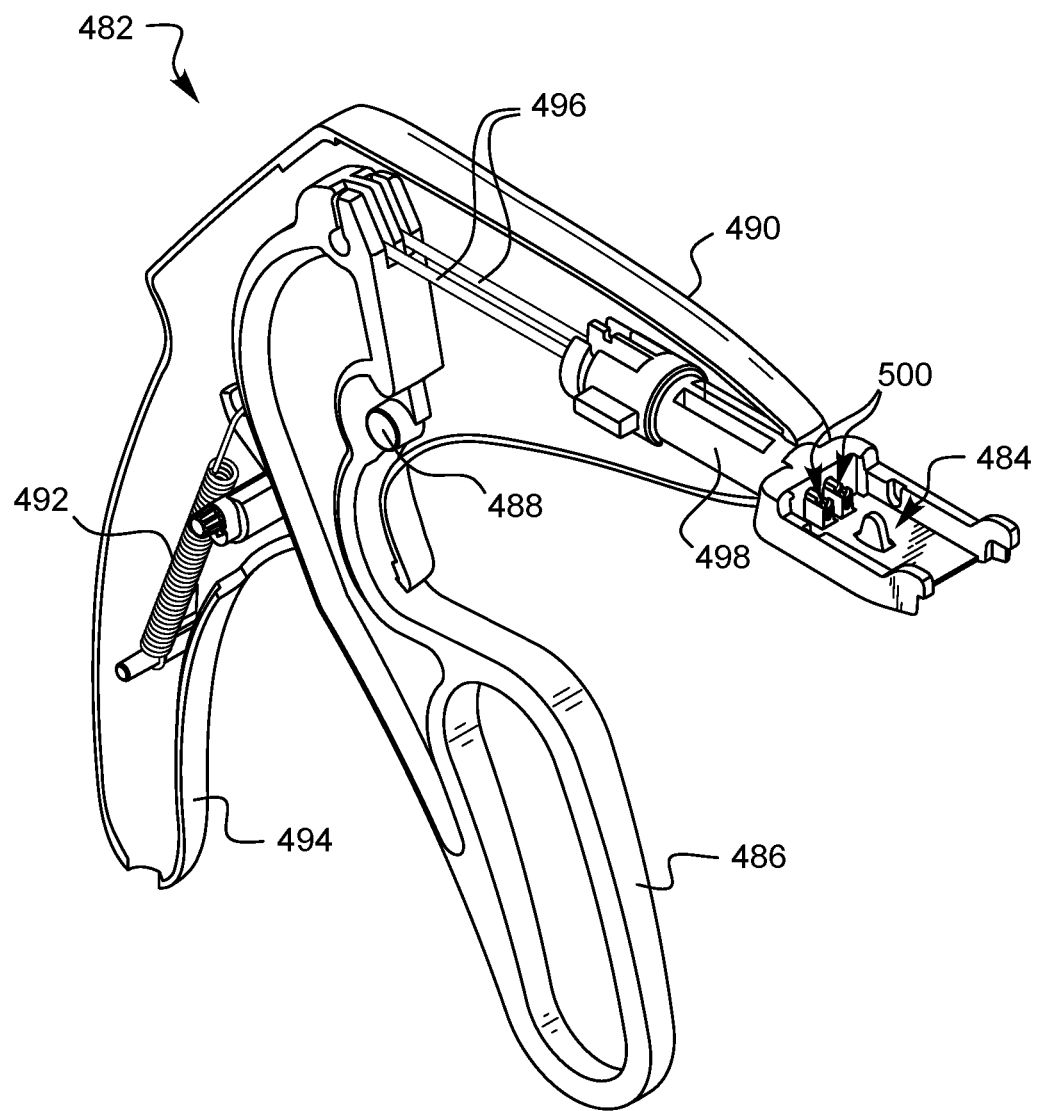
FIG. 34B is the surgical suturing device of FIG. 34A in a partially exposed view.

FIG. 34A illustrates one embodiment of a surgical suturing device 482 having a cassette receiver 484. FIG. 34B is the surgical suturing device 482 of FIG. 34A in a partially exposed view. A handle 486 is pivotable around a pivot point 488 supported by the housing 490. A spring 492 coupled between the handle 486 and the housing 490 biases the handle 486 away from a grip 494. Two needle drivers 496 are coupled to the handle 486. The needle drivers 496 extend through a receiver component 498, ending in a cassette receiver 484. The ends 500 of the needles drivers 496 are visible in the cassette receiver 484.

Figure 35:
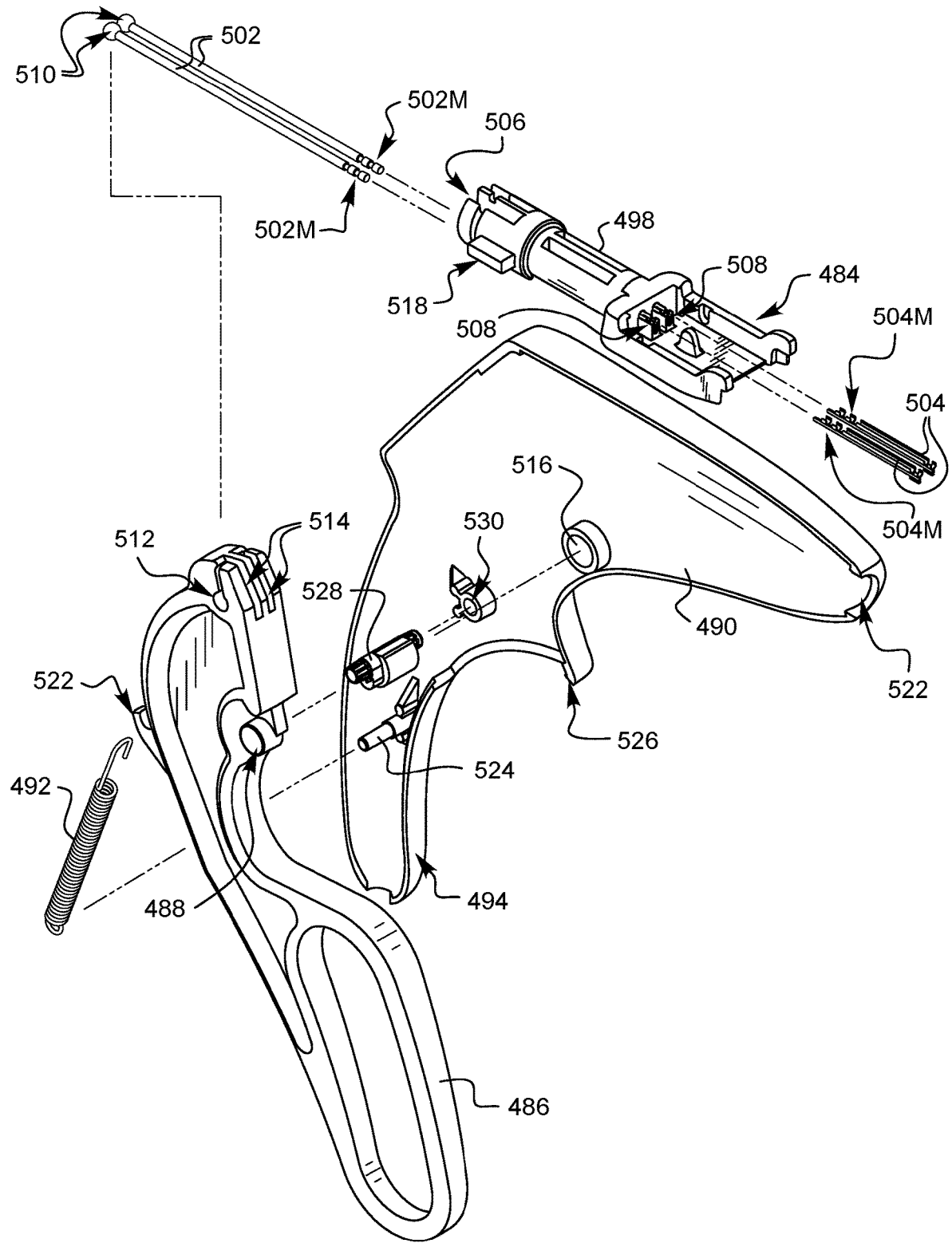
FIG. 35 is an exploded view of the surgical suturing device of FIG. 34A.

FIG. 35 is an exploded view of the surgical suturing device of FIG. 34A. The needle drivers in this embodiment each have two components: a proximal component 502 for coupling to the handle 486 and a distal component 504 that connects to the proximal component. There are two sets of proximal and distal components 502, 504 which make up the needle drivers. Each proximal component 502 has a first mating feature 502M which is passed through an opening 506 in the receiver component 498. Each distal component 504 of the needle drivers has a second mating feature 504M which is inserted into a corresponding guide slot 508 in the cassette receiver 484 side of the receiver component 498 where the respective mating features 502M, 504M for each needle driver are then coupled together inside the receiver component 498.

Each proximal component 502 of the needle drivers has a respective ball 510 which is fits into a respective hole 512 of the handle 486 while the proximal components 502 are in an upright position (perpendicular to the orientation shown in FIG. 35). Only one of the holes 512 is visible in this view, but the other hole 512 is symmetrically placed on the opposite side of the handle 486. Once the balls 510 have been placed into the holes 512, the proximal components 502 of the needle drivers can be maneuvered down into slots 514. The pivot point 488 extends to both sides of the handle 486 and is aligned within a pivot boss 516 of the housing 490. The receiving component 498 has features 518 (one of which is visible in this view) which are configured to be held by corresponding features in the housing 490. Such alignment features are known to those skilled in the art and are not shown in the housing 490 for simplicity. The housing 490 also has an opening 520 which is configured to help align the receiver component 498. The spring 492 is attached between a hook 522 on the handle 486 and a post 524 which is part of the housing 490. The spring 492 pulls on the hook 522, causing the handle 486 to rotate around the pivot point 488 until the handle 486 contacts a stop 526 on the housing 490. When in use, the handle 486 will be squeezed towards the grip 494. A motion limiter 528 is installed into a corresponding receiver 530 in the housing 490. The motion limiter 528 provides a limit to the range of motion of the squeezed handle 486. Only one half of the housing 490 is shown in the exploded view of FIG. 35, but a corresponding half (not shown) aligns with the pivot point 488, the motion limiter 528, and the receiver component 498 while coupling to the half of the housing 490 which is shown to complete the assembly.

Figure 36:
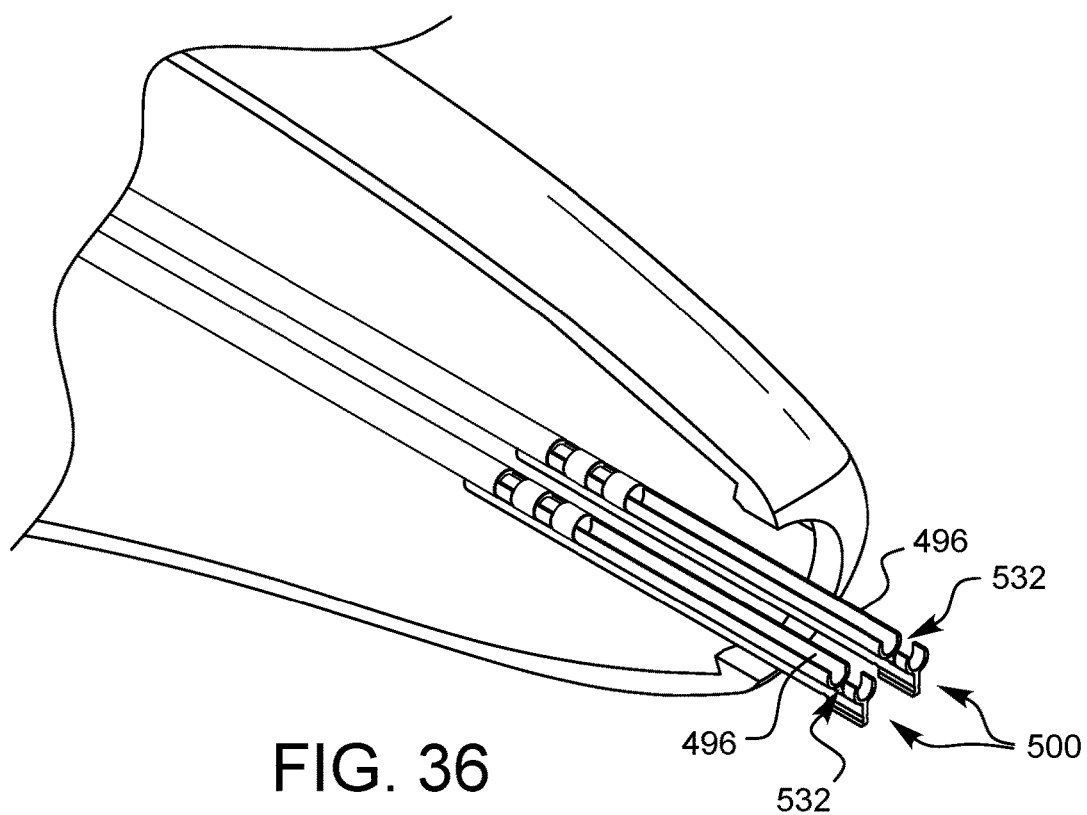
FIG. 36 is an enlarged view of the needle drivers in an exposed view of a portion of the surgical suturing device of FIG. 34A.
Figure 37:
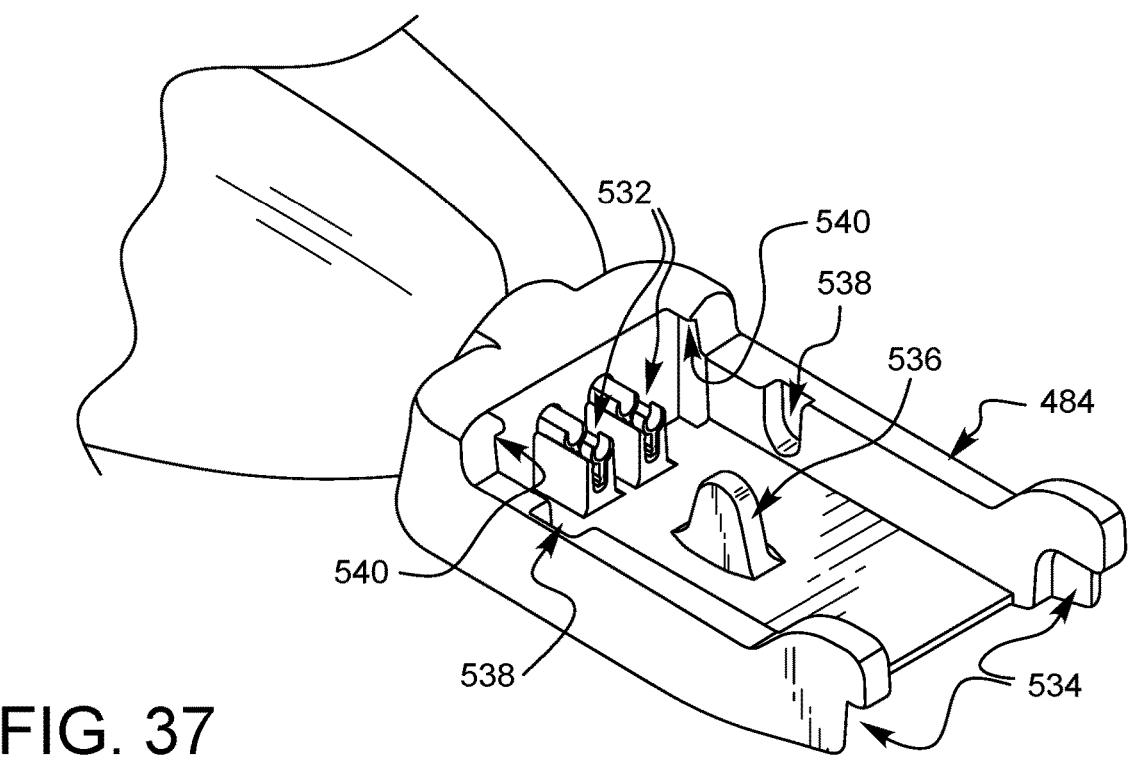
FIG. 37 is an enlarged view of the needle receivers and the cassette receiver of the surgical suturing device of FIG. 34A.

FIG. 36 is an enlarged, exposed view of the ends 500 of the needle drivers 496 in an exposed view of a portion of the surgical suturing device of FIG. 34A. The end 500 (distal) of each needle driver 496 has a needle receiver 532. FIG. 37 is an enlarged view of the needle receivers 532 and the cassette receiver 484 of the surgical suturing device of FIG. 34A. The cassette receiver 484 has pivot receivers 534, a needle release 536, multiple alignment slots 538, and multiple retention features 540 which will be discussed in more detail below.

Figure 38A:
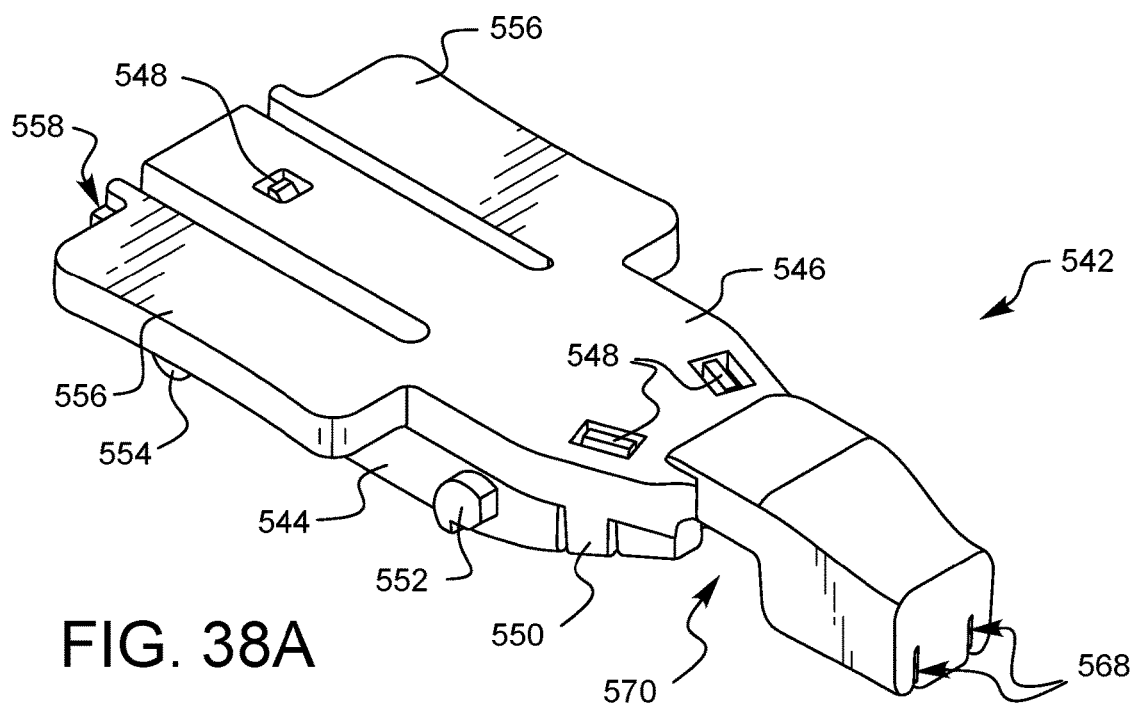
FIGS. 38A and 38B are different perspective views of a cassette embodiment for use with the surgical suturing device of FIG. 34A.
Figure 38B:
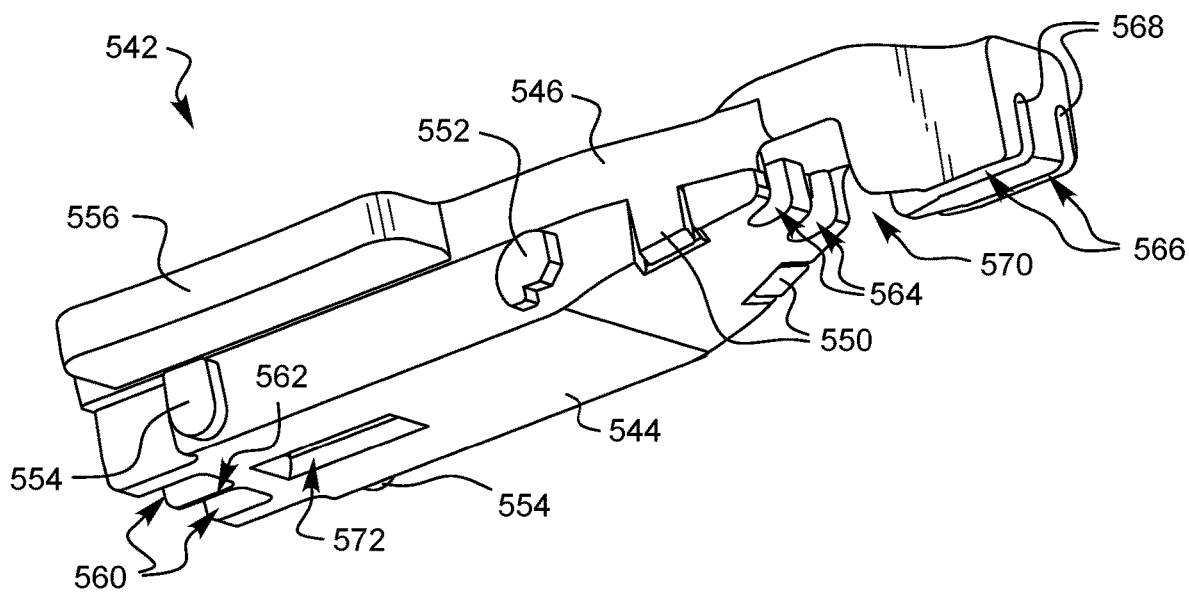

FIGS. 38A and 38B are different perspective views of a cassette 542 embodiment for use with the surgical suturing device of FIG. 34A. The cassette 542 houses two needles (not visible in this view) within a base 544 and a cover 546 which are coupled together. It is one advantage of this system that the needles are kept inside the cassette 542 because it reduces the opportunity for the surgical staff and surgeon to be cut during an operation by an exposed sharp needle. By necessity, patients are treated as though their blood carries harmful pathogens, so it is always disconcerting when someone on a surgical team is cut or poked by a needle. By keeping the needles within the cassette 542, away from skin, surgical procedures involving this cassette can be safer. There are a variety of ways the base 544 and cover 546 can be coupled together, including, but not limited to by latching, by gluing, and by welding. In this embodiment, the base 544 has multiple base latches 548 which engage slots in the cover 546, as well as multiple cover latches 550 which engage slots in the base 544. The cassette 542 has multiple pivots 552 (one of which is visible in FIGS. 38A, 38B, but the other is symmetrically located on the opposite side). The cassette 542 also has an alignment tab 554 on each side of the cassette 542. The cover 546 has two flexible arms 556 which may be pinched inwardly. Each of the flexible arms 556 has a retention latch 558 (one of which is visible in FIG. 38A, but the other is symmetrically located on the other flexible arm). The base 544 has two proximal openings 560 where the proximal ends of the needles (not shown) inside the cassette 542 are accessible. In other embodiments, the two proximal openings 560 may be combined into one shared proximal opening 560 by removing the dividing piece 562 between the two openings 560. The base 544 also has two distal openings 564 from which distal ends of the needles (not shown) may be extended. The cover 546 defines two ferrule holders 566 and two exit slots 568 for suture coupled to ferrules. Ferrules are not installed in the cassette of FIGS. 38A, 38B. The base 544 and cover 546 work together to define a cuff receiving area 570 between the distal openings 564 and the ferrule holders 566. The base 544 also defines a release slot 572 which is sized to allow the needle release from the cassette receiver (see FIG. 37) to pass.

Figure 39:
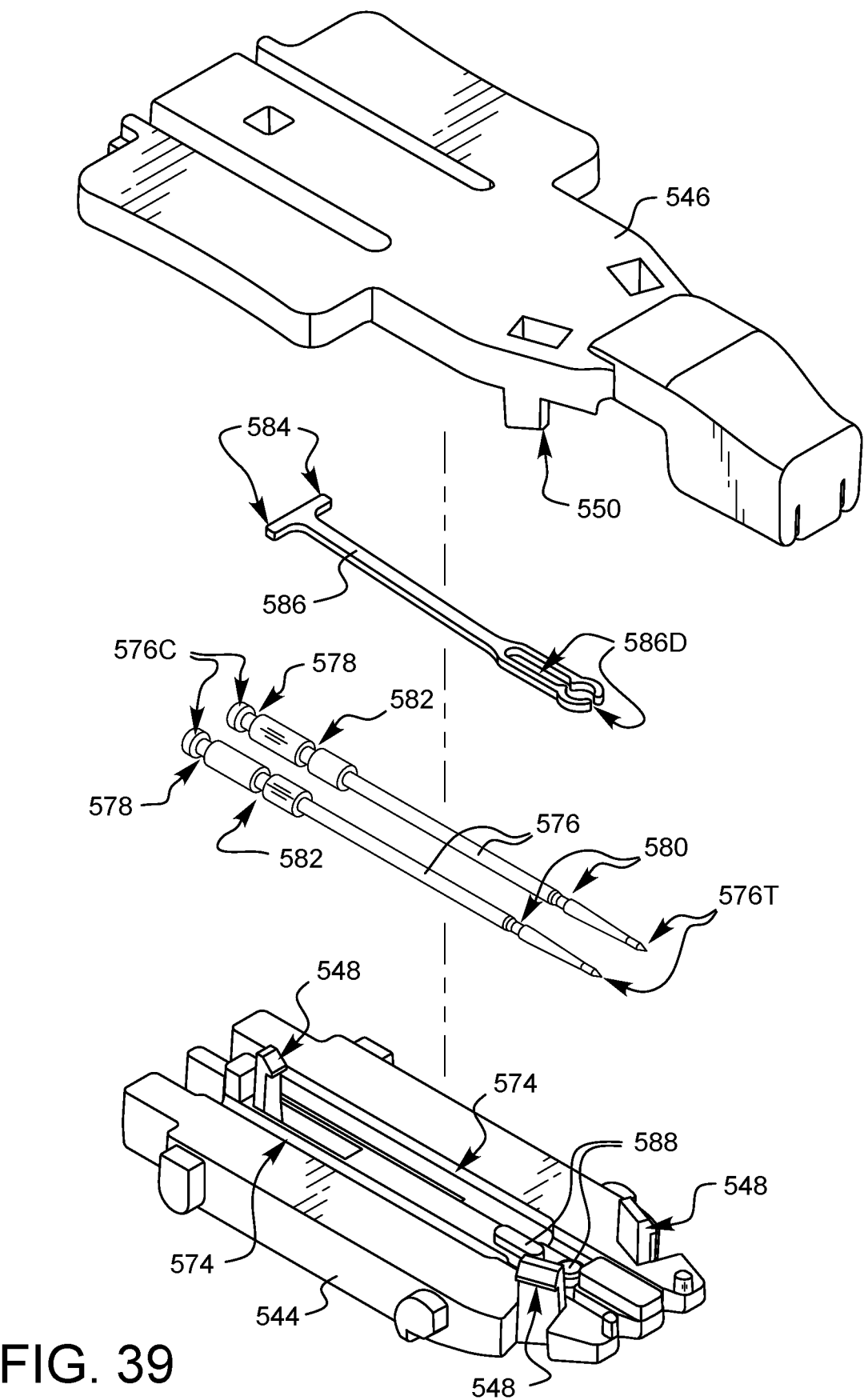
FIG. 39 is an exploded view of the cassette of FIG. 38A.

FIG. 39 is an exploded view of the cassette 542 of FIG. 38A which enables us to see the internal components of the cassette 542. The base 544 has needle guides 574 within which respective needles 576 are placed. The proximal end of each needle 576 is configured as a connector end 576C which has a slot 578 to mate with the needle receivers 532 of the suturing device when the cassette 542 is installed in the device. The distal end of the needles 576 are pointed into a tip 576T which will be able to penetrate a sewing cuff of a prosthetic replacement heart valve and engage a ferrule held in the ferrule holders of the cassette. Each needle 576 also has a needle cuff relief 580 which will be discussed later in more detail. Each needle 576 also has a latch feature 582 configured to be engaged by latch ends 584 of a flexible latch 586 inside the cassette 542. When the needles 576 are in the needle guides 574 of the base 544, the flexible latch 586 with two latch ends 584 is coupled at a distal end 586D of the flexible latch 586 to corresponding key features 588 in the base 544. The needles 576 are positioned so that the latch ends 584 fall into the latch features 582 on the needles 576, thereby restraining the needles 576 from moving out of the cassette 542. The cover 546 is attached to seal everything up and also to help constrain the needles 576 and the flexible latch 586. As mentioned, this design has the advantage of keeping the needles away from the operating staff and the patient to improve safety for all involved.

FIGS. 40A, 40B, 40C, 40D, 40E, and 40F are top, front, left, right, back, and bottom views of the cassette of FIG. 38A.

Figure 41A:
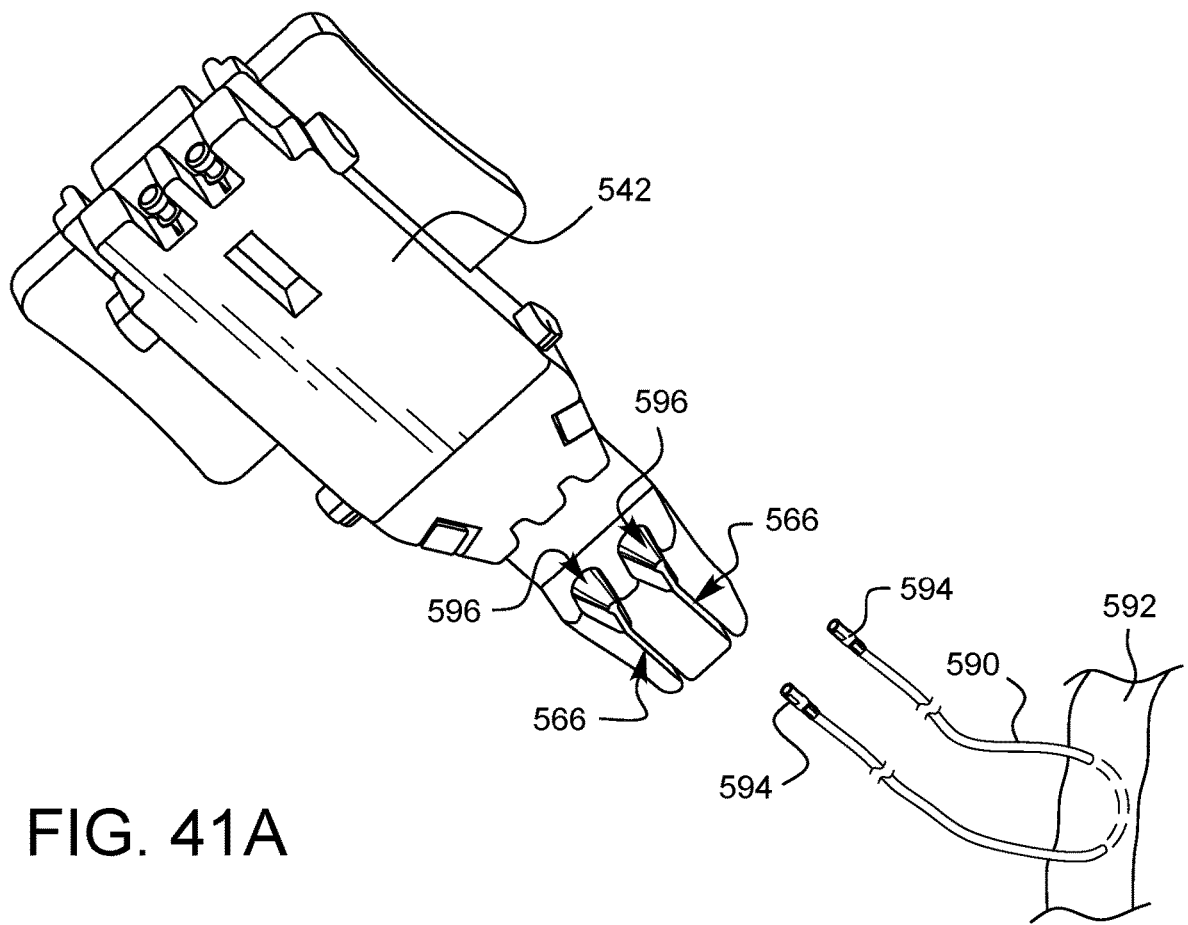
FIG. 41A is a perspective view of a surgical situation where a suture has been stitched into a tissue and ferrules on the ends of the suture are ready to be placed into the cassette of FIG. 38A.

FIG. 41A is a perspective view of a surgical situation where a suture 590 has been stitched into a tissue 592 and ferrules 594 on the ends of the suture 590 are ready to be placed into the cassette of FIG. 38A. As will be discussed later in this specification, the ferrules are configured to couple to needle tips. The ferrules may be coupled to the suture ends using a variety of techniques, including, but not limited to gluing, crimping, or a combination thereof. In particular, the cassette 542 has guide funnels 596 leading into the ferrule holders 566 to make it easier for operating staff to pull the ferrules 594 into the ferrule holders 566.

Figure 41B:
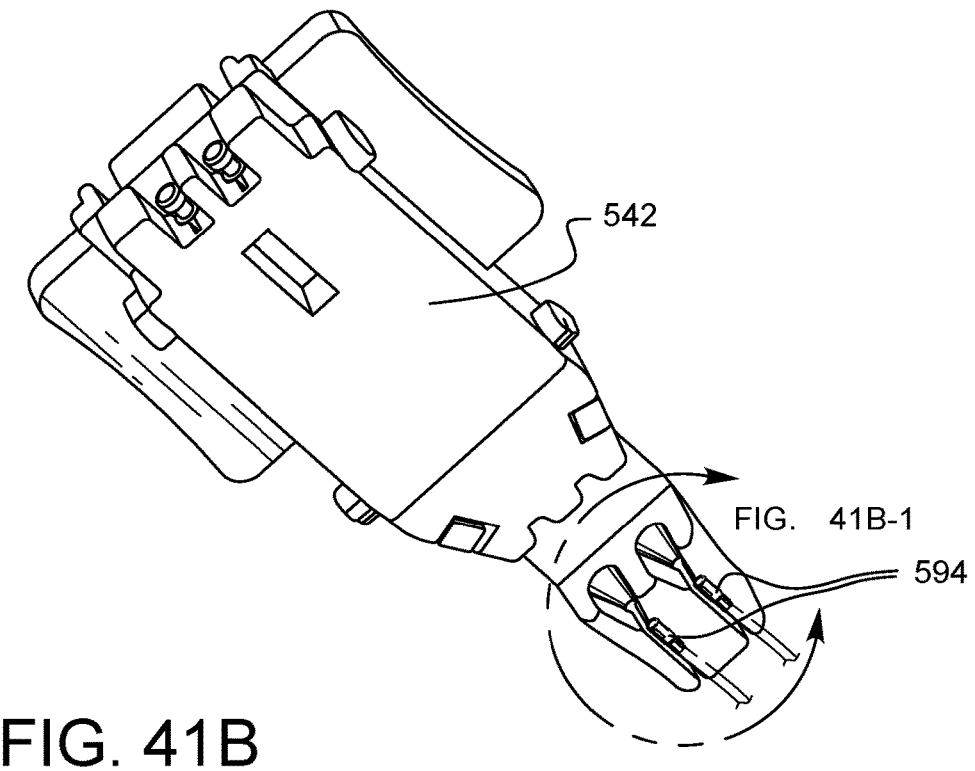
FIG. 41B illustrates the ferrules of FIG. 41A having been installed into the cassette of FIG. 38A.
Figures 1, 41B:
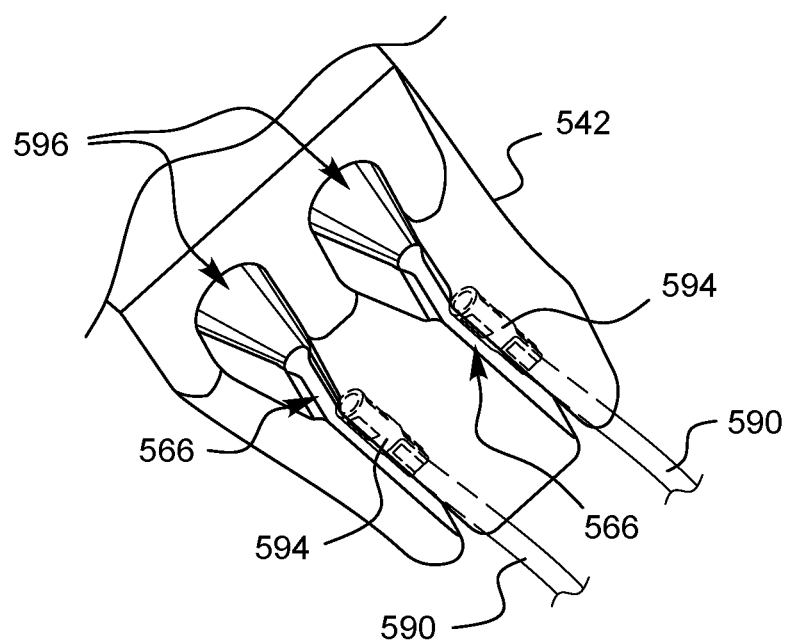
Figure 42:
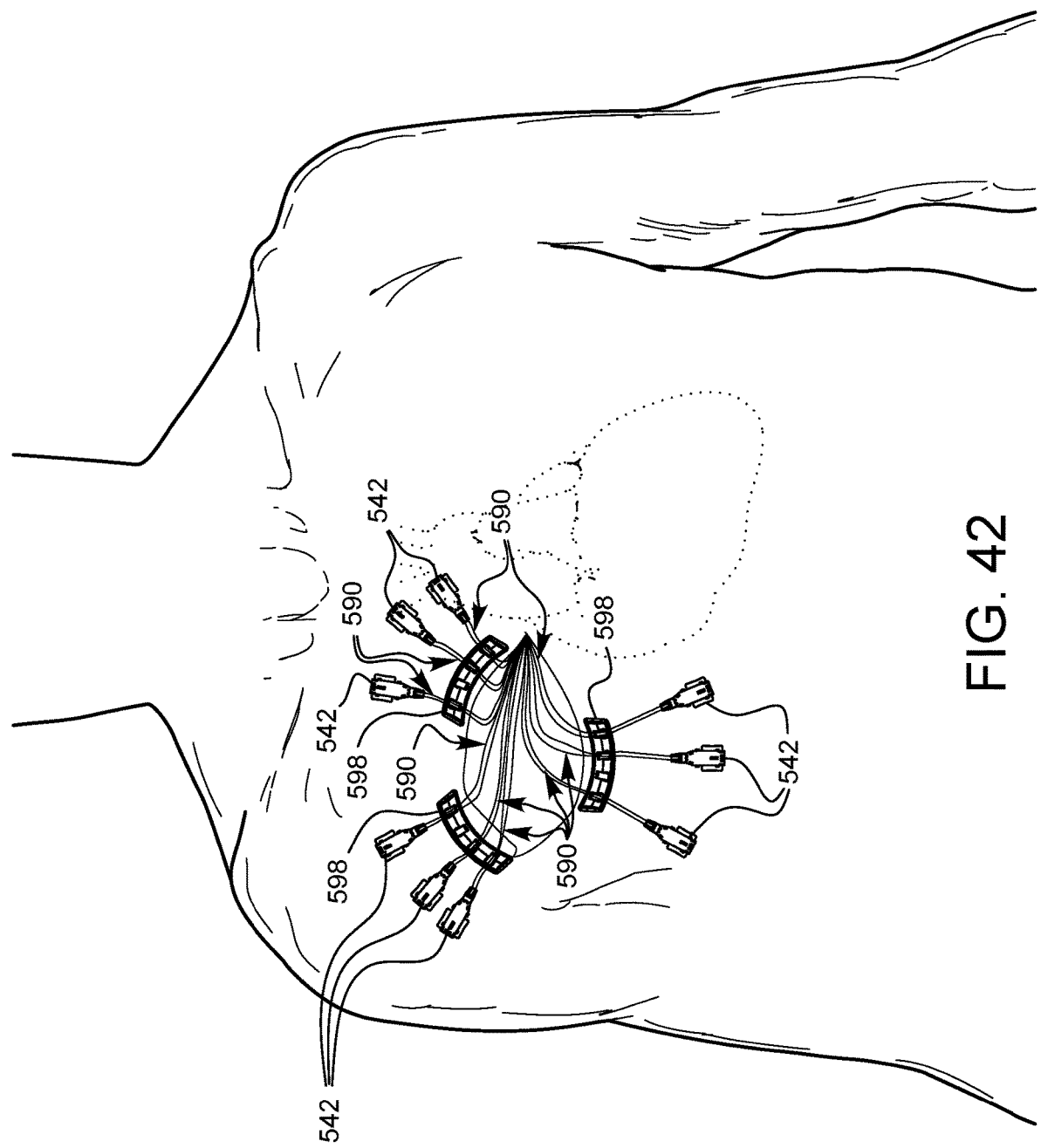
FIG. 42 illustrates multiple cassettes in a surgical situation where each cassette is coupled to ferrules on the ends of a different suture that has been stitched into a patient. The suture ends leading to each cassette are being held by a suture organizer.
Figure 43:
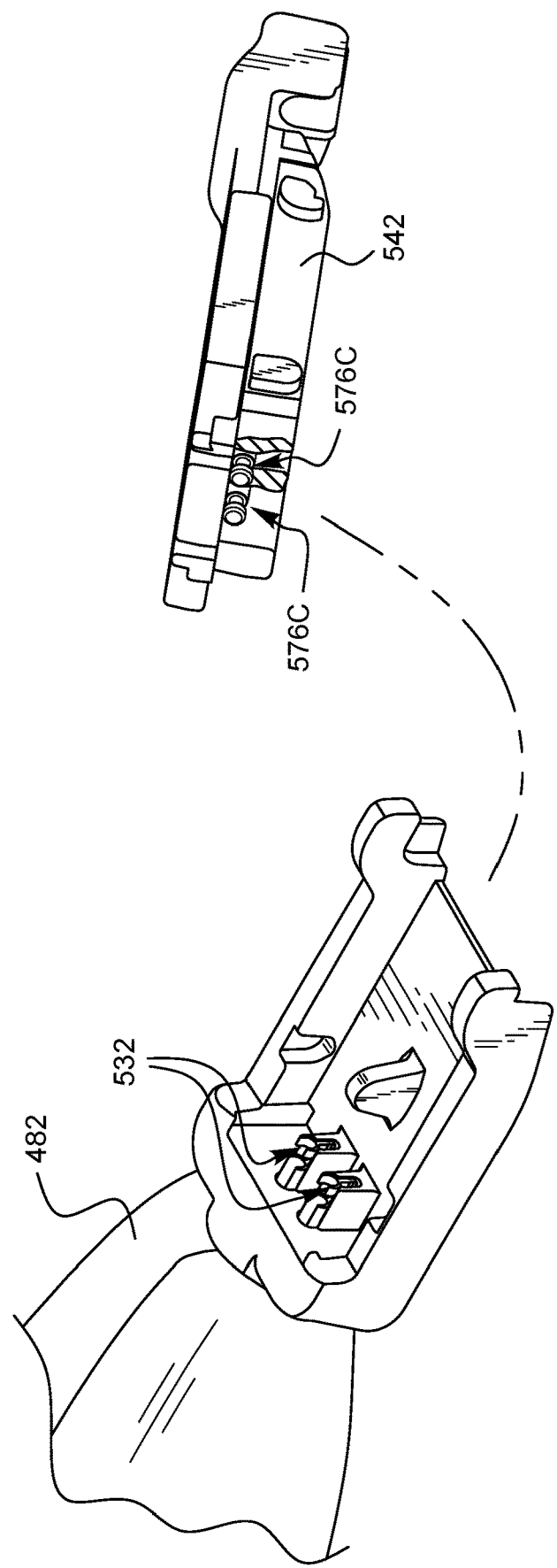
FIG. 43 shows a partially exposed view of the back side of the cassette of FIG. 38A to illustrate the connector ends of the needles in the cassette and how they are configured to mate with the needle drivers of the surgical suturing device.

FIG. 41B illustrates the ferrules 594 of FIG. 41A having been installed into the cassette 542 of FIG. 38A. FIG. 41B-1 is an enlarged view of the distal end of the cassette 542 from FIG. 41B showing the ferrules 594 installed in the ferrule holders 566 of the cassette 542. FIG. 42 illustrates multiple cassettes 542 in a surgical situation where each cassette 542 is coupled to ferrules (not visible in this view) on the ends of a different, respective sutures 590 that have been stitched into a patient. The suture ends leading to each cassette 542 are being held by one or more suture organizers 598. Once a desired number of sutures 590 have been placed into a patient, for example, for emplacement of a replacement heart valve, each cassette 542 can then be loaded into the surgical suturing device (such as the device of FIG. 34) in preparation for further stitching the suture 590 through a sewing cuff of the replacement heart valve. FIG. 43 shows a partially exposed view of the back side of the cassette 542 of FIG. 38A to illustrate the connector ends 576C of the needles in the cassette 574 and how they are configured to mate with the needle receivers 532 (on the distal end of the needle drivers) of the surgical suturing device 482.

Figure 44A:
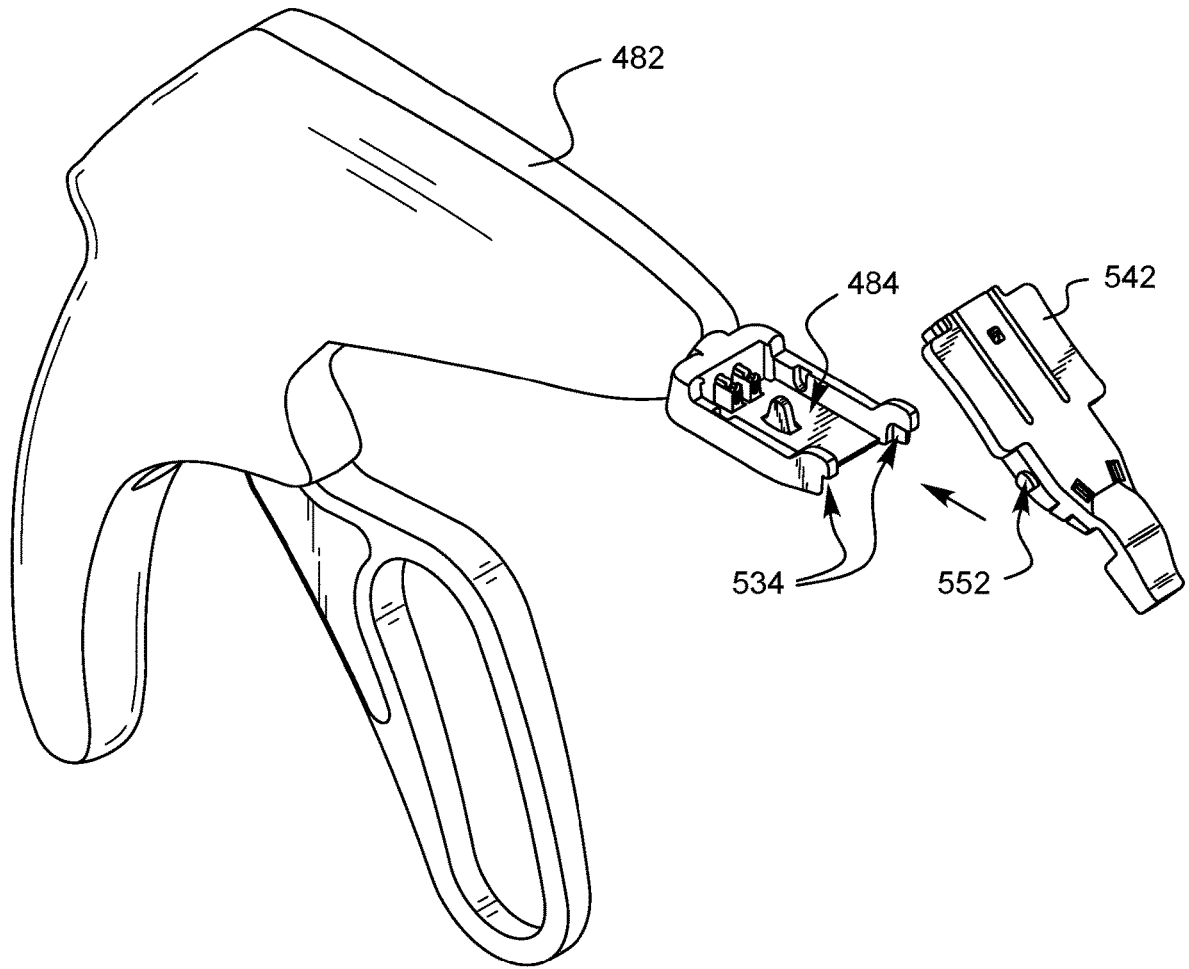
FIG. 44A illustrates the cassette of FIG. 38A ready to be loaded into the cassette receiver of the suturing device of FIG. 34.
Figure 44B:
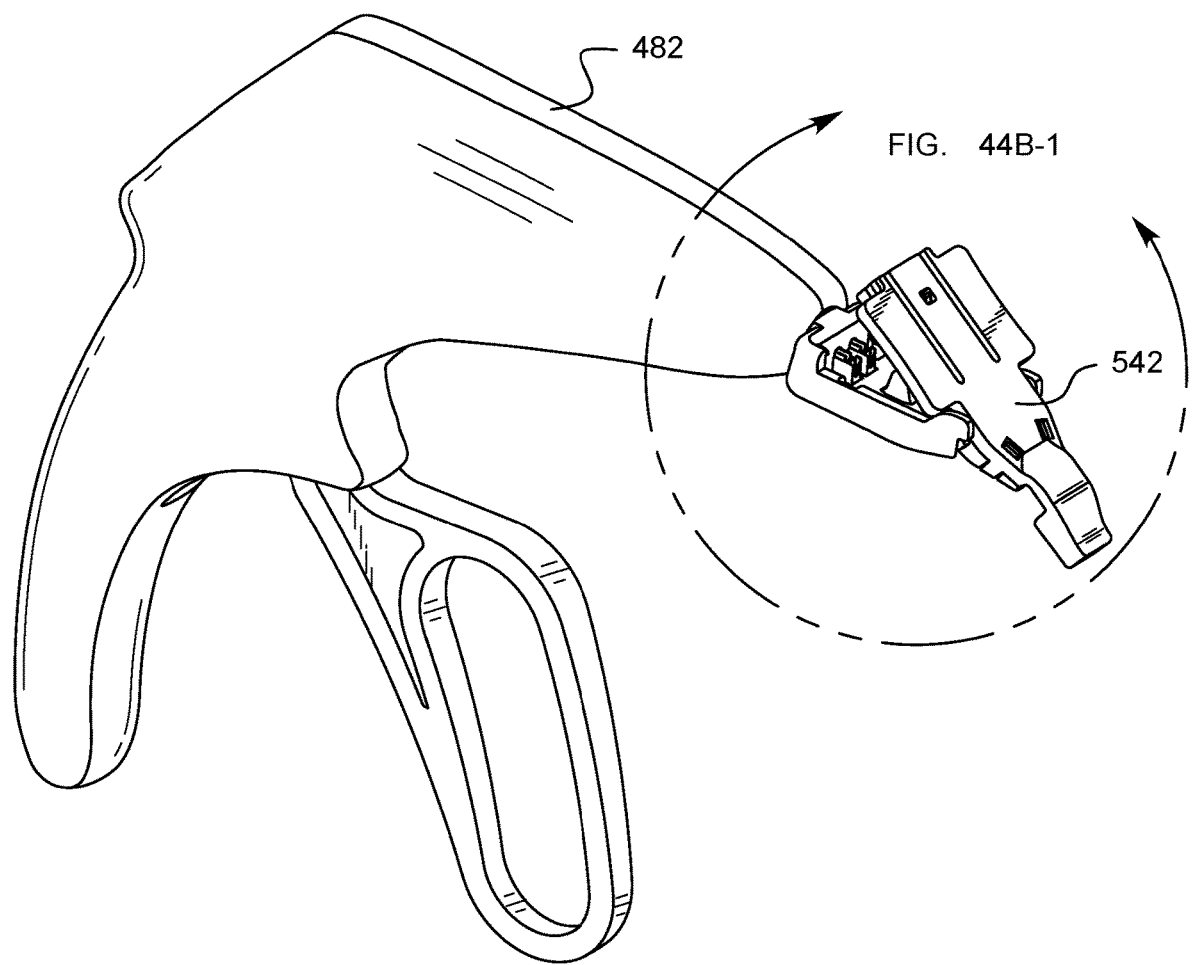
FIG. 44B shows pivots of the cassette of FIG. 38A placed into alignment with pivot receivers in the cassette receiver.
Figures 1, 44B:
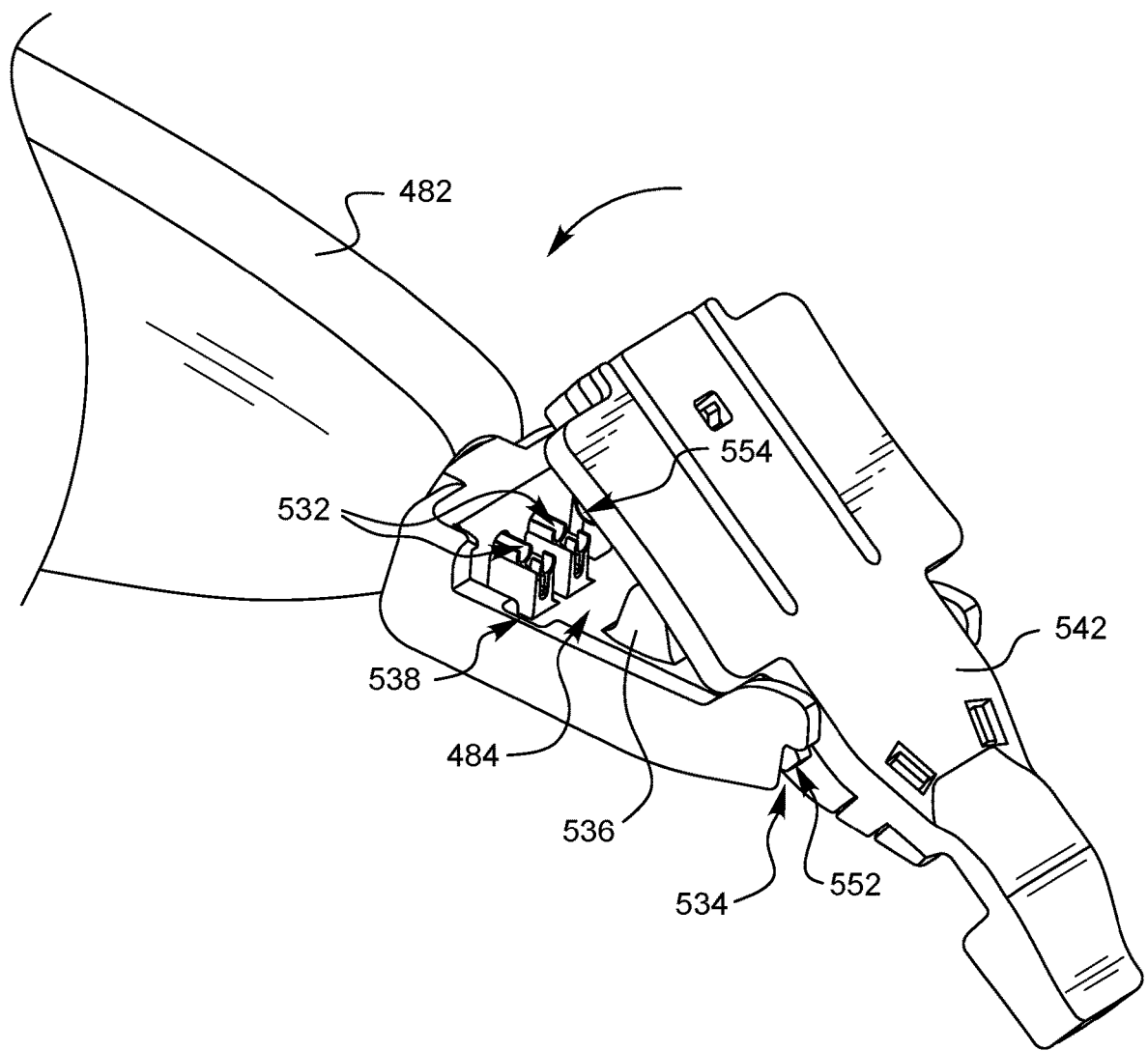
Figure 44C:
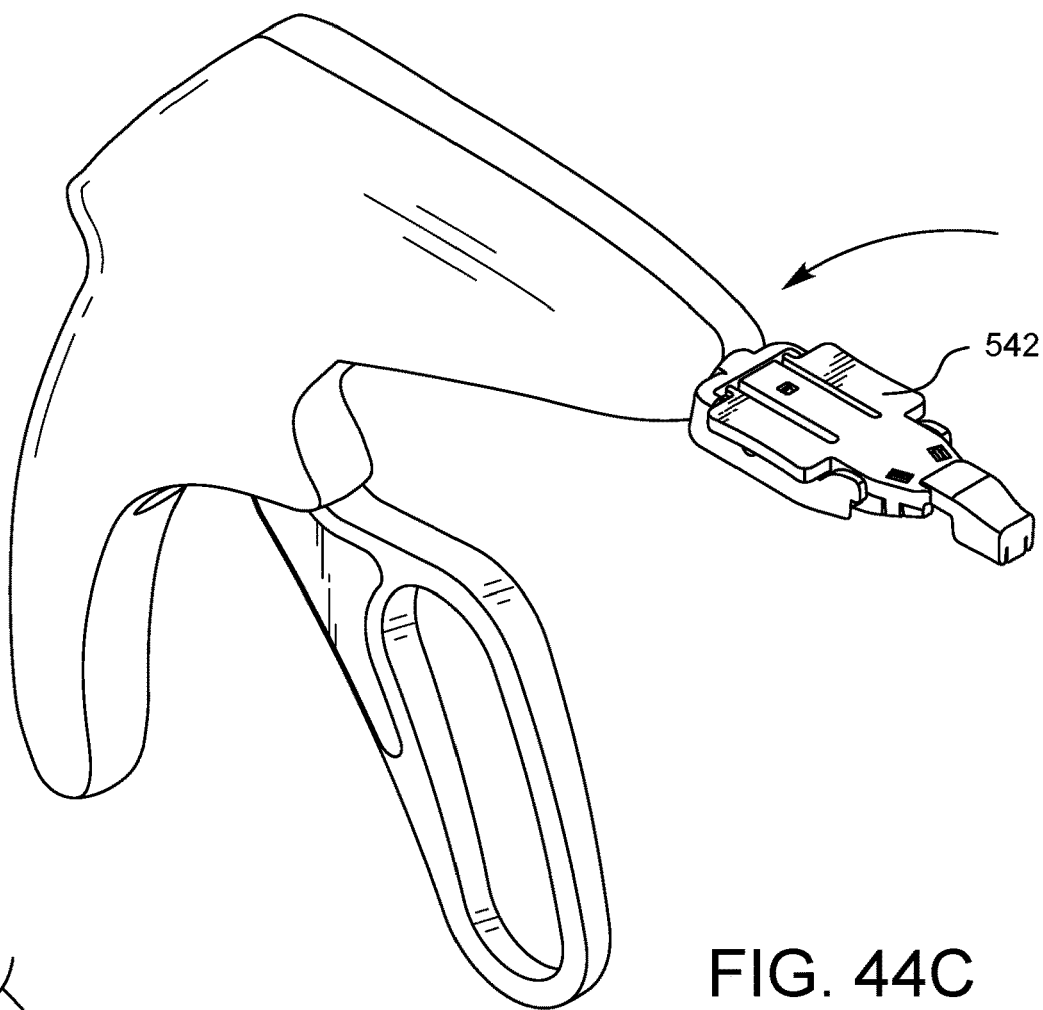
FIG. 44C shows the cassette having been rotated down around the cassette pivots so that the connector ends of the needles are coupled to the needle drivers of the suturing device.

FIG. 44A illustrates the cassette 542 of FIG. 38A ready to be loaded into the cassette receiver 484 of the suturing device 482 of FIG. 34. As shown in FIGS. 44A and 44B, the pivots 552 (only one of which is visible in this view) of the cassette 542 are placed into alignment with pivot receivers 534 in the cassette receiver 484. FIG. 44B-1 is an enlarged view of the cassette 542 and cassette receiver 484 of FIG. 44B. The alignment of the pivots 552 with the pivot receivers 534 can be clearly seen in this view. As shown in FIG. 44C in conjunction with FIG. 44B-1, the cassette 542 is then rotated down around the cassette pivots 552 so that the alignment tabs 554 on the cassette 542 move into the alignment slots 538 of the cassette receiver 484. As this occurs, the needle release 536 of the cassette receiver 484 pushes up into the release slot 572 of the cassette 542, the connector ends 576C of the needles 576 are coupled to the needle receivers 532 of the suturing device 482, and the retention latches 558 of the flexible arms 556 on the cassette 542 engage the retention features 540 of the cassette receiver 484 so that the cassette 542 is held firmly in place.

Figure 45:
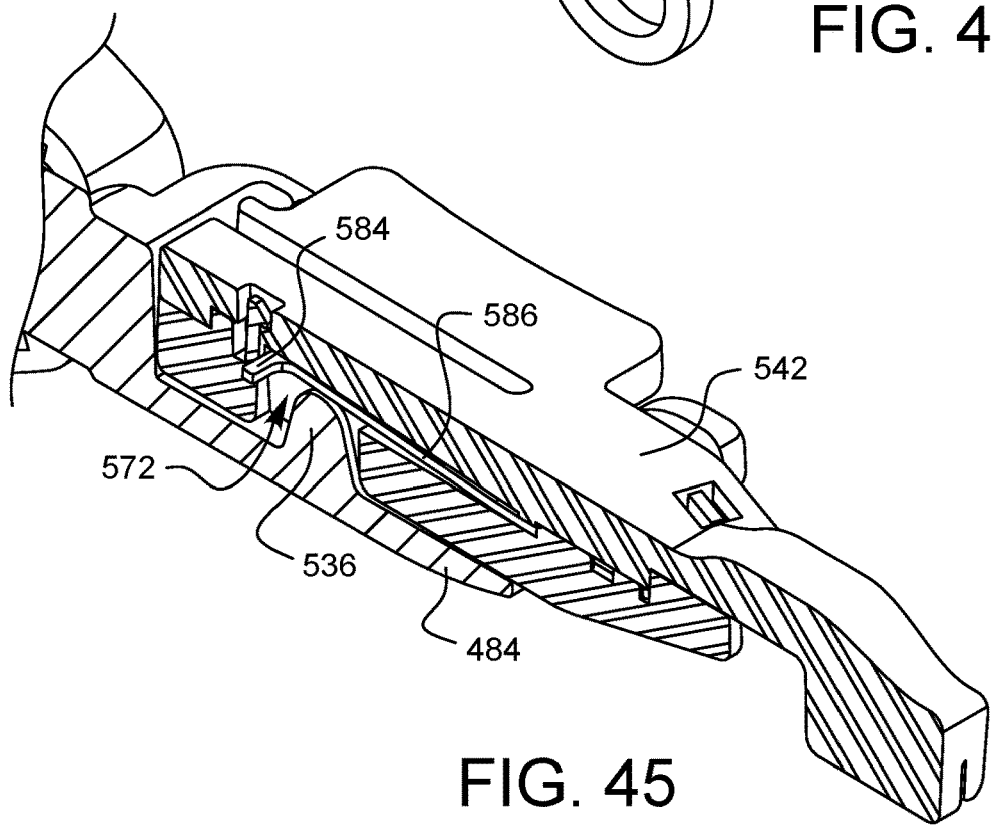
FIG. 45 is a cross-sectional view of the cassette installed in the cassette receiver of the suturing device.

FIG. 45 is a partial cross-sectional view of the cassette 542 installed in the cassette receiver 484 of the suturing device. When the needle release 536 passes up through the release slot 572, it deflects the flexible latch 586 upwards, causing the latch ends 584 to move out of the latch features in the needles (not shown in this view). The needles are held by the needle drivers, but they are now free to move if the needle drivers are moved.

Figure 46B:
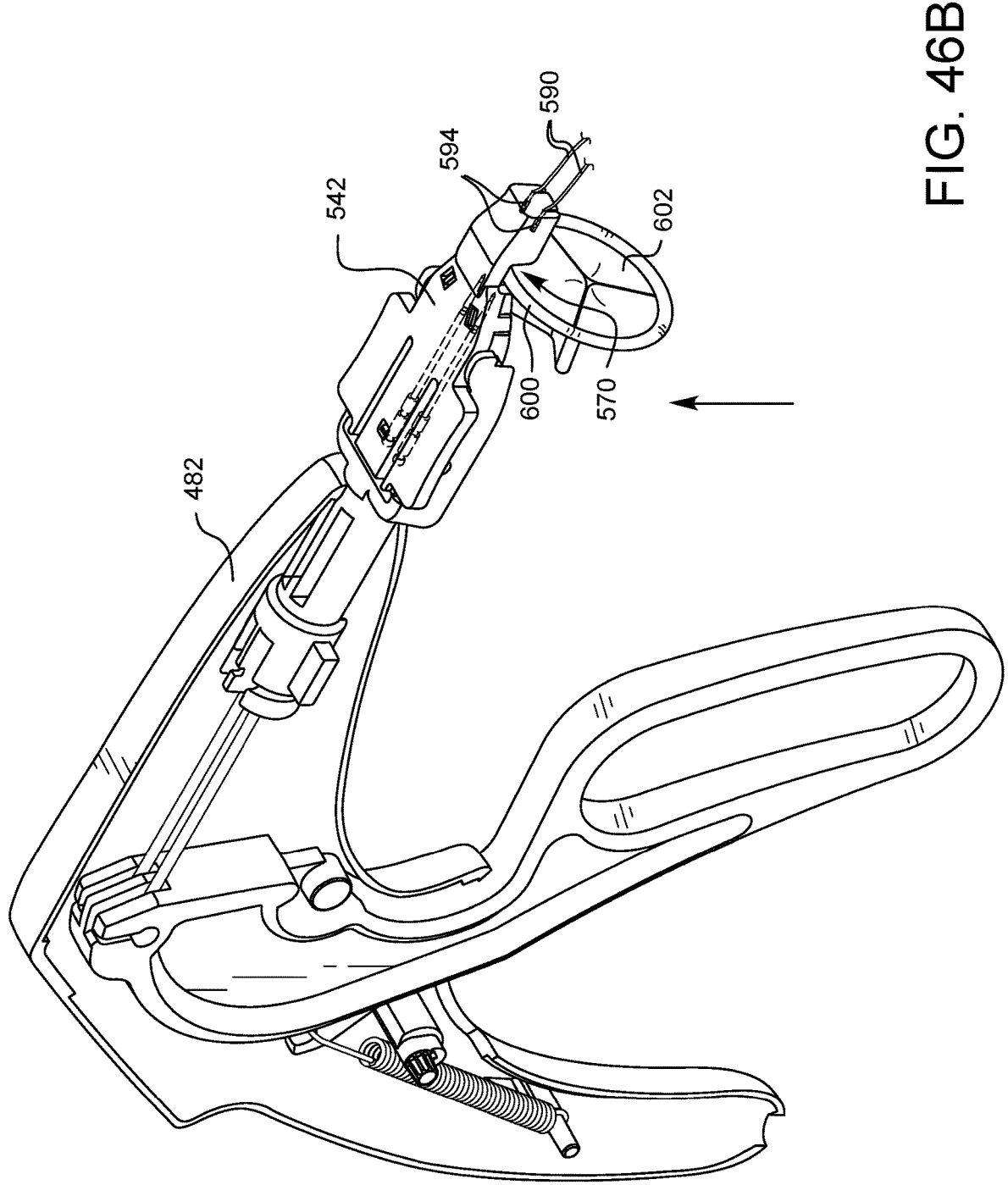
Figure 46C:
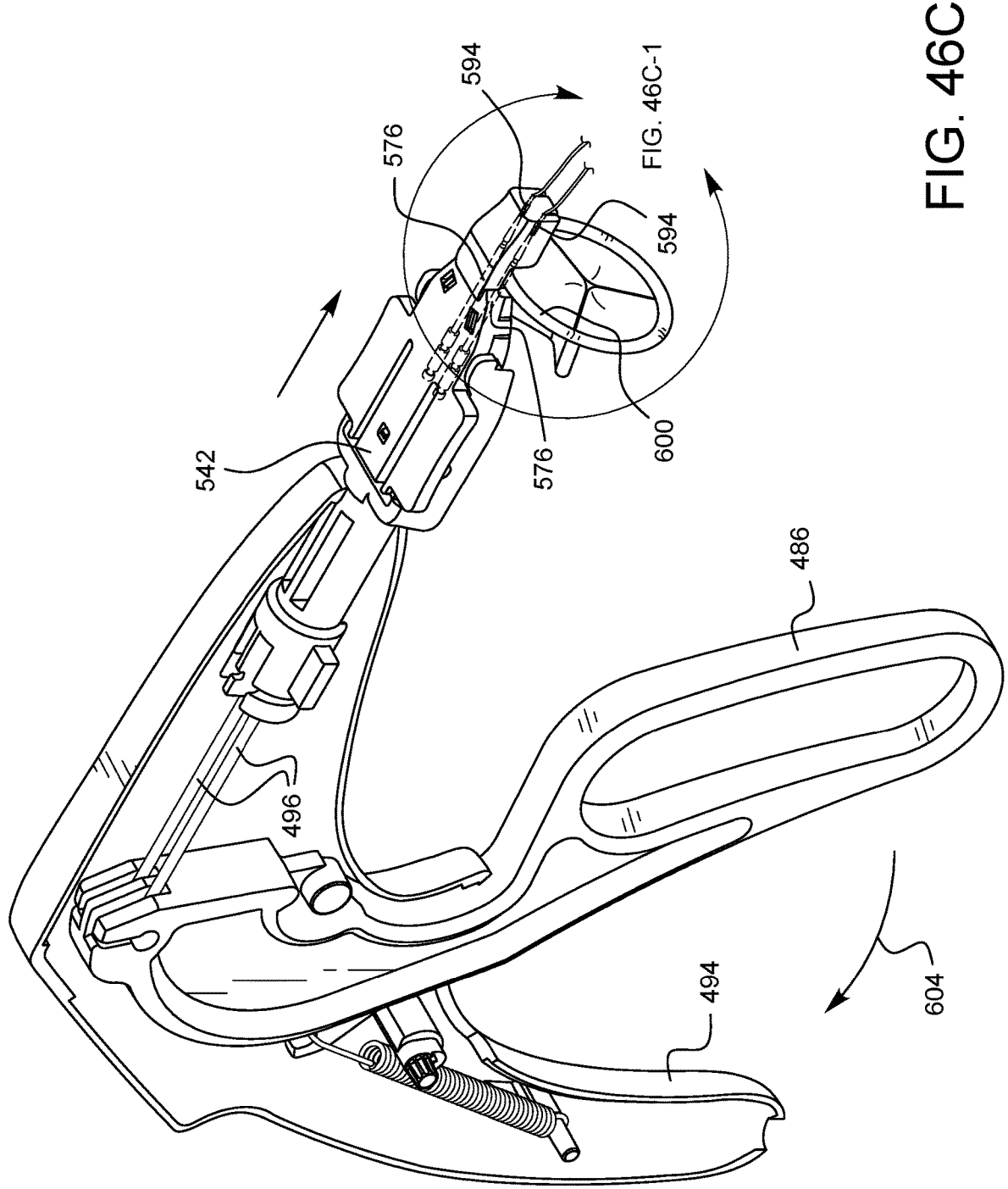
Figures 1, 46C:
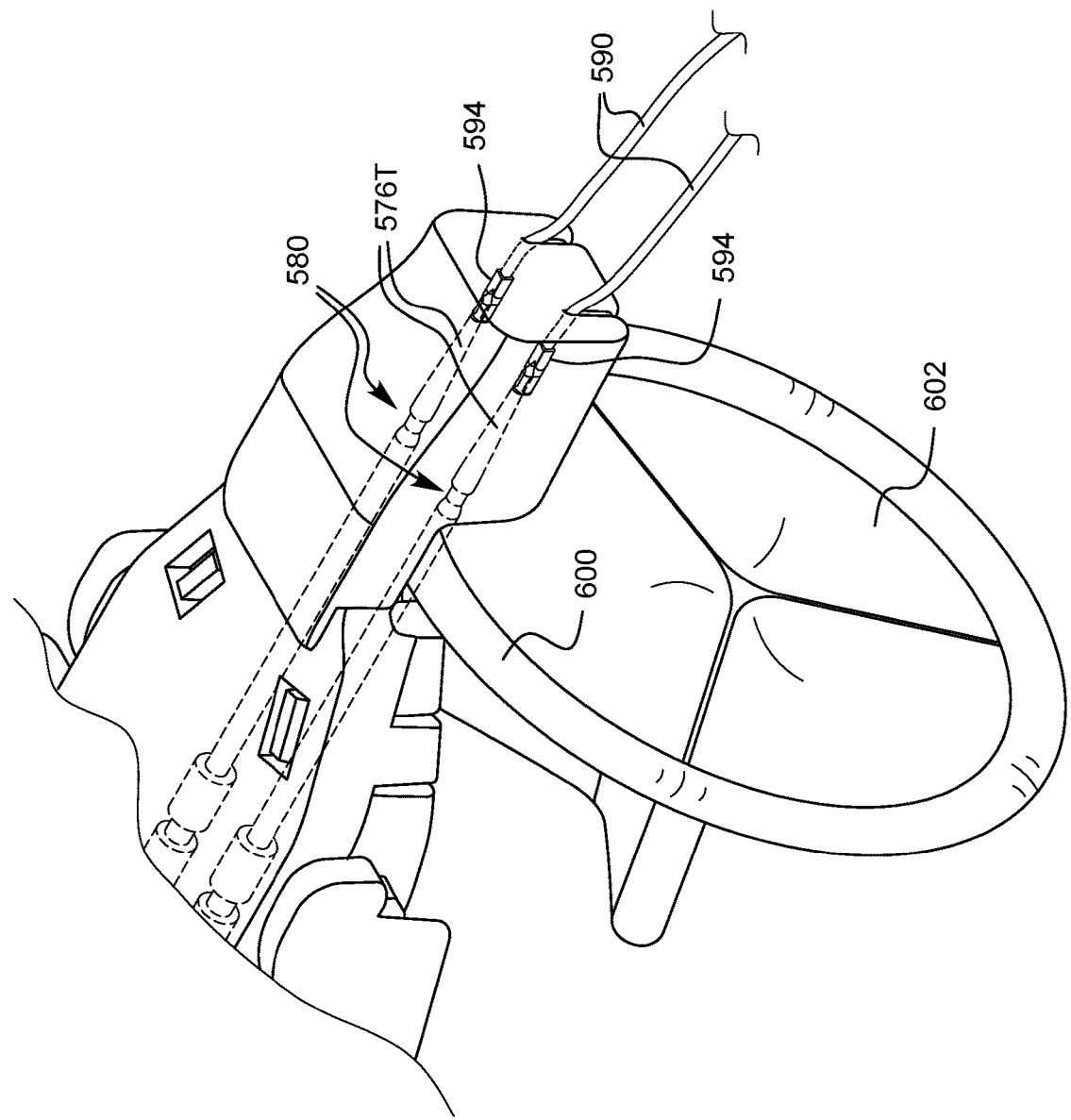
Figures 1, 46D:
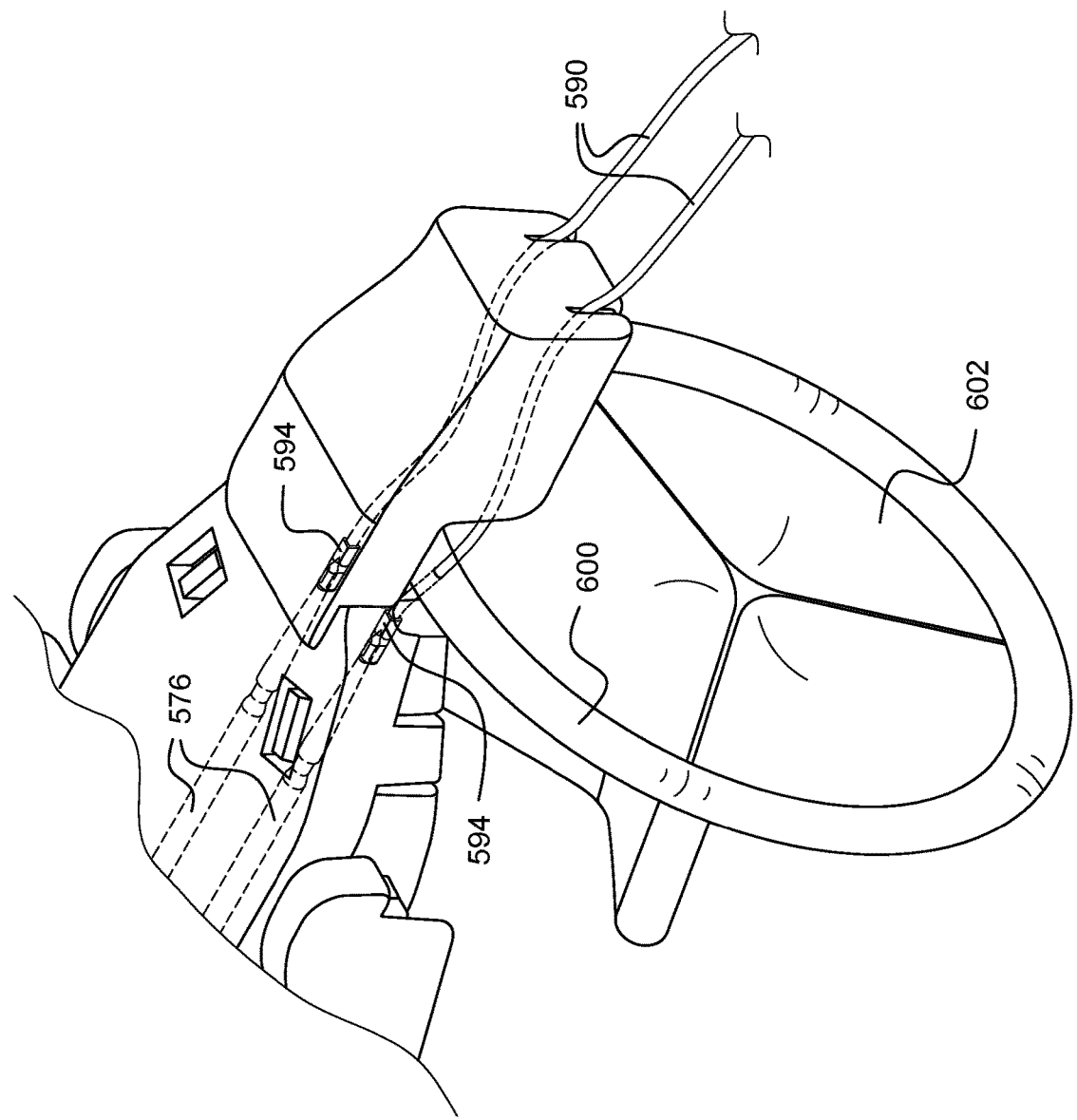
Figures 1, 46E:
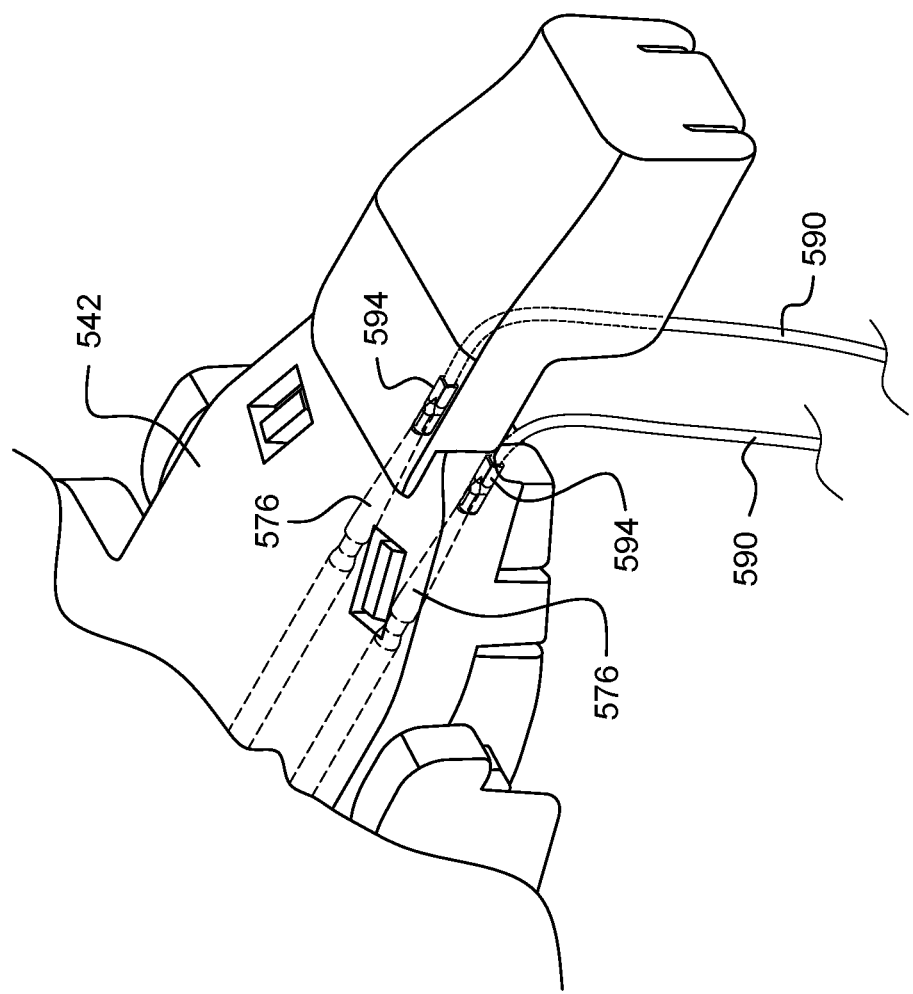
Figure 46F:
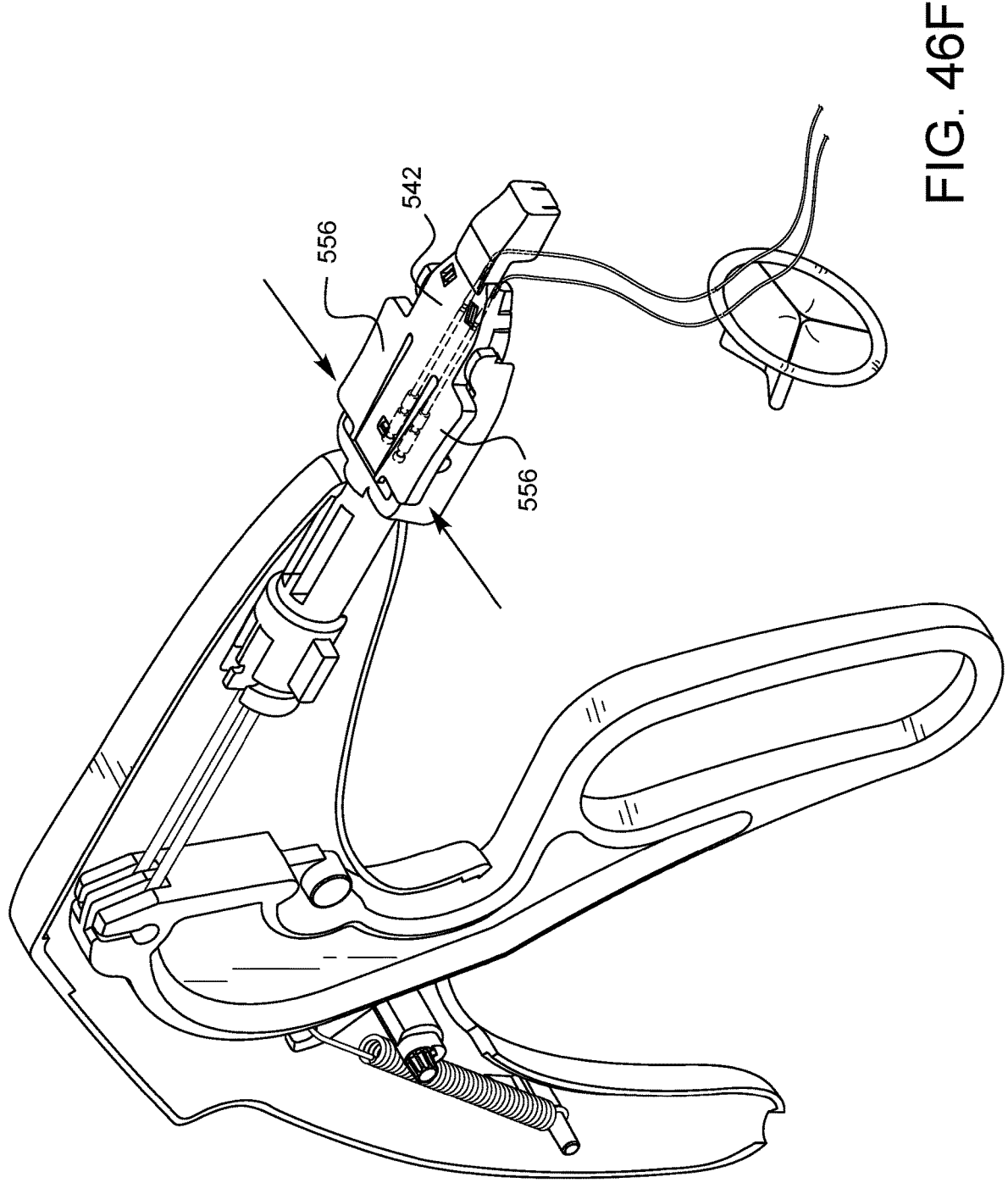
Figure 46G:
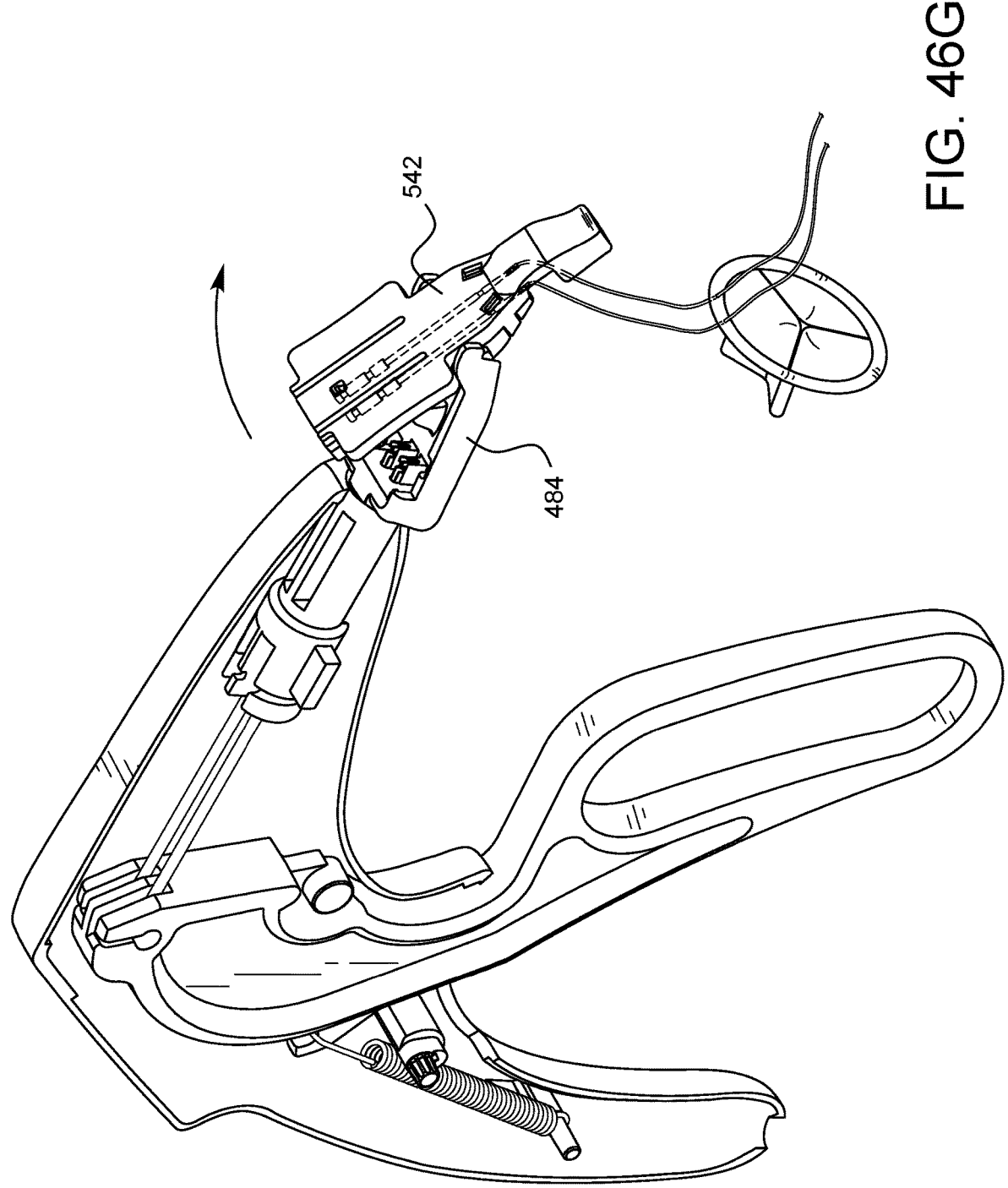
Figure 47:
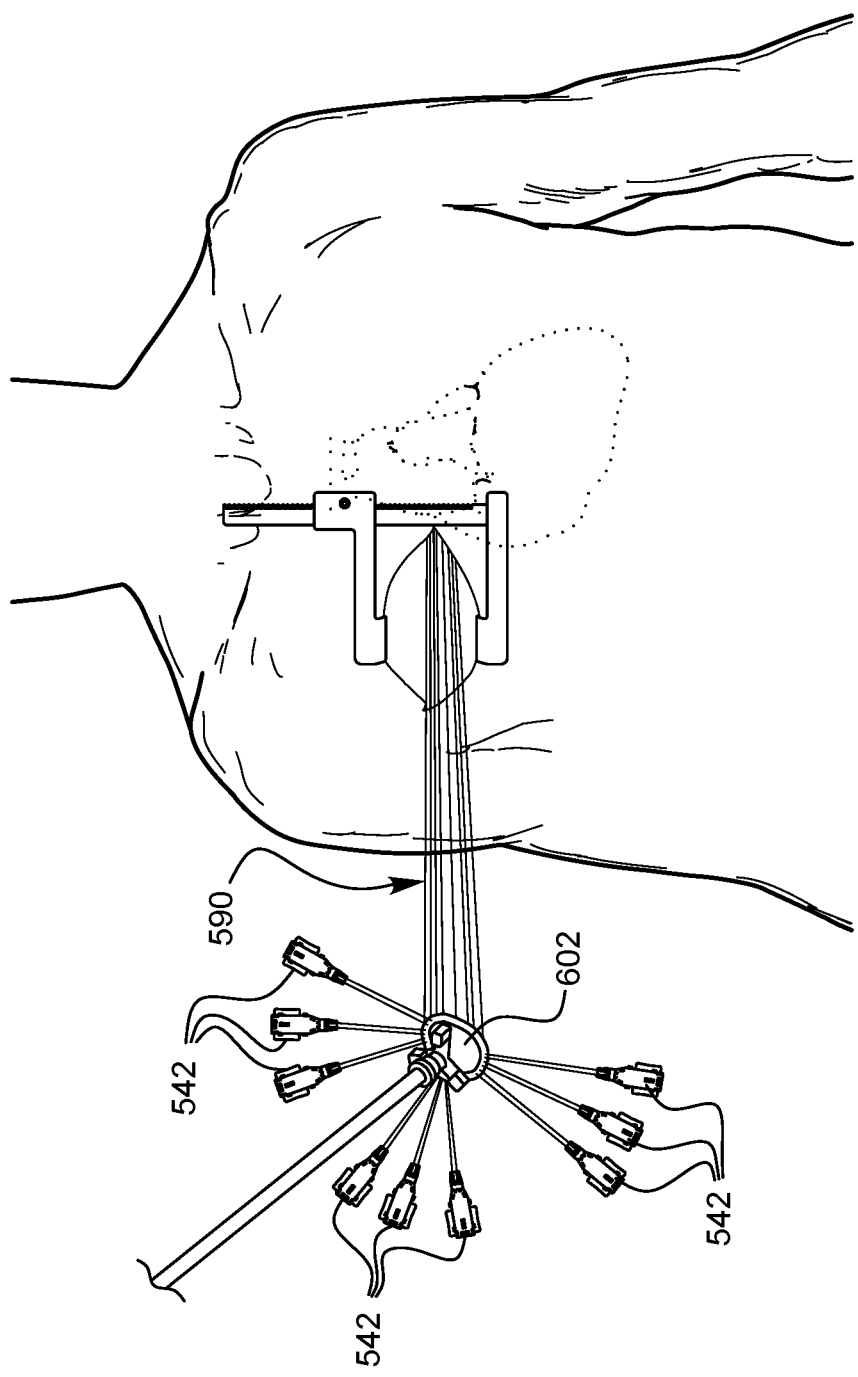
FIG. 47 illustrates a surgical situation where several pairs of suture ends have been stitched through a sewing cuff of a replacement heart valve. The cassettes still hold the ferrules on the suture ends, and the needles remain out of reach in each cassette.

FIGS. 46A-46G are partially exposed views illustrating how the surgical suturing device 482, with its installed cassette 542, may be used to place a suture stitch in a sewing cuff 600 of a replacement heart valve 602. In FIG. 46A, a replacement heart valve 602 having a sewing cuff 600 is shown. A cassette 542 is loaded into the suturing device 482. The cassette 542 has two ferrules 594 loaded into the cassette's ferrule holders, and the ferrules 594 are each attached to the ends of the same suture 590. The suture 590 has already been stitched through tissue, for example an aortic root adjacent to where the replacement heart valve will eventually be installed. The sewing cuff 600 is positioned below the cuff receiver 570, and then, as illustrated in FIG. 46B, the sewing cuff 600 is positioned within the cuff receiver 570. As shown in FIG. 46C, the handle 486 may be squeezed towards the grip 494, and this will cause the needle drivers 496 to move distally. In the view of FIG. 46C, the handle 486 has not been illustrated as pivoted so that the motion arrow 604 can indicate its path of travel. However, the needle drivers 496 are assumed to have moved the needles 576. This drives the needles 576 out of the cassette 542, through the sewing cuff 600, and into contact with the ferrules 594. This can better be seen in the enlarged view of FIG. 46C-1. The sewing cuff material 600 is stretched in a distal direction when the needles 576 pass through it. The needles 576 in this embodiment, however, have a needle cuff relief 580 which allows the sewing cuff 600 to straighten back out before the needles 576 are fully retracted, thereby decreasing the likelihood of the needles 576 jamming in the sewing cuff 600. Some embodiments may not have a needle cuff relief 580. As shown in FIG. 46D, the handle 486 can be released, causing the needle drivers 496 to retract the needles 576 back into the cassette 542. Since the needles 576 are now coupled to the ferrules 594, this pulls the ferrules 594 and suture 590 back through the sewing cuff 600. This can be seen more clearly in the enlarged view of FIG. 46D-1. As shown in FIG. 46E, the replacement valve 602 can be removed from the cuff receiver 570 with the suture 590 stitched through it. As shown in the enlarged view of FIG. 46E-1, the needles 576 and ferrules 594 are kept protected within the cassette 542. As shown in FIG. 46F, the flexible arms 556 of the cassette 542 may be pinched in to disengage the retention latches of the cassette from the retention features of the cassette receiver. This, then, allows the cassette 542 to be pivoted up on the pivots as shown in FIG. 46G and then removed from the cassette receiver 484. This can be repeated as needed with other cassettes 542 until all of the sutures have been placed through the sewing cuff 600 of the replacement valve 602 as illustrated in the surgical situation of FIG. 47. The cassettes 542 still hold the ferrules on the suture ends, and the needles remain out of reach in each cassette 542. The sutures 590 may be cut to sever the cassettes 542 from the suture ends as needed. The cassettes 542 can also assist with suture management by keeping the pairs of suture ends together and separate from other suture ends until needed.

Figure 48:
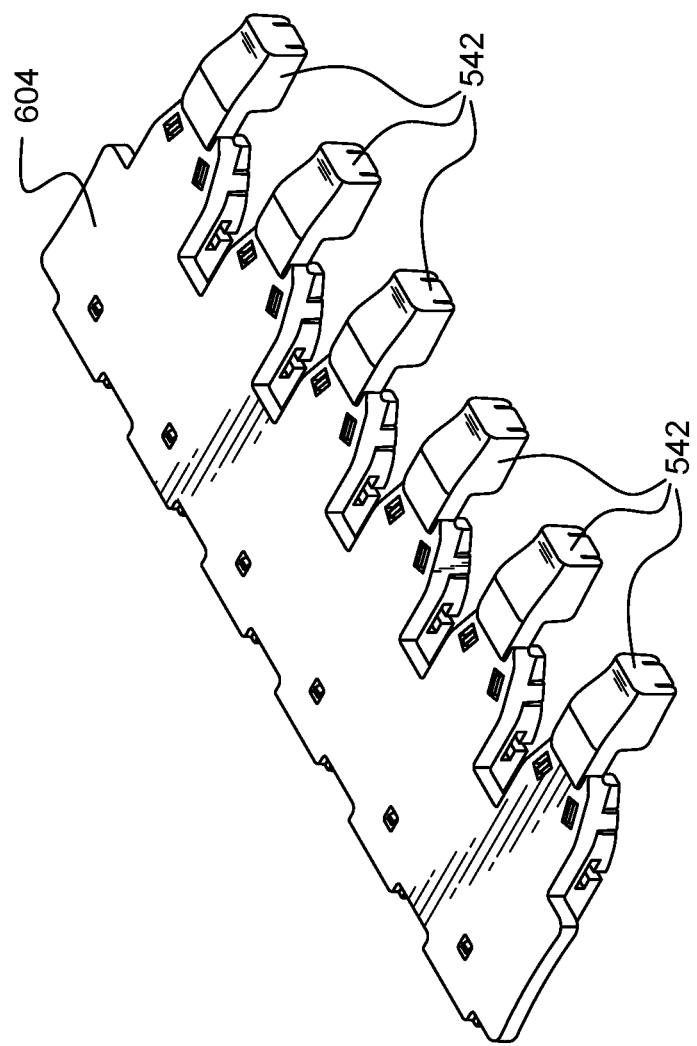
FIG. 48 illustrates one embodiment of a magazine having multiple cassettes.

FIG. 48 illustrates one embodiment of a magazine 604 having multiple cassettes 542. This embodiment combines the concepts of the magazine used earlier with the concept of the cassette more recently discussed.

Figure 49A:
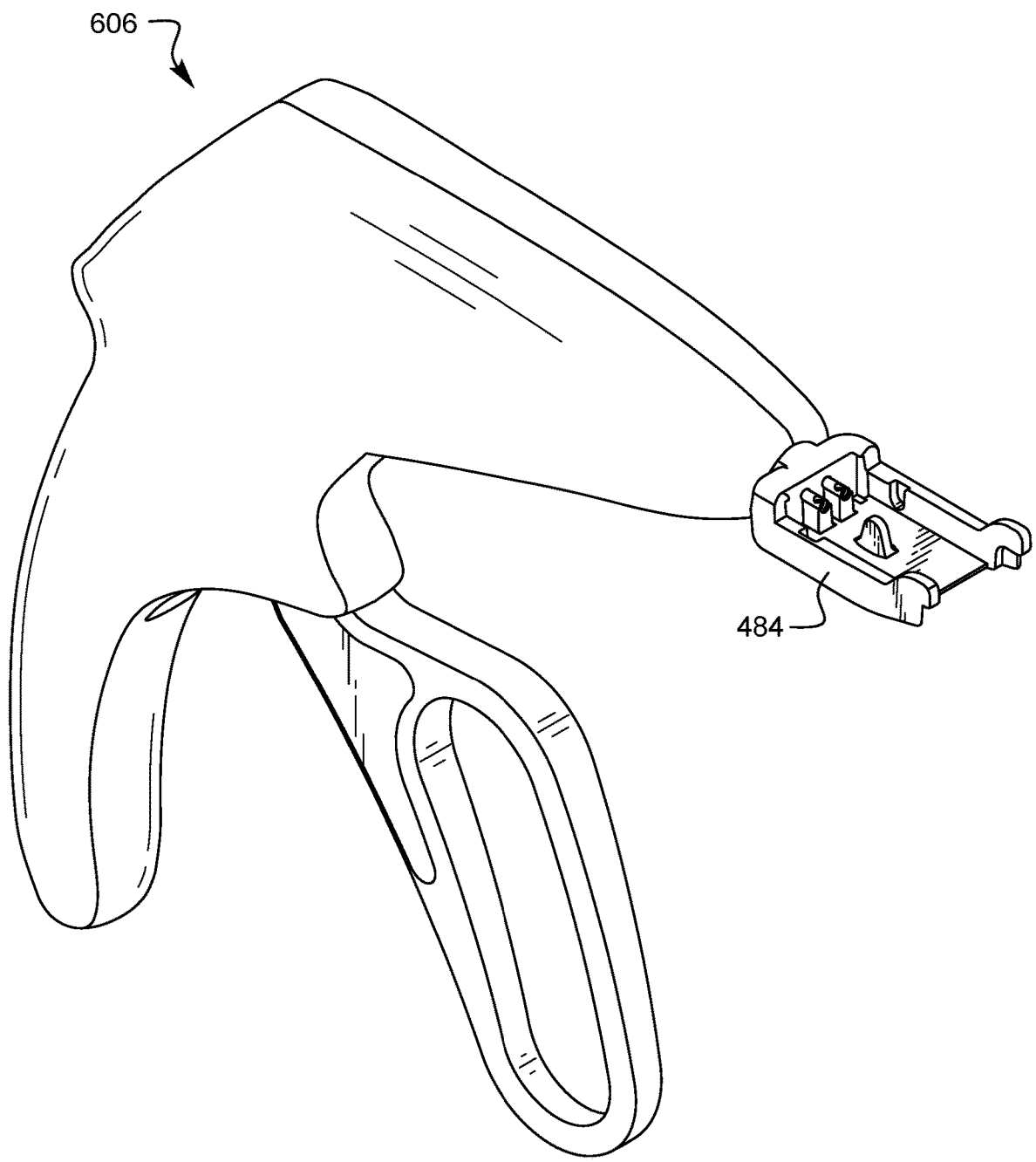
FIG. 49A illustrates another embodiment of a surgical suturing device having a cassette receiver.
Figure 49B:
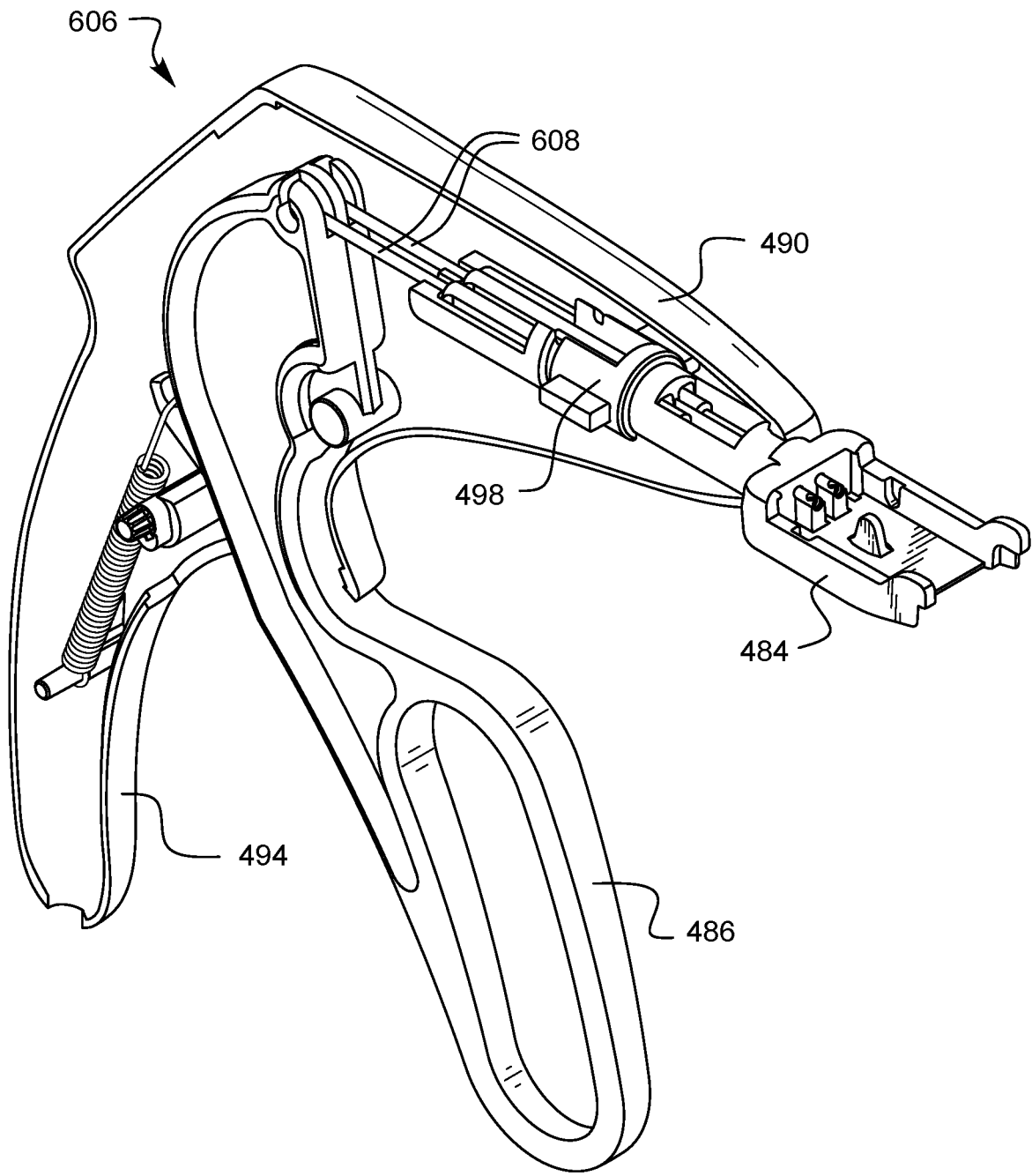
FIG. 49B is the surgical suturing device of FIG. 49A in a partially exposed view.
Figure 50:
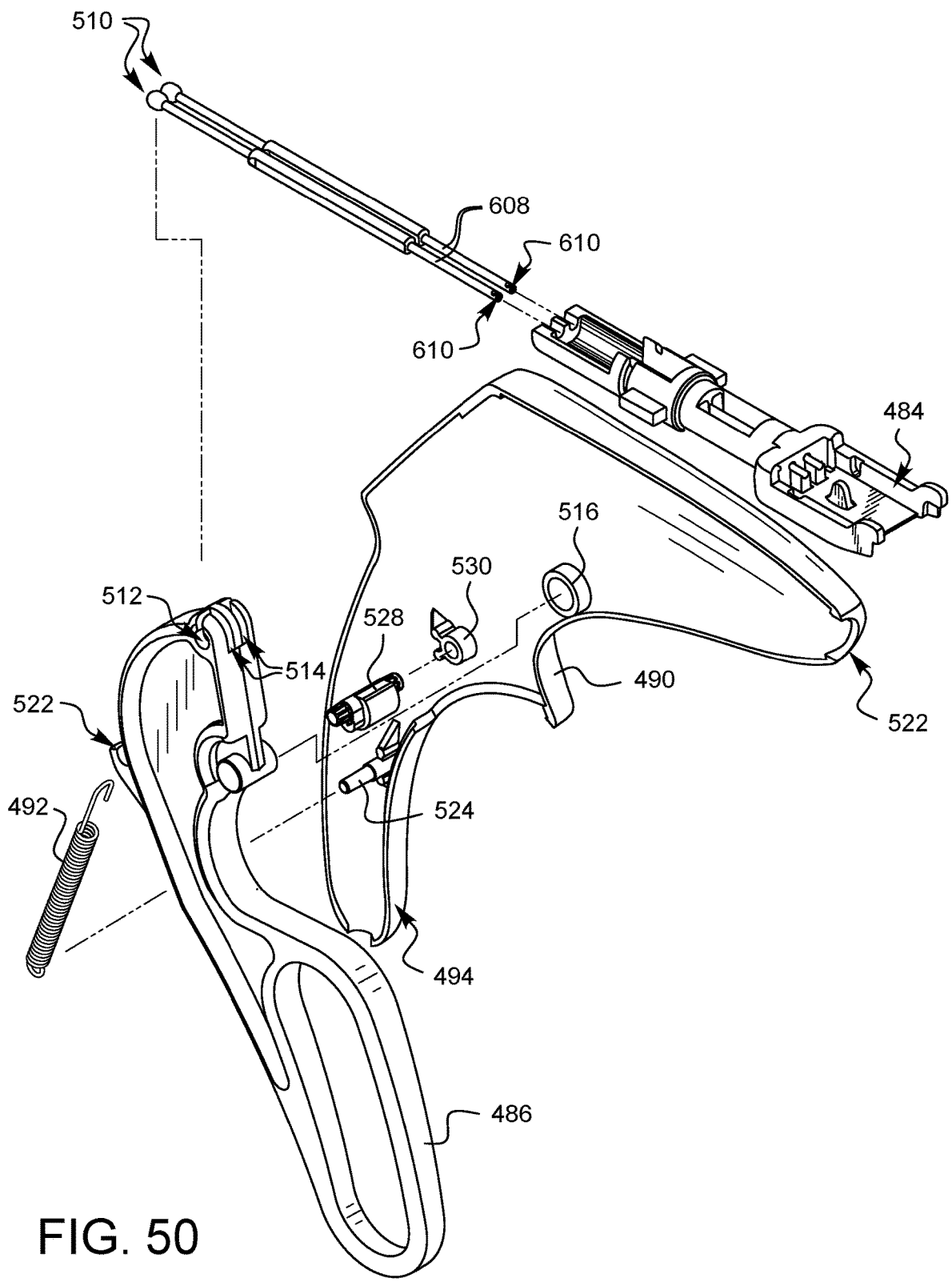
FIG. 50 is an exploded view of the surgical suturing device of FIG. 49A.
Figure 51:
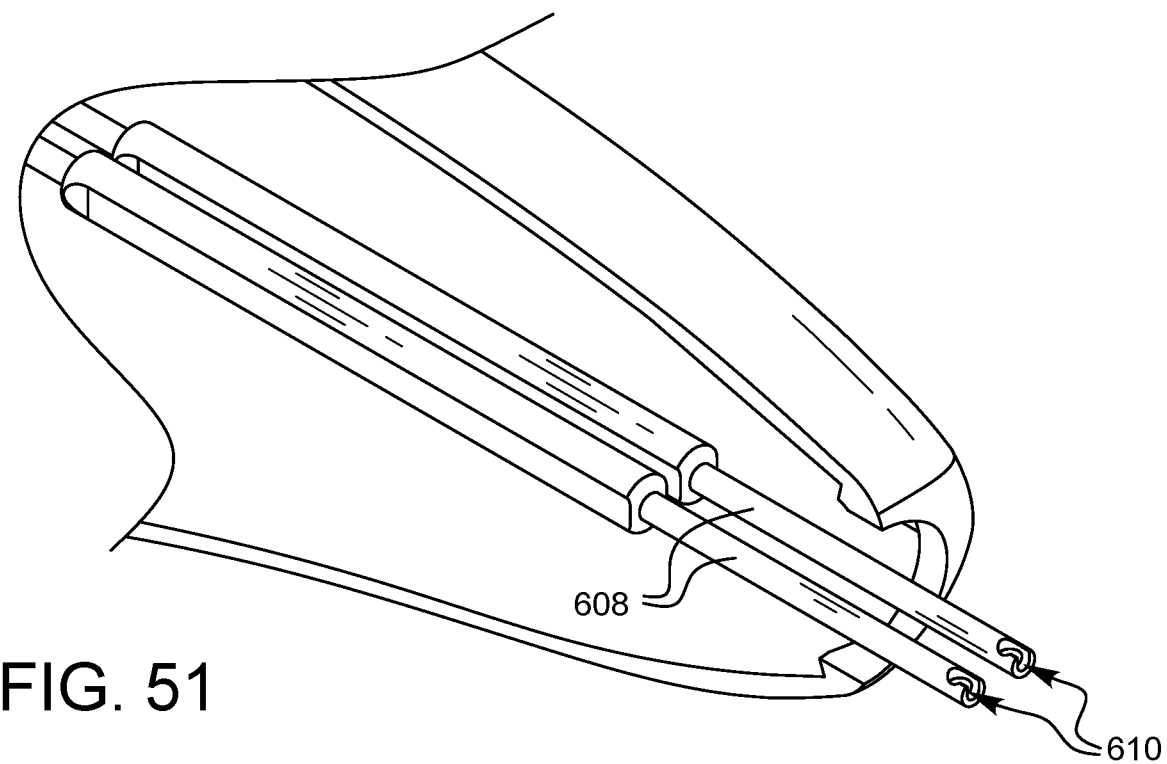
FIG. 51 is an enlarged view of the needle drivers in an exposed view of a portion of the surgical suturing device of FIG. 49A.
Figure 52:
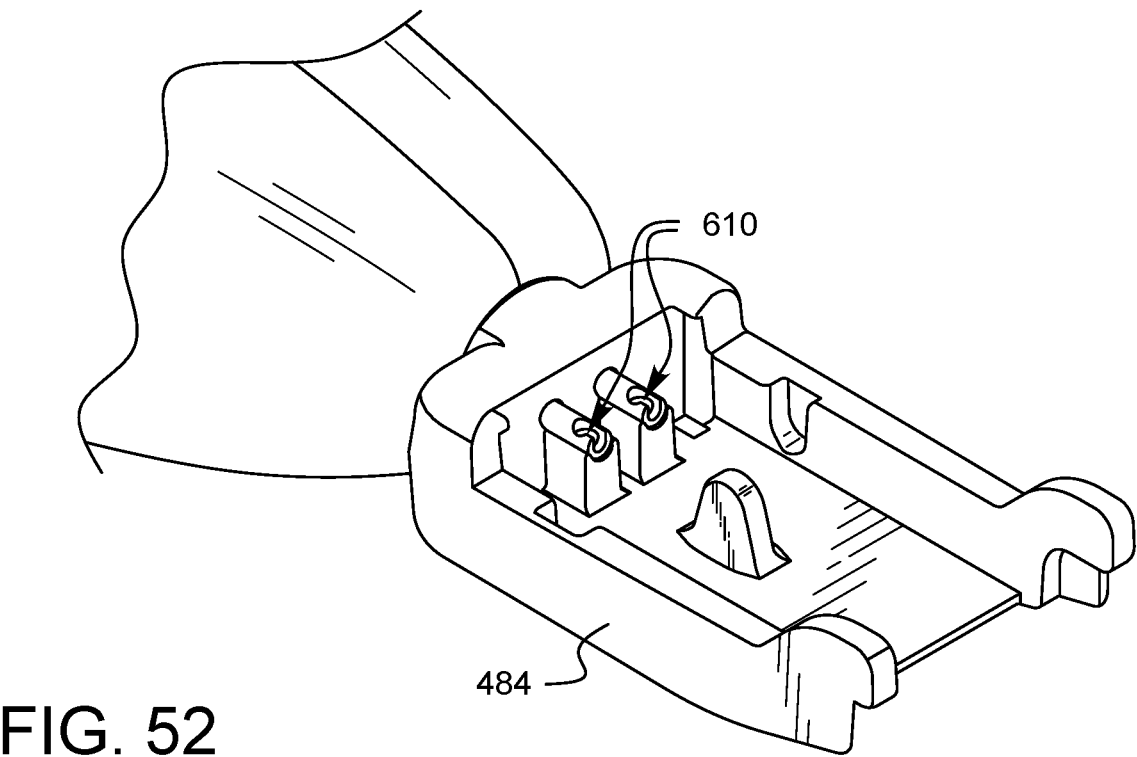
FIG. 52 is an enlarged view of the needle receivers and the cassette receiver of the surgical suturing device of FIG. 49A.

FIG. 49A illustrates another embodiment of a surgical suturing device 606 having a cassette receiver 484. This embodiment is similar to the embodiment of FIG. 34A, except that the needle drivers 608 (more visible in the exposed view of FIG. 49B and the exploded view of FIG. 50) are all one piece and the needle receivers 610 on the needle drivers 608 have a different shape. FIG. 51 is an enlarged view of a portion of the needle drivers 608 in an exposed view of a portion of the surgical suturing device of FIG. 49A. FIG. 52 is an enlarged view of the needle receivers 610 and the cassette receiver 484 of the surgical suturing device 606 of FIG. 49A. In this embodiment, the needle receivers 610 are shaped to receive a ball connector from a needle in a cassette.

Figure 53A:
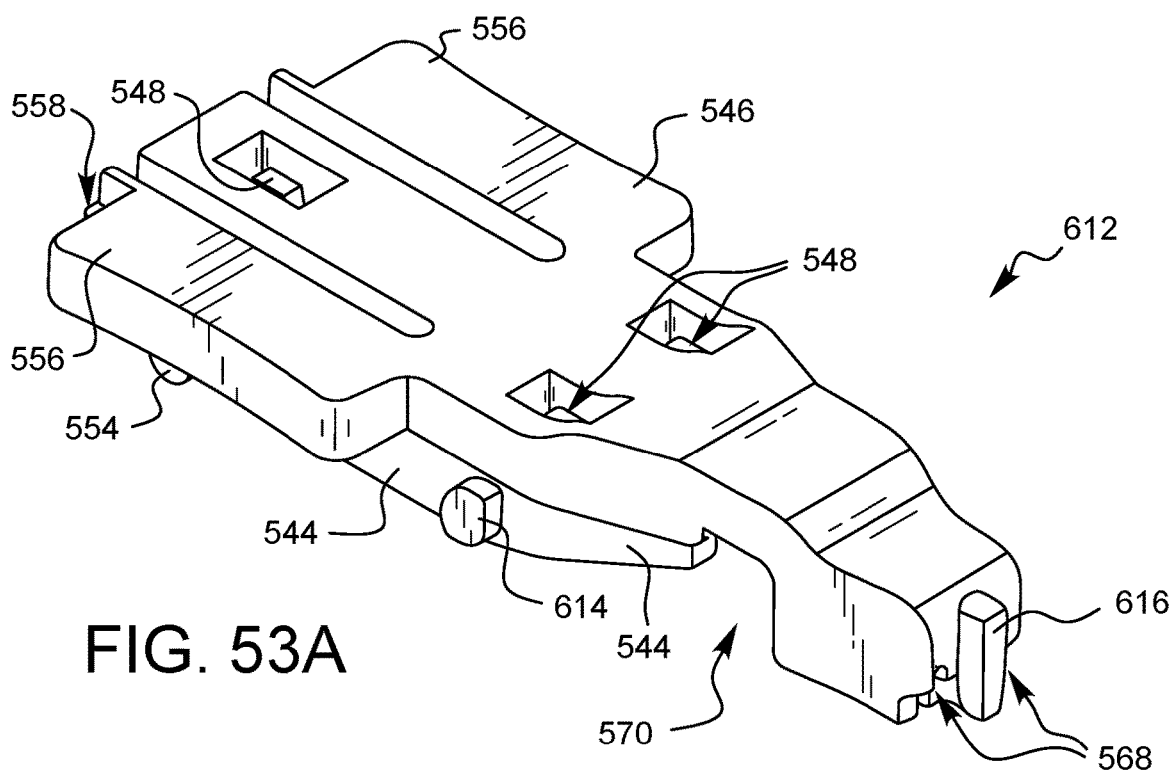
FIGS. 53A and 53B are different perspective views of another cassette embodiment for use with the surgical suturing device of FIG. 49A.
Figure 53B:
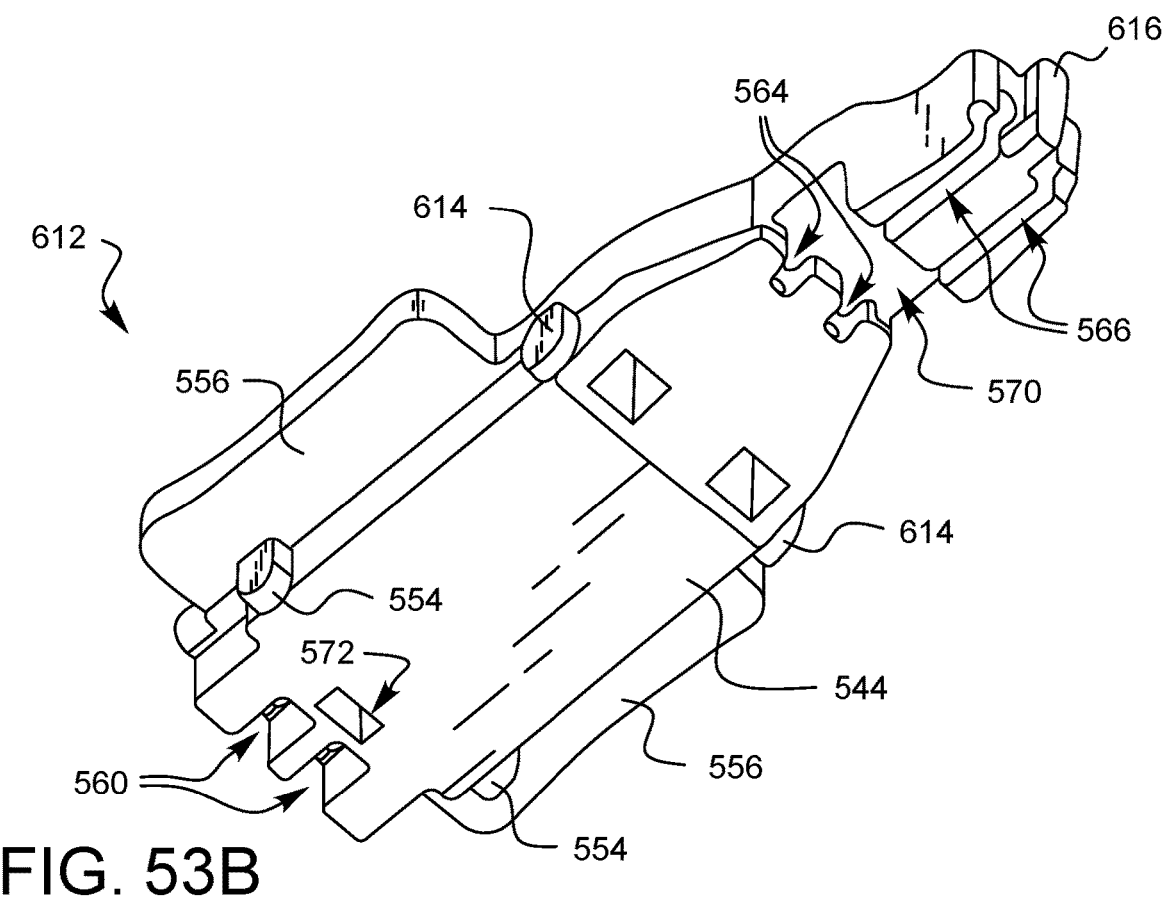

FIGS. 53A and 53B are different perspective views of another cassette 612 embodiment for use with the surgical suturing device of FIG. 49A. This cassette 612 is similar to the cassette of FIGS. 38A and 38B, but has slightly different latching between the cover and the base, has slightly differently shaped pivots 614, has different needles (not visible in this view), and includes a loading alignment guide 616 on the distal end of the cassette 612. The loading alignment guide 616 will be discussed in more detail later in this specification.

Figure 54:
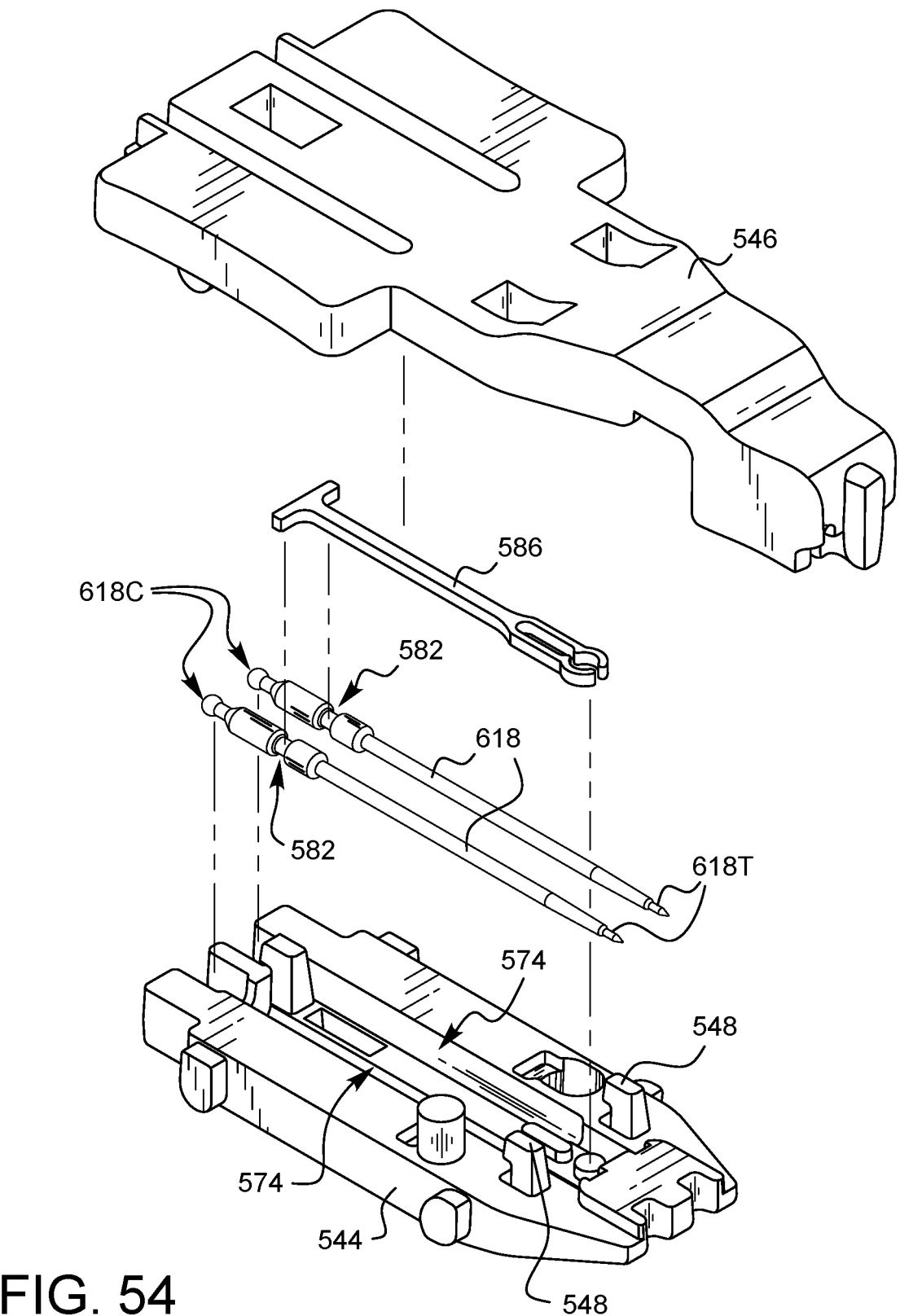
FIG. 54 is an exploded view of the cassette of FIG. 53A.

FIG. 54 is an exploded view of the cassette of FIG. 53A. As noted above, the latching in this cassette is slightly different than the previous cassette. The previous cassette included latches which flexed and snapped into place. This cassette has latches which pass from the base 544 through the cover 546 and then require the base 544 and cover 546 to slide relative to each other in order to secure the latches in place. As noted previously, a wide variety of other techniques known to those skilled in the art exist for coupling the cover to the base. The needles 618 are different, too, in FIG. 54. This embodiment does not have a needle cuff relief, and the connector ends 618C are ball-shaped to fit the different needle receivers 610 of the suturing device embodiment of FIGS. 49 and 52.

FIGS. 55A, 55B, 55C, 55D, 55E, and 55F are top, front, left, right, back, and bottom views of the cassette of FIG. 53A.

Figure 56A:
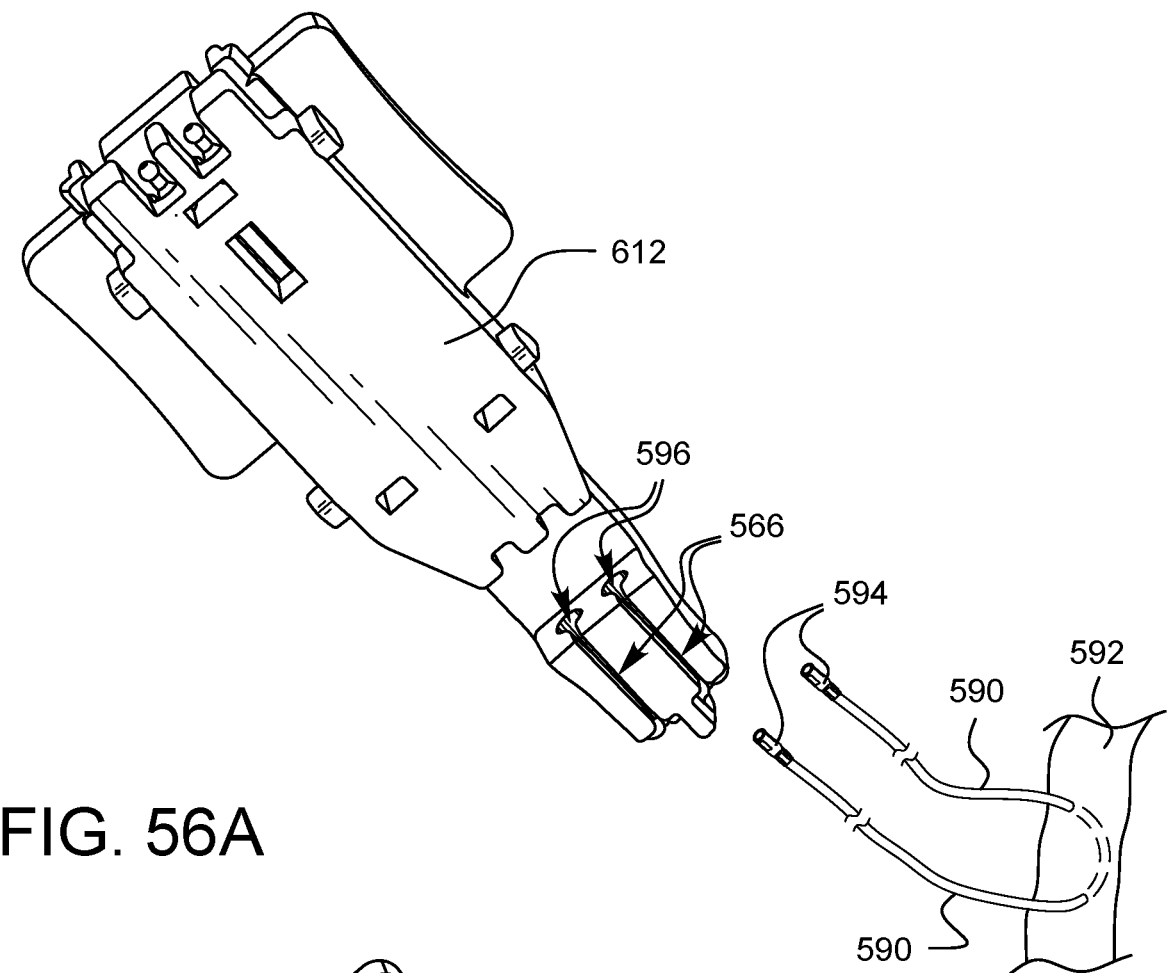
FIG. 56A is a perspective view of a surgical situation where a suture has been stitched into a tissue and ferrules on the ends of the suture are ready to be placed into the cassette of FIG. 53A.
Figure 56B:
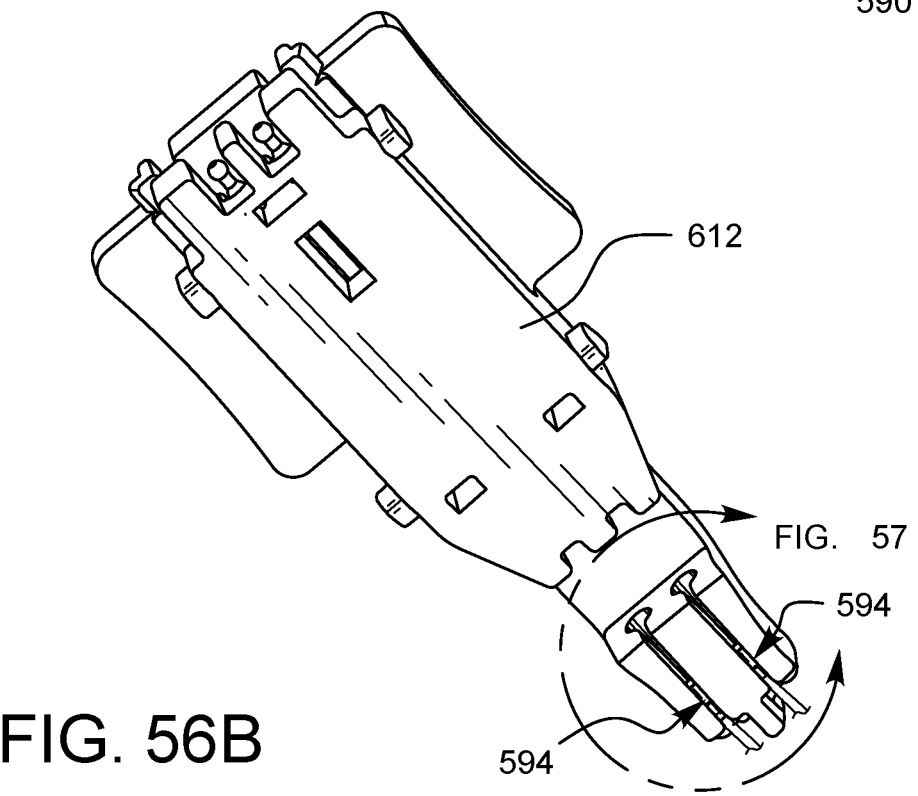
FIG. 56B illustrates the ferrules of FIG. 56A having been installed into the cassette of FIG. 53A.
Figure 57:
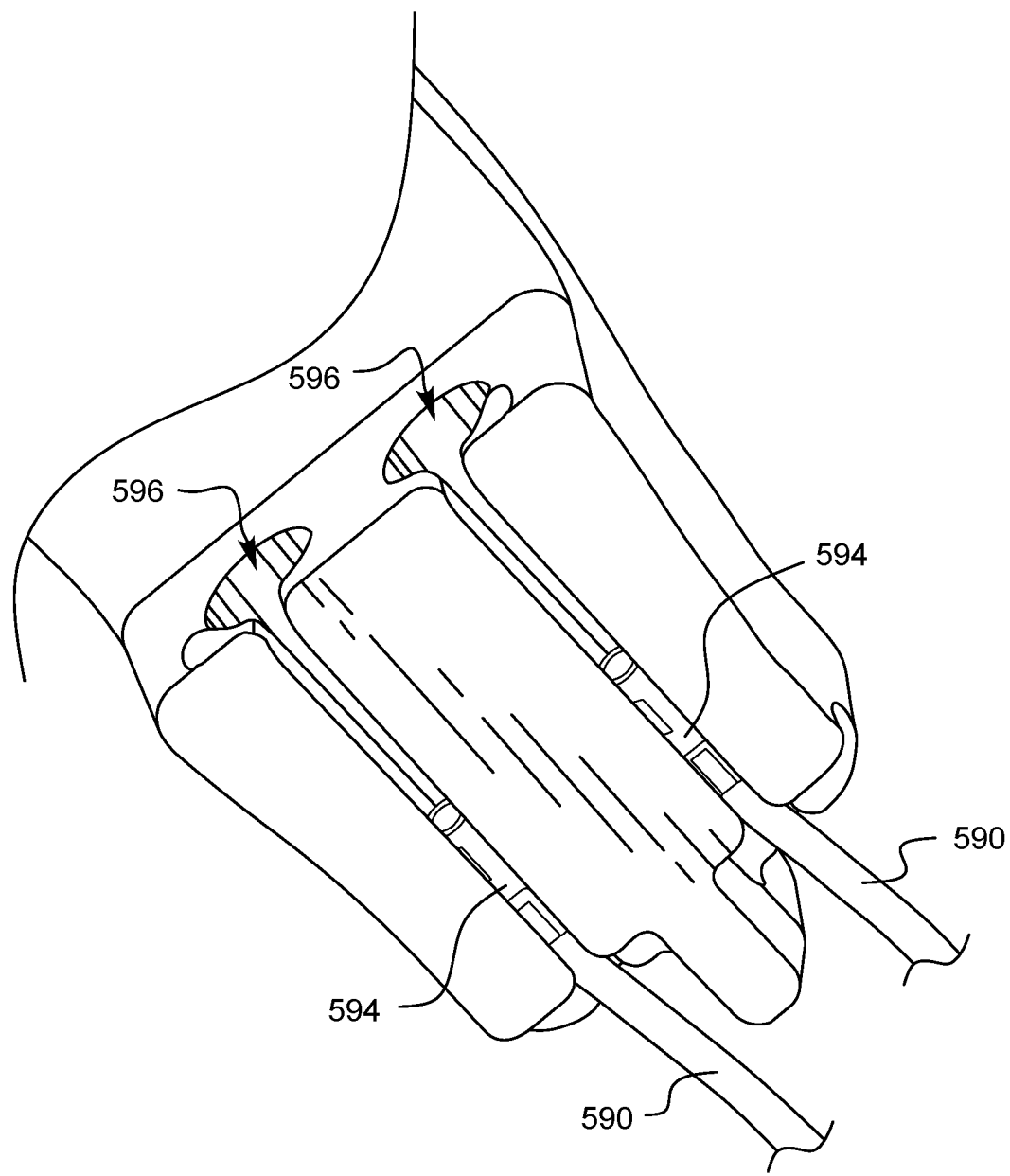
FIG. 57 is an enlarged view of the distal end of the cassette from FIG. 56B showing the ferrules installed in the cassette.

FIG. 56A is a perspective view of a surgical situation where a suture 590 has been stitched into a tissue 592 and ferrules 594 on the ends of the suture 590 are ready to be placed into the cassette 612 of FIG. 53A. FIG. 56B illustrates the ferrules 594 of FIG. 56A having been installed into the cassette 612 of FIG. 53A. The description of these FIGS. is similar to that of FIGS. 41A and 41B. FIG. 57 is an enlarged view of the distal end of the cassette from FIG. 56B showing the ferrules 594 installed in the cassette.

Figure 58A:
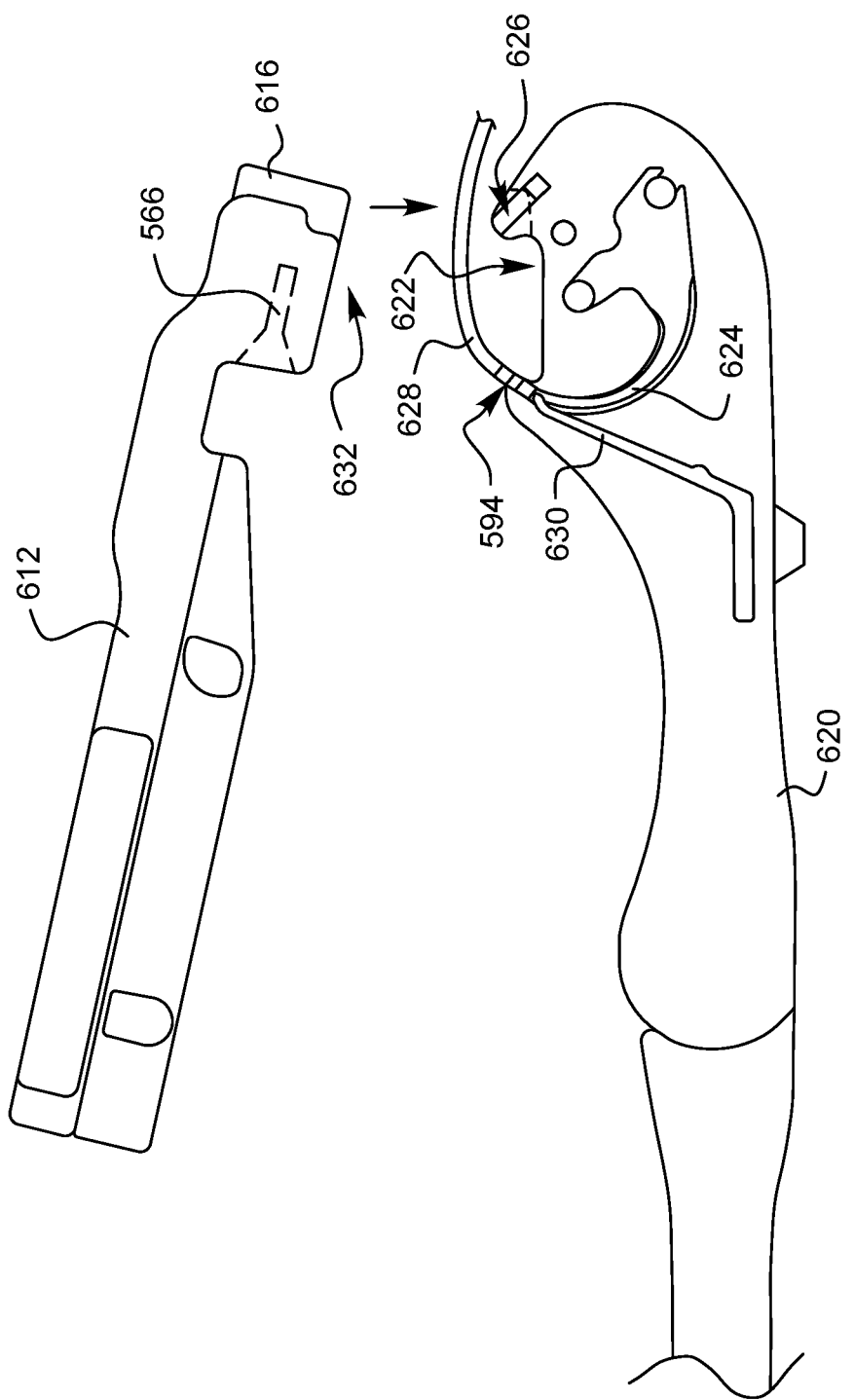
FIGS. 58A-58E illustrate how a suturing device for placing stitches in tissue may be coupled to the cassette in order to facilitate loading of the ferrules into the cassette.
Figure 58B:
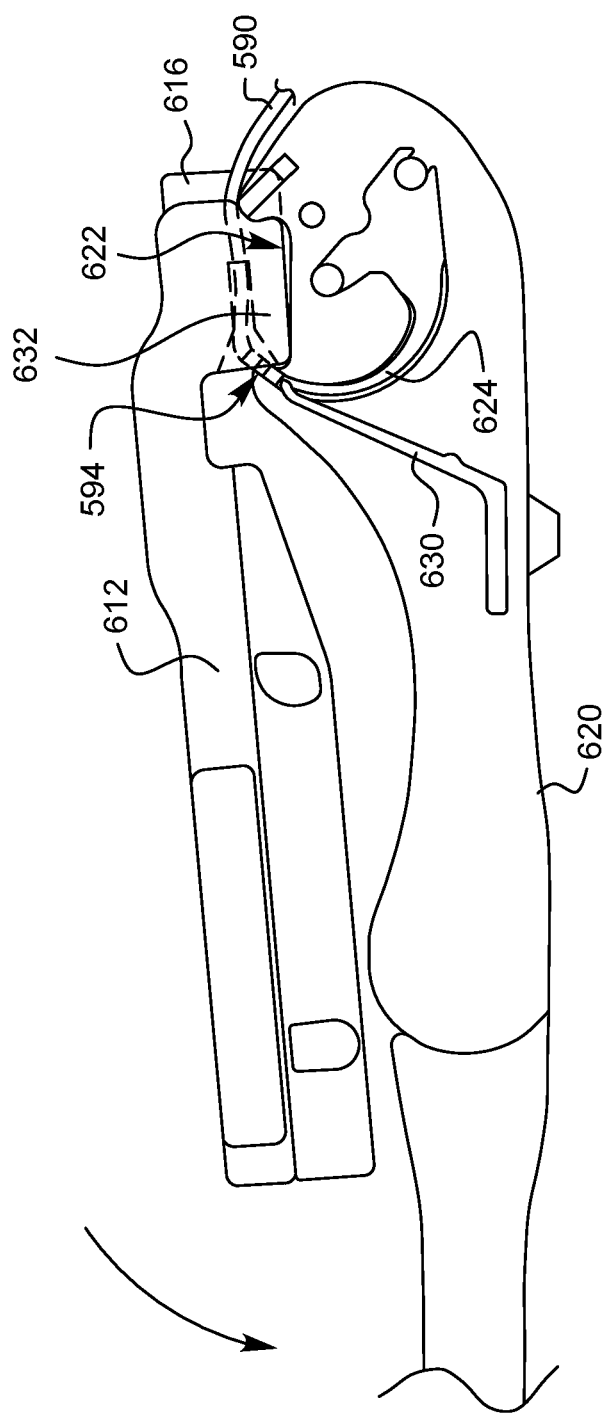
Figure 58C:
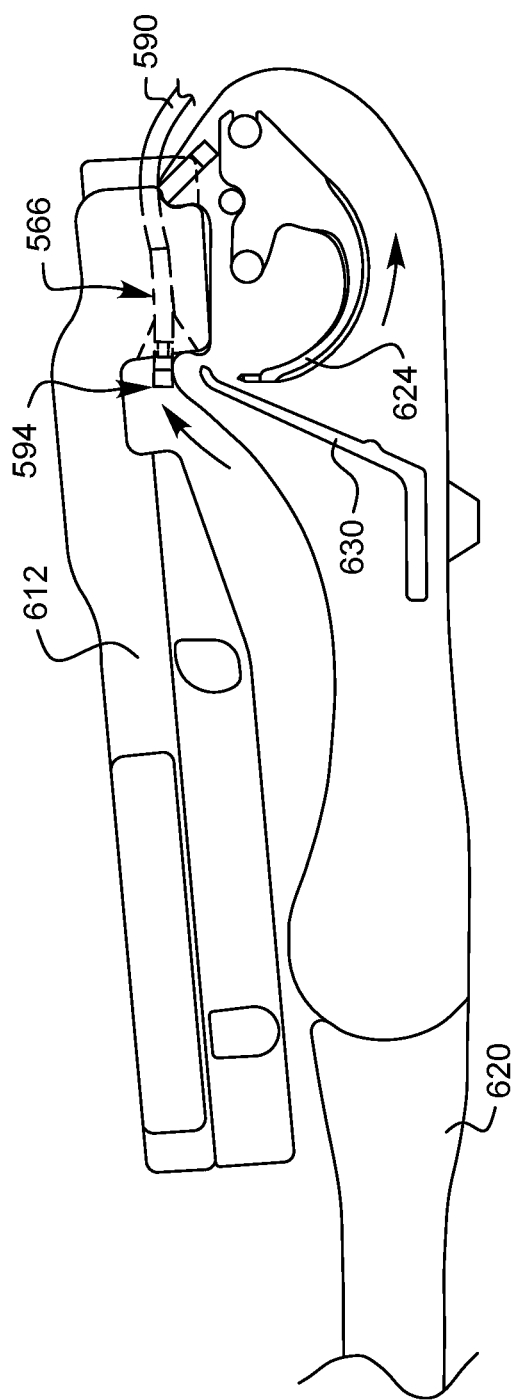
Figure 58D:
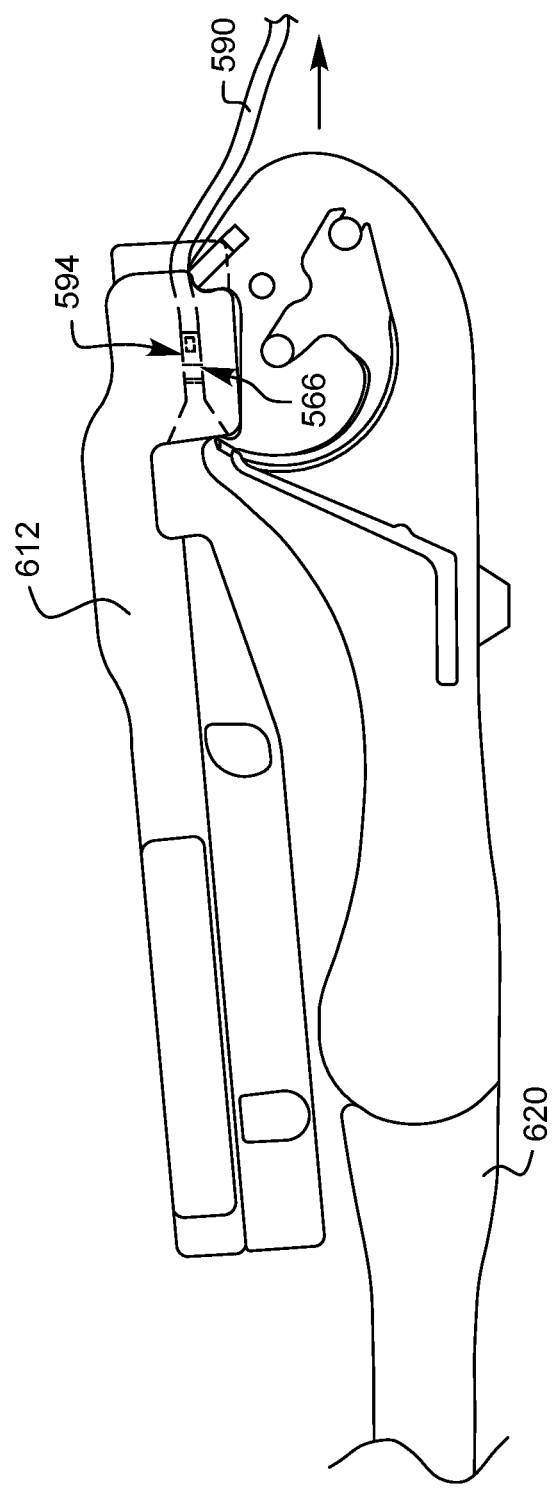
Figure 58E:
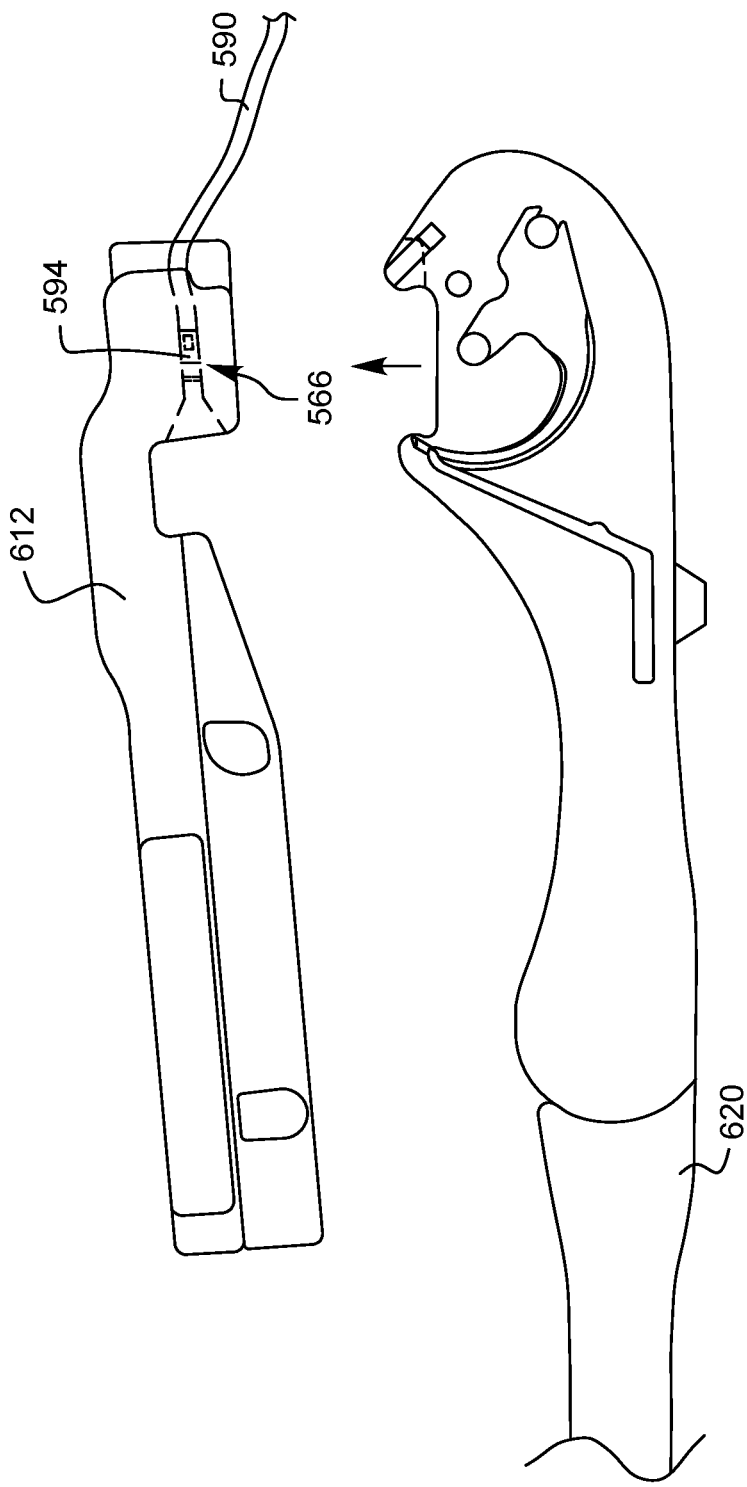

FIGS. 58A-58E illustrate how a suturing device 620 for placing stitches in tissue may be coupled to the cassette 612 in order to facilitate loading of the ferrules 594 into the cassette 612. As shown in FIG. 58A, the tissue suturing device 620 has a tissue bite area 622. As known to those skilled in the art, tissue may be positioned in the tissue bite area 622 and then a tissue needle 624 may be extended from the position shown in FIG. 58A, through the tissue in the tissue bite area 622, and into contact with one or more ferrules 594 which are held in corresponding one or more ferrule holders 626 for the tissue suturing device 620. The tissue needle 624 can then be withdrawn back through the tissue to the position shown in FIG. 58A with the ferrules 594 attached as shown in FIG. 58A. The tissue suturing device 620 can be removed from the tissue and the suture end(s) 628 coupled to the ferrules 594 will be pulled away from the tissue, too. For example, the tissue suturing device 620 could be used to place a stitch into an aortic root and then the device could be pulled out of a minimally invasive opening through which it had been placed to make the stitch. The tissue suturing device 620 also has the ability to move the needle 624 so that the ferrule 594 is pushed against a ferrule removal device 630 which will push the ferrule 594 off of the needle 624. In some embodiments, an operator may use this ferrule release feature 630 to release the ferrule 594 and then the ferrule 594 may be loaded by hand into the ferrule holder 566 of the cassette 612. In this embodiment, however, the cassette 612 has a cassette nose 632 which is shaped to fit into the tissue bite area 622 of the tissue suturing device 620 as illustrated in FIG. 58B. The loading alignment guide 616 mates with a corresponding feature on the tissue suturing device 620 to ensure the ferrule 594 and suture 590 coupled to the tissue needle 624 are in alignment with the ferrule holder 566 of the cassette 612. Depending on the embodiment, the ferrule and/or suture may be partially in the funnel opening leading to the cassette ferrule holder 566 while the ferrule is still attached to the tissue needle. When the ferrule removal feature 630 on the tissue suturing device 620 is activated, as shown in FIG. 58C, the ferrule 594 is released from the tissue needle 624. Now, an operator may pull distally on the suture 590 to seat the ferrule 594 in the cassette ferrule holder 566 as shown in FIG. 58D. Finally, as illustrated in FIG. 58E, the cassette 612 with the loaded ferrule 594 (or ferrules 594) may be removed from the tissue suturing device 620. This may be an easier and quicker way to load the ferrules 594 into the cassette 612 and it also has the advantage of keeping the ferrules 594 aligned by not providing an opportunity for the ferrules 594 to be mistakenly placed in an incorrect ferrule holder 566 (which could cause unwanted tangling of suture lines).

Figure 58F:
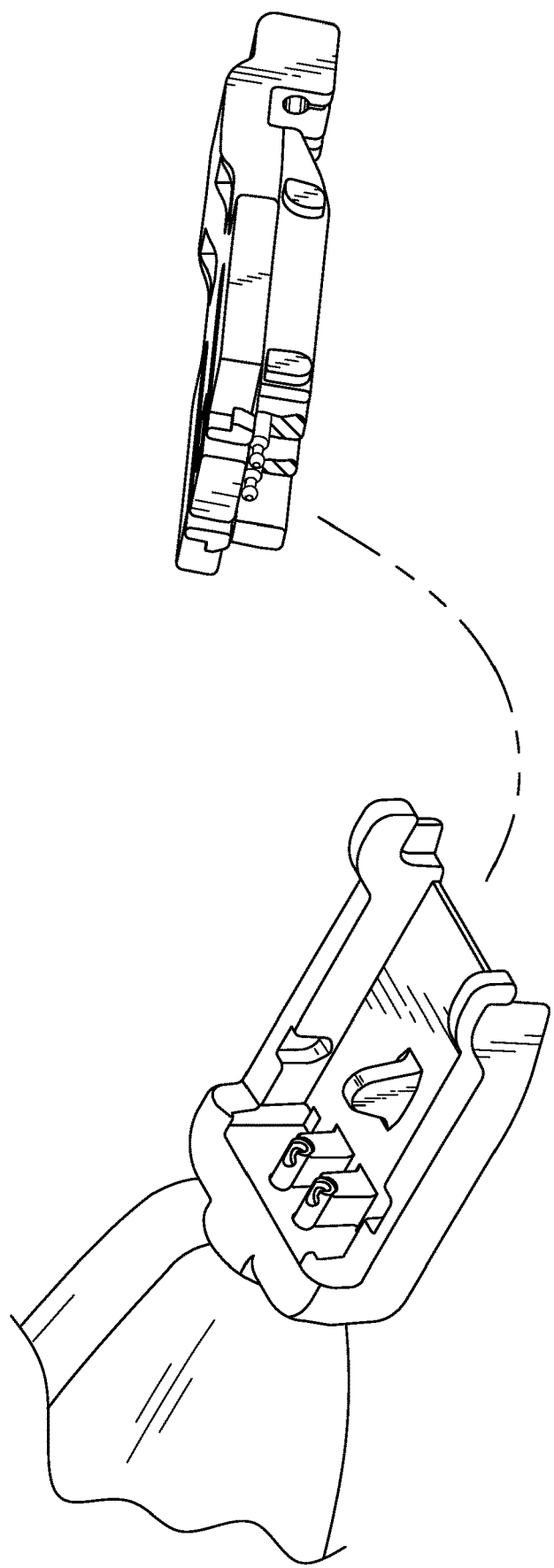
FIG. 58F shows a partially exposed view of the back side of the cassette of FIG. 53A to illustrate the connector ends of the needles in the cassette and how they are configured to mate with the needle drivers of the surgical suturing device of FIG. 52.

FIG. 58F is similar to FIG. 43, but showing the cassette 612 and cassette receiver 484 of FIGS. 53A and 52, respectively.

Various advantages of a prosthetic suturing device have been discussed above. Embodiments discussed herein have been described by way of example in this specification. Various advantages of a surgical suturing device with indexer and magazine, methods, and systems thereof have also been discussed above. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A prosthetic suturing device configured to cooperatively engage a suture having a first and a second suture adapter, the prosthetic suturing device comprising:
   a guide tip having a guide tip proximal portion and a spaced guide tip distal portion, the guide tip proximal portion and guide tip distal portion defining a cuff receiving area therebetween, and the guide tip distal portion comprising first and second apertures configured to receive a corresponding one of the first and the second suture adapters, wherein each of the first and second apertures is configured to hold one of the first and the second suture adapters and preclude passage of the one of the first and the second suture adapter from a distal end of the guide tip distal portion, wherein the guide tip distal portion includes a first suture removal passage connected to the first aperture and extending from the cuff receiving area to a distal end of the guide tip distal portion and a second suture removal passage connected to the second aperture and extending from the cuff receiving area to the distal end of the guide tip distal portion, and wherein the guide tip proximal portion is free of the first suture removal passage and the second suture removal passage;
first and second needles, each needle having an end configured to engage a corresponding one of the first and the second suture adapter;
at least one set of needle guides configured to guide the first and second needles through the cuff receiving area, wherein the at least one set of needle guides comprises a needle guide tube having at least one spiral-like needle track defined therein; and
a grip pointing in a direction substantially orthogonal to the cuff receiving area.

2. The prosthetic suturing device of claim 1, further comprising an actuator movable relative to the grip for moving the first and second needles between a retracted position where the needles are not passing through the cuff receiving area and an engaged position where the needles are passing through the cuff receiving area.

3. The prosthetic suturing device of claim 1, wherein the needle guide tube includes corresponding first and second spiral-like needle tracks defined therein.

4. The prosthetic suturing device of claim 1, wherein the first and second needles are horizontally oriented at a proximal end of the needles, near the grip, and vertically oriented at a distal end of the needles, near the cuff receiving area.

5. The prosthetic suturing device of claim 1, wherein the first and second needles are vertically oriented.

6. The prosthetic suturing device of claim 1, wherein the guide tip further comprises at least one horizontal needle alignment guide.

7. The prosthetic suturing device of claim 1, wherein the guide tip further comprises at least one vertical needle alignment guide.

8. The prosthetic suturing device of claim 1, wherein the guide tip further comprises at least one central alignment guide.

9. The prosthetic suturing device of claim 1, wherein the distal end of the guide tip distal portion defines a terminal end of the prosthetic suturing device.

10. The prosthetic suturing device of claim 1, wherein the guide tip distal portion is fixed relative the guide tip proximal portion.

11. The prosthetic suturing device of claim 1, wherein the grip is asymmetric relative a longitudinal axis passing through the cuff receiving area.

12. A prosthetic suturing device configured to cooperatively engage a suture having a first and a second suture adapter, the prosthetic suturing device comprising:
a guide tip having a guide tip proximal portion and a spaced guide tip distal portion, the guide tip proximal portion and guide tip distal portion defining a cuff receiving area therebetween, and the guide tip distal portion comprising first and second apertures configured to receive a corresponding one of the first and the second suture adapters, wherein each of the first and second apertures is configured to hold one of the first and the second suture adapters and preclude passage of the one of the first and the second suture adapter from a distal end of the guide tip distal portion, wherein the guide tip distal portion includes a first suture removal passage connected to the first aperture and extending from the cuff receiving area to a distal end of the guide tip distal portion and a second suture removal passage connected to the second aperture and extending from the cuff receiving area to the distal end of the guide tip distal portion, and wherein the guide tip proximal portion is free of the first suture removal passage and the second suture removal passage;
first and second needles, each needle having an end configured to engage a corresponding one of the first and the second suture adapter;
at least one set of needle guides configured to guide the first and second needles through the cuff receiving area; and
a grip pointing in a direction substantially orthogonal to the cuff receiving area, wherein the first and second needles are horizontally oriented at a proximal end of the needles, near the grip, and vertically oriented at a distal end of the needles, near the cuff receiving area.

13. The prosthetic suturing device of claim 12, further comprising an actuator movable relative to the grip for moving the first and second needles between a retracted position where the needles are not passing through the cuff receiving area and an engaged position where the needles are passing through the cuff receiving area.

14. The prosthetic suturing device of claim 12, wherein the at least one set of needle guides comprises a needle guide tube having corresponding first and second spiral-like needle tracks defined therein.

15. The prosthetic suturing device of claim 12, wherein the guide tip further comprises at least one horizontal needle alignment guide.

16. The prosthetic suturing device of claim 12, wherein the guide tip further comprises at least one vertical needle alignment guide.

17. The prosthetic suturing device of claim 12, wherein the guide tip further comprises at least one central alignment guide.

18. The prosthetic suturing device of claim 12, wherein the distal end of the guide tip distal portion defines a terminal end of the prosthetic suturing device.

19. The prosthetic suturing device of claim 12, wherein the guide tip distal portion is fixed relative the guide tip proximal portion.

20. The prosthetic suturing device of claim 12, wherein the grip is asymmetric relative a longitudinal axis passing through the cuff receiving area.

* * * * *